(12) United States Patent
Silver et al.

(10) Patent No.: US 12,121,744 B2
(45) Date of Patent: Oct. 22, 2024

(54) DEVICES AND METHODS FOR APPLYING THERAPEUTIC LIGHT TO REDUCE HAZARD TO HEALTH CARE PROVIDERS OF CONTRACTING INFECTIOUS DISEASE

(71) Applicant: Pathy Medical, LLC, Shelton, CT (US)

(72) Inventors: Mikiya Silver, New Haven, CT (US); Gennady Kleyman, Brooklyn, NY (US); Vinod V. Pathy, Shelton, CT (US)

(73) Assignee: Pathy Medical, LLC, Shelton, CT (US)

( * ) Notice: Subject to any disclaimer, the term of this patent is extended or adjusted under 35 U.S.C. 154(b) by 345 days.

(21) Appl. No.: 17/323,155

(22) Filed: May 18, 2021

(65) Prior Publication Data
US 2021/0353959 A1 Nov. 18, 2021

Related U.S. Application Data

(60) Provisional application No. 63/026,319, filed on May 18, 2020.

(51) Int. Cl.
*A61N 5/06* (2006.01)
(52) U.S. Cl.
CPC .... *A61N 5/0624* (2013.01); *A61N 2005/0642* (2013.01); *A61N 2005/0652* (2013.01); *A61N 2005/0661* (2013.01)
(58) Field of Classification Search
CPC .................. A61N 5/0624; A61N 5/067; A61N 2005/0642; A61N 2005/0652; A61N 2005/0661; A61N 2005/0647; A61N 2005/0659; A61N 2005/0606;
(Continued)

(56) References Cited

U.S. PATENT DOCUMENTS

| 5,165,395 A | * | 11/1992 | Ricci | ................. A41D 13/1146 55/DIG. 35 |
| 8,733,356 B1 | * | 5/2014 | Roth | ................. A62B 18/003 128/205.27 |
| 11,033,653 B1 | * | 6/2021 | Gandhi | ................. A62B 18/025 |

(Continued)

FOREIGN PATENT DOCUMENTS

| CN | 108211066 A | 6/2018 |
| WO | 95/33506 A1 | 12/1995 |

(Continued)

OTHER PUBLICATIONS

International Search Report issued in PCT/US2021/032955, dated Sep. 2, 2021.

(Continued)

*Primary Examiner* — Joseph M Dietrich
*Assistant Examiner* — Michael T. Holtzclaw
(74) *Attorney, Agent, or Firm* — Locke Lord LLP; Scott D. Wofsy; Gabrielle L. Gelozin

(57) ABSTRACT

A therapeutic light assembly used for reducing a patient's viral load including a housing containing at least one therapeutic light source configured to emit light at air exiting the patient's airway, a power source coupled to the at least therapeutic light source, and a tubing attachment coupled to the housing configured to secure the housing to a patient's tubing.

7 Claims, 49 Drawing Sheets

(58) Field of Classification Search
CPC .... A61N 2005/0607; A61M 2205/052; A61M 2205/053; A61M 16/04; A61M 16/0666
See application file for complete search history.

(56) References Cited

U.S. PATENT DOCUMENTS

| | | | |
|---|---|---|---|
| 2006/0177356 A1* | 8/2006 | Miller | A61L 9/20 |
| | | | 422/121 |
| 2010/0076526 A1 | 3/2010 | Krespi et al. | |
| 2016/0271288 A1* | 9/2016 | Davis | A61M 16/107 |
| 2016/0317832 A1 | 11/2016 | Barneck et al. | |
| 2017/0281966 A1 | 10/2017 | Basiony | |
| 2019/0381203 A1* | 12/2019 | Zaborsky | A61L 2/10 |
| 2020/0261608 A1* | 8/2020 | Crosby | A61L 2/0047 |
| 2021/0275713 A1* | 9/2021 | Mcdaniel | A41D 13/11 |
| 2021/0290793 A1* | 9/2021 | Tung | A41D 13/1184 |
| 2021/0298391 A1* | 9/2021 | Keene | A41D 13/1192 |

FOREIGN PATENT DOCUMENTS

| | | | | |
|---|---|---|---|---|
| WO | WO-2011083381 A1 * | 7/2011 | | A61N 5/0603 |
| WO | WO-2014160149 A2 * | 10/2014 | | A42B 3/286 |

OTHER PUBLICATIONS

Written Opinion of the International Searching Authority dated Sep. 2, 2021, issued during the prosecution of PCT International Patent Application No. PCT/US2021/032955, 5 pages.

\* cited by examiner

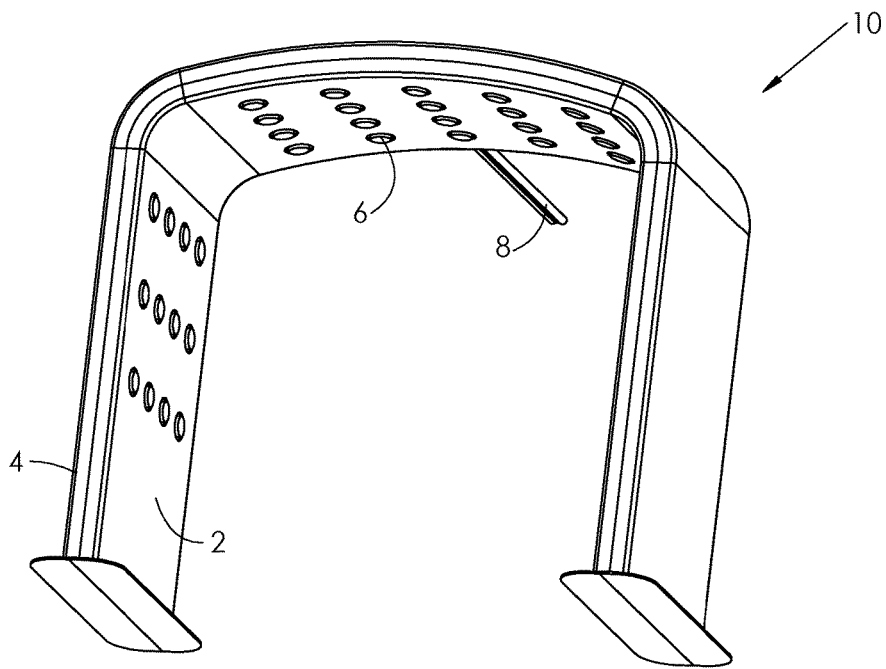
FIG. 1
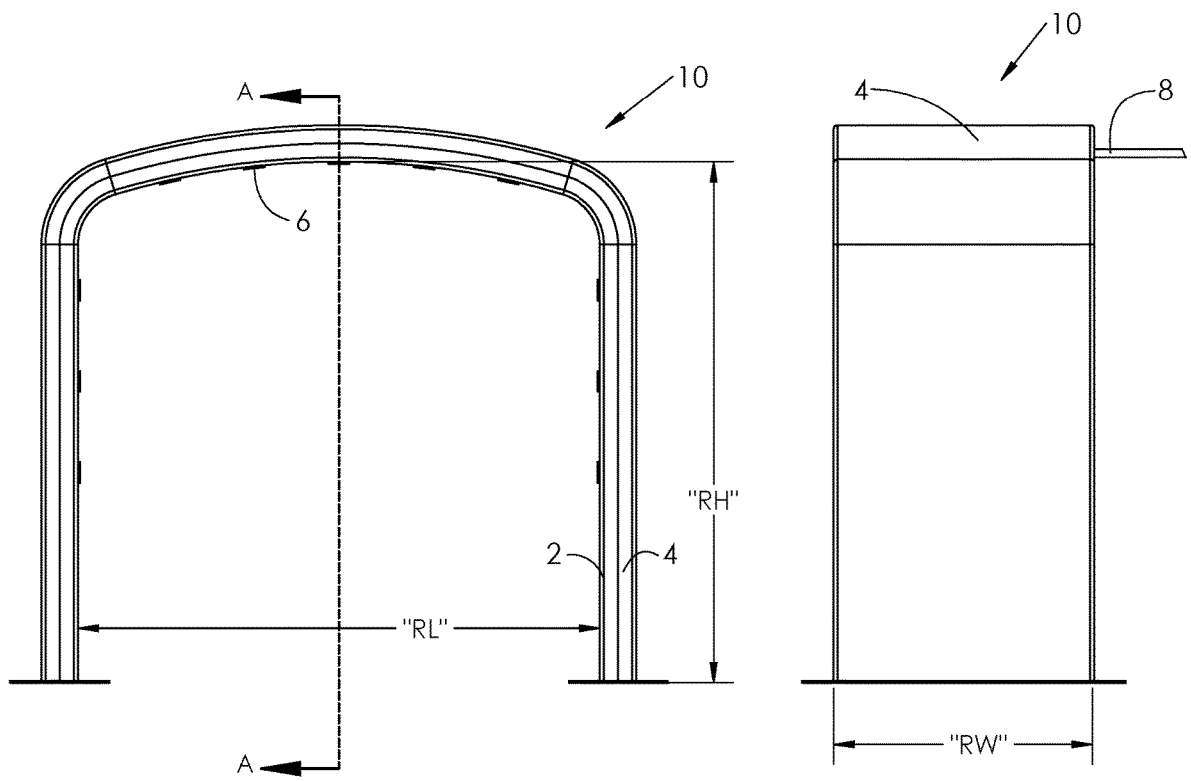
FIG. 2
FIG. 3

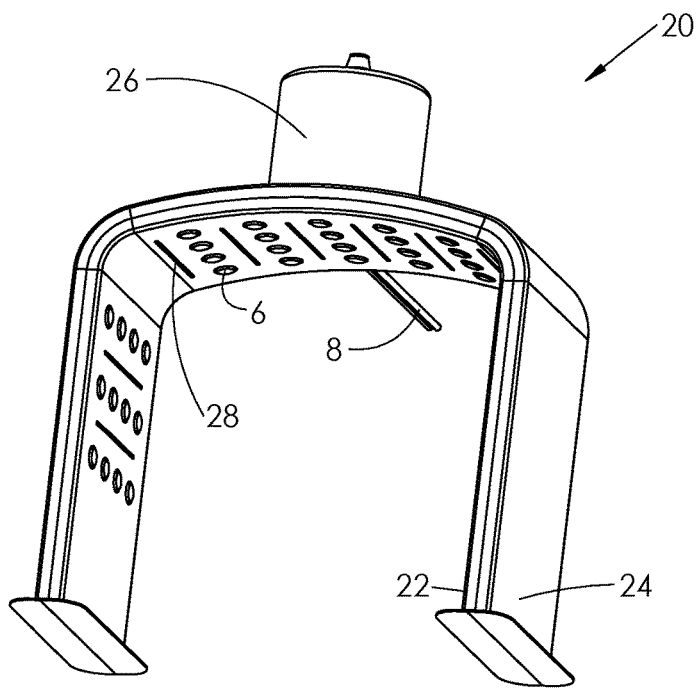
FIG. 17
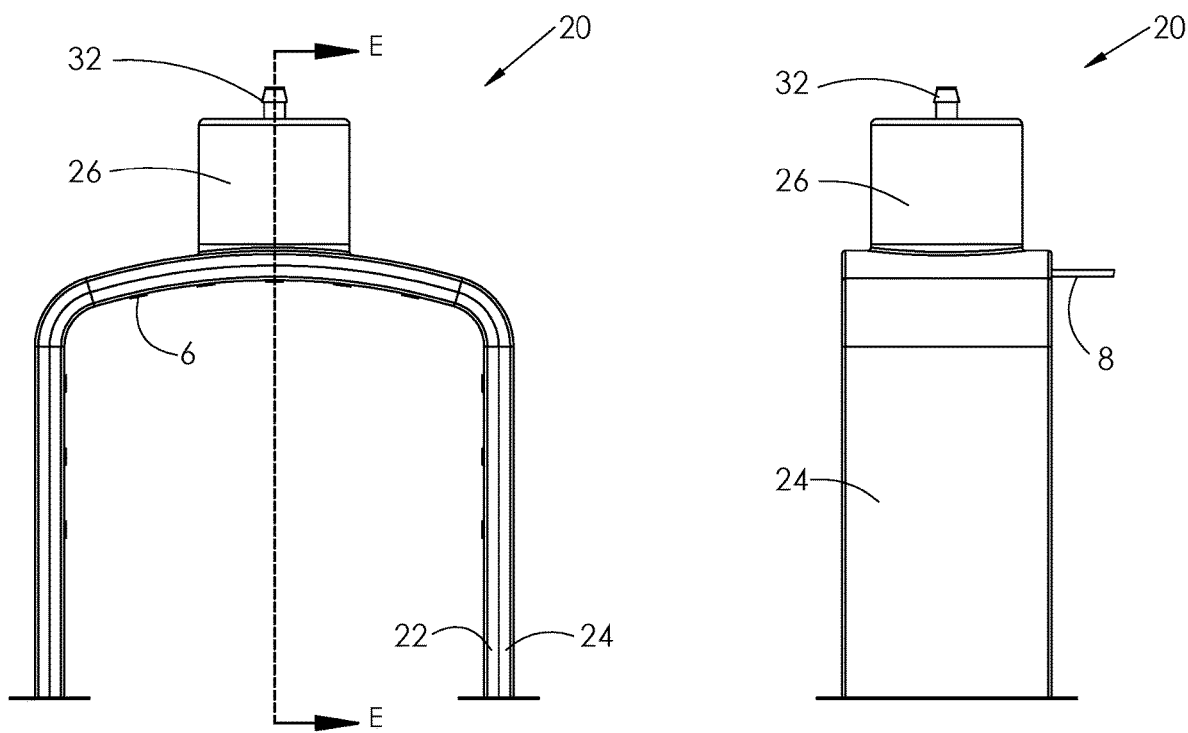
FIG. 18
FIG. 19

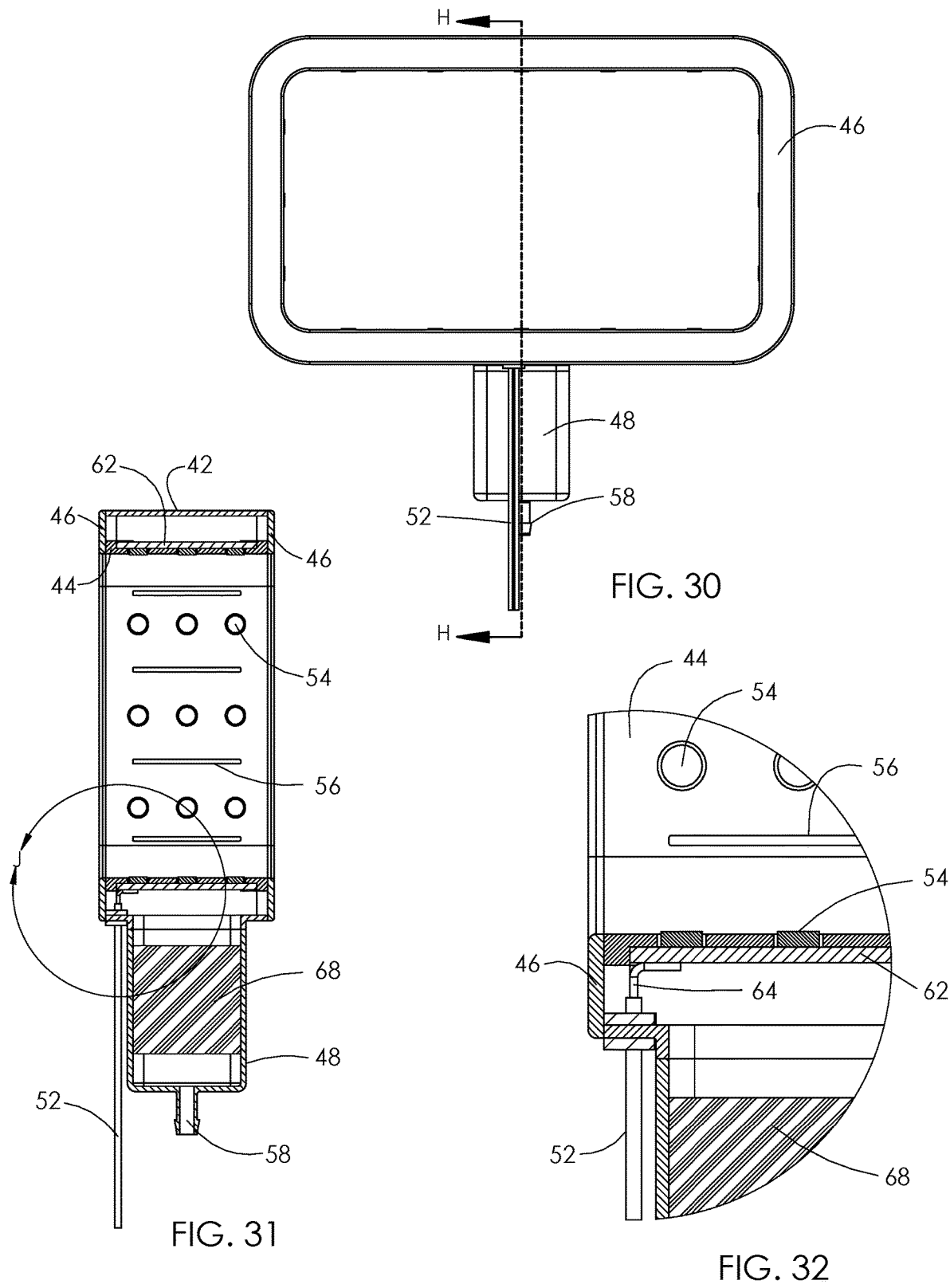

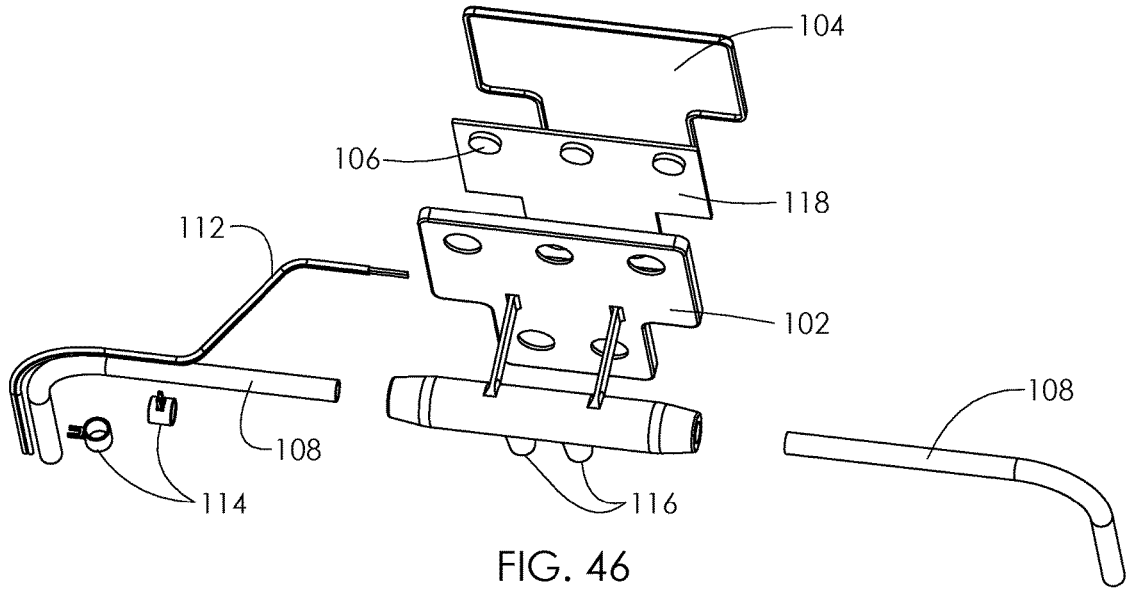
FIG. 46
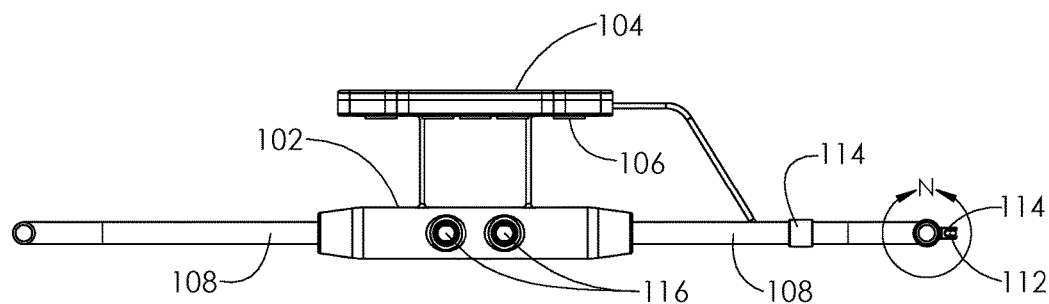
FIG. 47
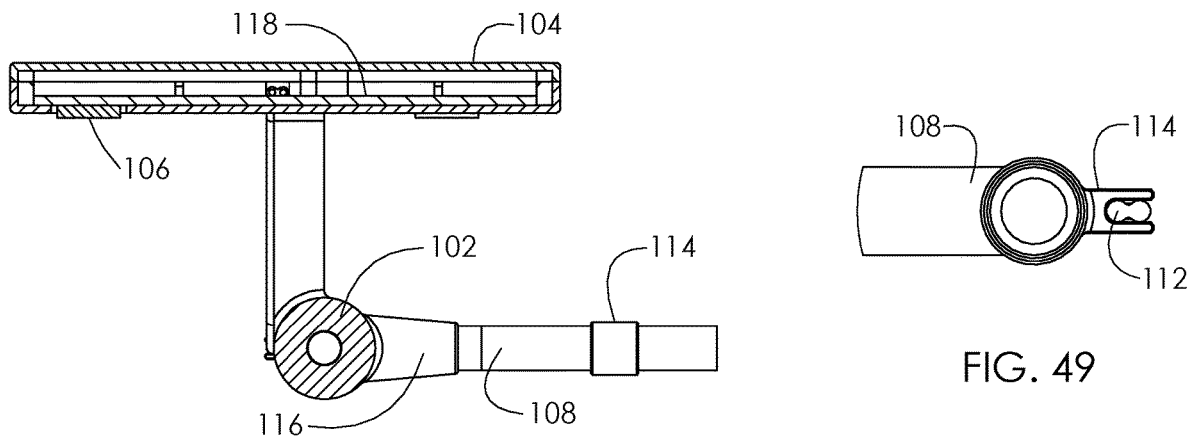
FIG. 48
FIG. 49

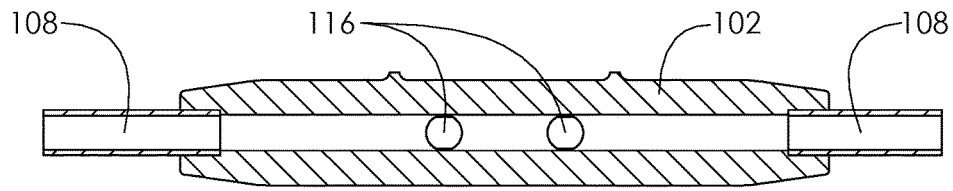
FIG. 50
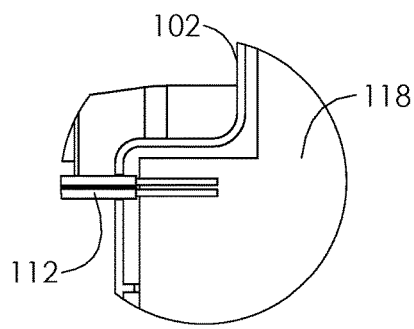
FIG. 51
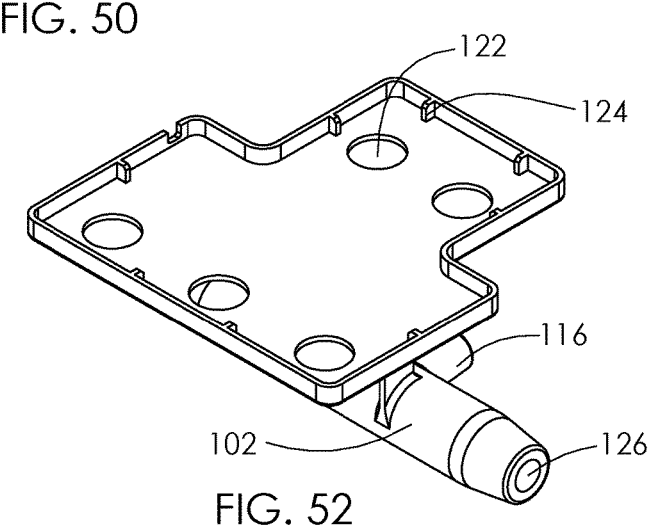
FIG. 52
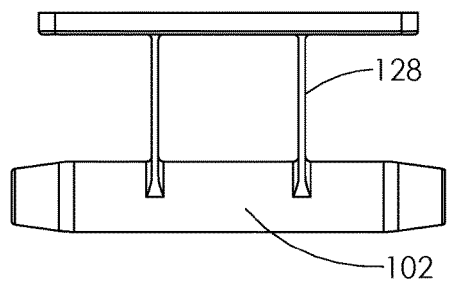
FIG. 53
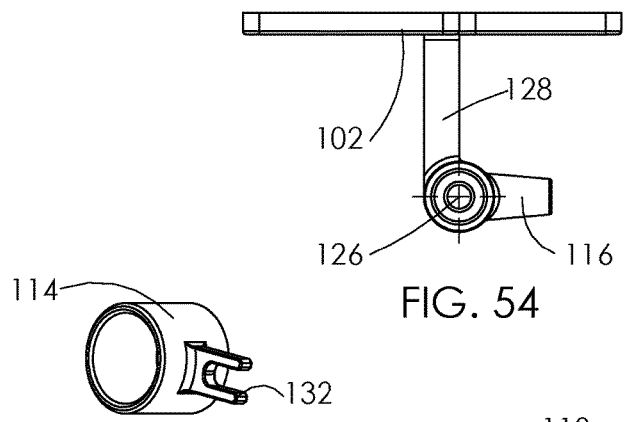
FIG. 54
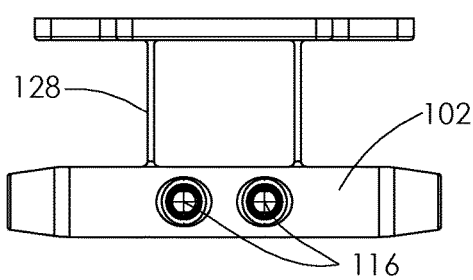
FIG. 55
FIG. 56
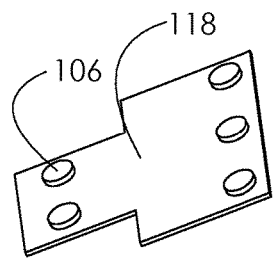
FIG. 57

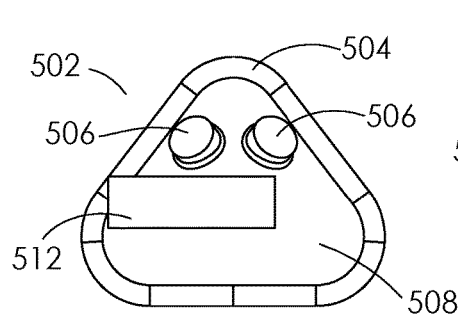
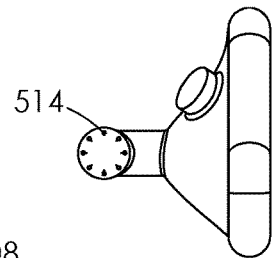
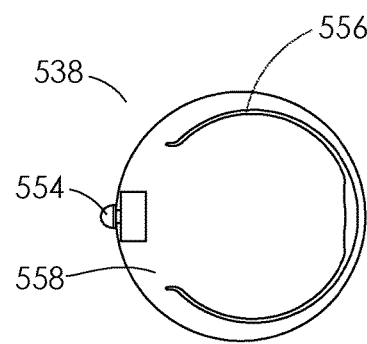
FIG. 116  FIG. 117  FIG. 118
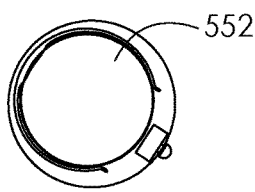
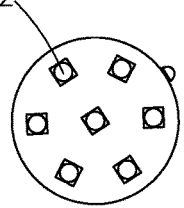
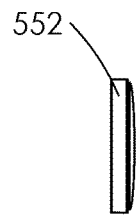
FIG. 119  FIG. 120  FIG. 121  FIG. 122
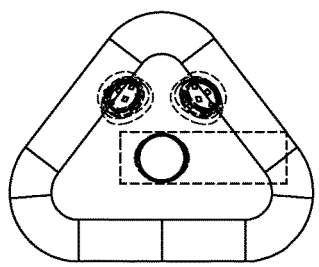
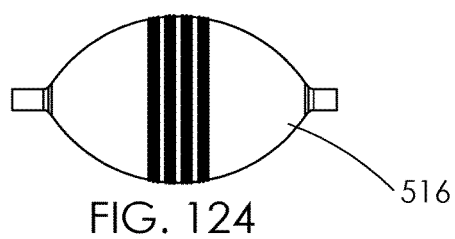
FIG. 123  FIG. 124
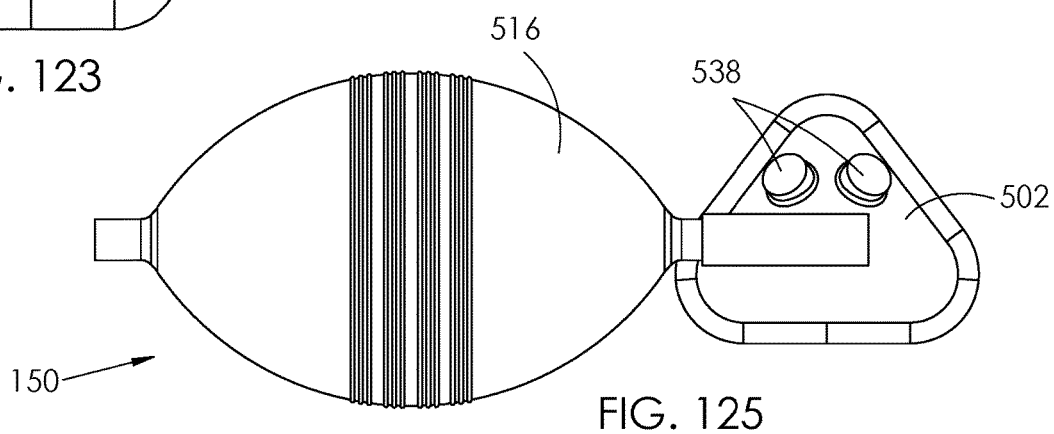
FIG. 125

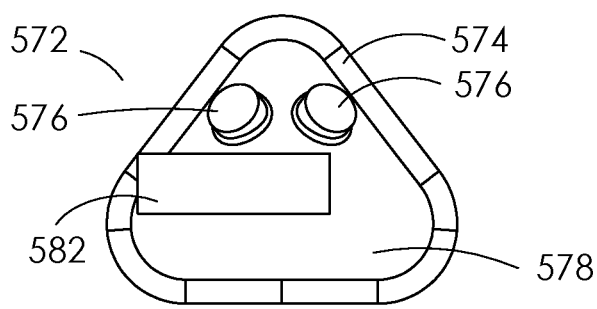
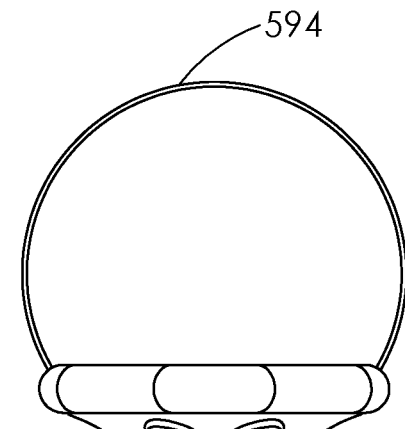
FIG. 131
FIG. 132
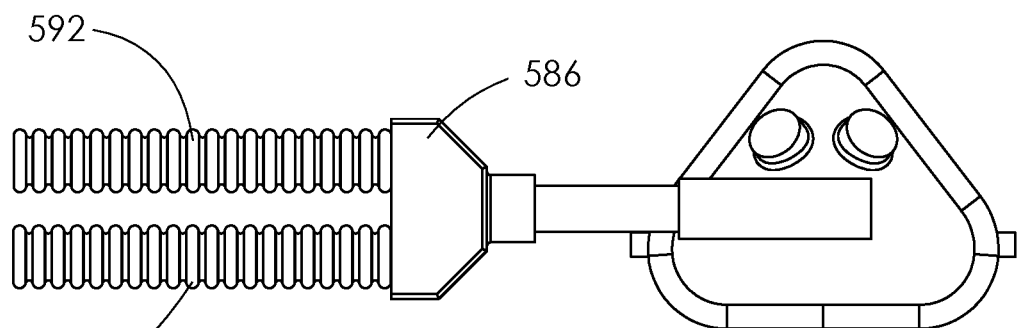
FIG. 133
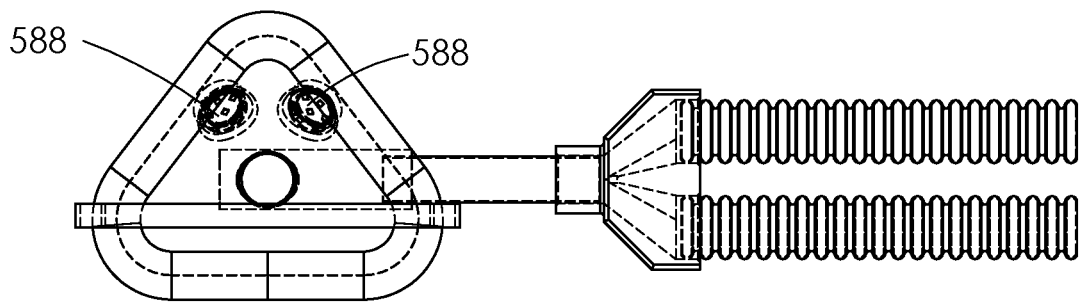
FIG. 134

DEVICES AND METHODS FOR APPLYING THERAPEUTIC LIGHT TO REDUCE HAZARD TO HEALTH CARE PROVIDERS OF CONTRACTING INFECTIOUS DISEASE

CROSS-REFERENCE TO RELATED APPLICATIONS

This application claims priority to and the benefit of U.S. Provisional Application No. 63/026,319, filed May 18, 2020, the entire contents of which are herein incorporated by reference in their entirety.

BACKGROUND OF THE INVENTION

1. Field of the Invention

The subject invention is directed to surgical instrumentation, and more particularly, to devices and methods for applying or otherwise using therapeutic light to reduce hazard to healthcare providers of contracting infectious disease.

2. Description of the Related Art

A virus is an infectious agent that is small and has a simple composition that can multiply only in living cells of animals, plants, or bacteria. Specifically, viruses are microscopic parasites, generally much smaller than bacteria. They are unable to thrive and reproduce outside of a host body. There are many types of viruses, ranging from the rhinovirus which frequently causes the common cold, to viruses that are the cause of contagions such as 2014 outbreak of Ebola in West Africa, the 2009 H1N1/swine flu pandemic, and more recently the 2019 novel coronavirus (SARS-COV-2) which causes the disease better known as COVID-19. Many of these viruses are primarily transmitted through direct contact of mucous membranes.

The direct contact can be described more specifically as spreading through respiratory droplets produced when an infected person coughs or sneezes. These droplets can land in the mouths or noses of people who are nearby or possibly be inhaled into the lungs. For example, the seasonal flu virus and the novel coronavirus are both thought to be spread primarily through close contact with aerosolized droplets expelled from the nose and mouth of an affected person. One can become infected not only by direct contact, such as kissing, but also by even talking in close proximity with someone who is affected.

The seasonal flu virus or the novel coronavirus can also be transferred by touching a tabletop, phone, or other surface that was coughed upon within the prior several hours or even days, if it had not since been disinfected, and then touching one's eyes, nose, or mouth. Data reveals that the R0 metric, which represents how many people are infected by an individual harboring a virus, is between 2 and 2.5 people for the novel coronavirus. This number is significantly higher than the seasonal flu, whose R0 value is approximately 1.3. With the proper preventive measures, the R0 values can decrease, and it has been said that reducing the R0 value to less than 1 would end the pandemic.

Because Health Care Professionals (HCPs) routinely are in very close proximity to infected patients, their risk is great. During each of these contagions there has been a high infection rate on our HCPs as they treat their patients. Reports have shown that up to 25% of confirmed cases in recent pandemics have been in HCPs. The added exposure and the risk to infecting other vulnerable patients increases the potential societal impact. Furthermore, sick health care providers have to be removed from the healthcare system as they recover and are unable to treat patients, further compounding demand and shortages during an epidemic.

Intubation is a medical procedure that typically involves inserting a flexible plastic tube into a patient's mouth and down into their airway. This is a common procedure, carried out in operating rooms, emergency departments, and intensive care units (ICUs) around the world. Intubation can be necessary for several reasons, including for mechanical ventilation for an anesthetized patient undergoing a surgical procedure or to improve oxygen saturation for a patient with damaged lungs or suffering from a respiratory illness.

Ventilation has been used to treat patients suffering from many different viruses including COVID-19. Once intubated, air is forced into the lungs via a machine or manually with a bag or other mechanism.

There are several different types of intubation classified based on the location of the tube and what it is trying to accomplish. Endotracheal tube (ETT) intubation involves passing a tube through the nose or mouth into the trachea to help a person breathe while under anesthesia or due to a distressed airway. Nasogastric intubation involves passing the tube through the nose and into the stomach to remove air or to feed or provide medication to the patient. Fiberoptic intubation is when a physician inserts a tube with a camera into the throat so as to examine the throat or to assist endotracheal intubation when a person cannot extend or flex their head appropriately, or when the anatomy proves unusual or difficult. Laryngeal mask airway (LMA) is a type of supraglottic airway device that is a less invasive alternative to endotracheal tube intubation in certain clinical scenarios. A Tracheotomy or Tracheostomy tube is inserted through a surgically created hole, or stoma, through the trachea via the skin in front of the neck.

The primary purposes of intubation include opening up the airway to give oxygen, anesthesia, or medicine; removing blockages; helping a person breathe if they have collapsed lungs, heart failure, or trauma; allowing doctors to look at the airways; and helping prevent a person aspirating liquids. All of these intubation methods require close contact of an HCP to a patient.

The intubation procedure will vary depending on its purpose and whether it occurs in an operating room or in an emergency situation. Typically, intubation precedes placing a patient on a ventilator so as to assist with their breathing while under an anesthetic or during a severe illness.

In the operating room or other controlled setting, a doctor will typically first sedate the person. The doctor will then insert a laryngoscope into the person's mouth to aid in the insertion of the flexible tubing. The doctor uses the laryngoscope to locate sensitive tissues, such as the vocal cords, and avoid damaging them. If the doctor is having trouble seeing, they may insert a small fiberoptic camera to help guide them. In the operating room, doctors usually use intubation to help a person breathe while they are under anesthesia.

HCPs such as physicians, nurses, nurse anesthetists, anesthesia technicians, and respiratory therapists intubate and regularly care for intubated patients. In addition to the insertion of the intubation/ventilator tube and hooking up the ventilator, they may also need to reposition, clean, remove, or replace intubation tubes as well as suction out mucus or other liquid that has gathered in a patient's mouth. Being so close to the patient's respiratory system greatly increases their risk of exposure to patient droplets and aerosolized transmissible viral infections.

Smoke produced in surgical procedures that utilize electrosurgery may also pose an added risk to HCPs as it relates to transmission of aerosolized viruses. Electrosurgery utilizes a heat-generating electrical device with a metal "blade" to burn or vaporize tissue in order to remove it or assist in its excision, while also cauterizing or sealing blood vessels to minimize bleeding. A wealth of literature exists studying the potential transmission of biological material through surgical smoke generated from electrosurgery devices, lasers, and ultrasonic scalpels.

Researchers have identified HIV DNA2 and intact strands of HPV DNA in laser smoke. Researchers have further studied the transmission of infection through surgical smoke. In one study, for example, researchers demonstrated that transmission of the HIV DNA recovered from surgical plume to cultured cells was, in fact, possible. One case of a surgeon contracting laryngeal papillomatosis after treating a patient with anogenital condyloma with laser tissue ablation strongly suggests transmission through surgical smoke. The HPV strain contracted by the surgeon matched those of the patient treated, and no other methods of exposure other than inhalation of surgical plume were identified as risk factors. Contraction of verrucae (a highly contagious virus-derived wart treated by laser ablation) by laser operators in unusual sites such as the anterior nares of the nasal cavity have also been documented and suggest transmission via surgical smoke.

A study of surgeons treating warts at the Mayo Clinic revealed that while prevalence was not elevated in the group relative to the general population, 13% of surgeons contracted warts of the nasopharynx, which is an uncommon infection site in the general population, and can best be explained by a relationship to smoke plume inhalation. There is increased risk that surgeons, physician's assistants, surgical residents, nurses, scrub technicians and other HCPs who come into contact with surgical plume can contract a virus from an infectious patient.

HCPs typically utilize Personal Protective Equipment (PPE) when treating patients with known viruses. Without knowledge of a highly contagious virus, simple facemasks and possible gloves are used as standard PPE. To limit the spread of disease during outbreaks with greater transmissibility than common colds and the seasonal flu, HCPs enact additional measures to protect themselves while caring for infected patients including the use of isolation gowns, facemasks, face shields, N95 masks, goggles or other types of eye protection, and sterile gloves. Although the PPE thresholds during known outbreaks increases and protection of HCPs improves, this method still allows for many scenarios in which HCPs may get sick.

PPE is only effective once it is used, and during the beginning of an outbreak before HCPs are made aware of a new virus, normal masks and gloves may be insufficient to prevent transmission of a highly transmissible disease. Other reasons that PPE can fail to protect HCPs include improper use, failure of the PPE materials or devices, self-contamination, supply shortages, reuse, and more. There have been clinical trials on PPE that have been treated with antibacterial agents that have proven to be ineffective, while other studies suggest that each HCP should enter a UV chamber prior to removing PPE following treatment of infected patients.

Unfortunately, the latter is not a practical solution in many countries or most facilities, even in developed countries such as the United States. Studies have identified viral RNA traces on the walls of hospitals and operating rooms even when PPE protocols were used properly. Furthermore, studies have shown that more exposure to a virus could lead to potential more severe cases and higher transmission rates. With hospitals and other healthcare facilities treating infected patients being a hub of viral activity, simply protecting from the virus is not enough.

The most effective manner in which to protect HCPs from a contact-transmitted disease is to physically remove or eliminate the hazard itself. Elimination is followed by replacing the hazard and substituting for another. Substitution is followed by developing and engineering controls in order to isolate people from the hazard and by enacting administrative controls to change the way people work. Reducing or limiting the amount of hazard or the exposure can reduce the likelihood of transmission or the number of transmissions. Finally, PPE is one of the least effective manners in which to protect HCPs from a contact-transmitted disease. Thus, the use of PPE alone does not eliminate the hazard to HCPs who are treating patients with a contagion. Reducing the viral load in a hospital has compounding impact of increasing the effectiveness of all subsequent policies and procedures put in place to reduce viral transmission to HCPs.

Currently treatments including UV-C light medical treatments include lamps, room disinfection, and bulky commercial handheld UV light emitters. Devices like the Biomation Thera-Wand are used for wound care but are not sterilized and brought into the surgical arena.

One of the most significant hindrances to utilization thus far has been the requirement for a pause in surgery specifically to place the bulky UV-C device in proximity to the tissues at risk. Another hindrance is the need to manufacture a sterile device that can be used within the sterile operating field during interventions like surgery.

Other types of therapeutic light have shown effectiveness in viral and bacterial load including, but not limited to, UV light, UV-C light, Far UV-C light, infrared light, near-infrared light, low level laser light, and White light.

Past methods of protecting HCPs and other medical personnel from the spread of viral loads have failed to provide acceptable results, along with the aforementioned hindrances show there is a clear need for alternative approaches to treating surgical areas on a patient. The present disclosure provides a solution for this need by integrating therapeutic light to devices such as intubation tubes and masks as well as suction tubing commonly used during surgery.

SUMMARY OF THE INVENTION

What is disclosed is a set of devices and methods for protecting Health Care Providers (HCPs) via the reduction of viral count, bacteria count, or other potentially infectious or infection-causing agents. Therapeutic light is applied directly at the source (typically the mouth and nose area of an infectious or potentially infectious patient) to denature, deactivate, kill, or otherwise render harmless a portion of these infectious agents. Other locations to apply therapeutic light include near a surgical site of an infectious or potential infectious patient or along the path towards a health care provider including in patient respiratory devices and in Personal Protective Equipment (PPE). The impact of these devices and methods is to reduce the hazard to HCPs via the partial (reduction) or complete (elimination) of infectious agents thereby reducing or eliminating exposure to the HCP.

The devices are intended as sterile disposable, partially sterile disposable, non-sterile disposable, or reusable devices.

The devices may be designed to apply the therapeutic light at an optimal distance for efficacy, especially when integrated into a static device meant to apply therapeutic light directly to a potential source of infectious agents. An optical lens may be used to focus or redirect therapeutic light directly to improve efficacy of the therapeutic light treatment or ensure that the light is only applied where desired.

The devices may be utilized in any kind of patient care facility including the emergency room, the operating room, the intensive care unit (ICU), respiratory therapy treatment centers, and other locations where a Health Care Provider may benefit from reducing the risk of contracting a harmful infectious agent. The devices can be used continually throughout a procedure such as a surgery or throughout the duration of intubation, periodically during care (i.e. once per hour during intubation), or at specified times during care (i.e. when tubing is inserted or removed, only when a Health Care Provider is present, etc.)

The concepts disclosed show different embodiments of medical devices that incorporate therapeutic lighting. This light can use wavelengths of light that are effective in reducing viral, bacterial or other potential pollutant/infectant counts such as mold or fungi and other pathogens like protozoa and worms. The therapeutic light can be selected from the group of light sources that consists of UV light, UV-C light, Far UV-C light, infrared light, near-infrared light, low level laser light, and White light. The power source can be housed within an interior cavity of the body or it can be housed external to or remote from the body. Internal power sources can be selected from a group of power sources that include but are not limited to thin-cell, coin-cell, rechargeable, and other types of batteries. External power sources can include wired wall power from an outlet, an external battery pack, or other power sources.

The light source includes at least one light source associated with a printed circuit board that is supported within the device wherein the light source is preferably an LED. The light source could also comprise at least one laser diode or other therapeutic light source. A control circuit is operatively associated with the printed circuit board so that the power source and/or light source can be activated and deactivated via a button, a switch or some other mechanism. The control circuit may include a further function to measure treatment duration or indicate that a predetermined treatment period has been completed. By having the therapeutic light work continually, the HCP is able to be active without requiring stoppages. By using more targeted and intermittent therapies, the HCP is able to more precisely target potential sources of infection and avoid overexposure to patient tissue.

In addition, an added utility of the devices may be concomitant visible lighting to improve illumination alongside therapeutic light within the same device. This could be achieved either by intersplicing visible light LEDs with light treatment (UV, e.g.) LEDs, or having separate lighting areas on the same device. A device may have a switch to activate the visible light separately from the therapeutic light or both may be controlled via the same switch.

A therapeutic light assembly for reducing a patient's viral load includes a housing containing at least one therapeutic light source configured to direct light the patient's airway or path of exhaled gas, a power source coupled to the at least one therapeutic light source, and a tubing attachment coupled to the housing configured to secure the housing to a patient's tubing.

The patient's tubing can include intubation tubing or nasal cannula. The housing can be coupled to a headset for attaching to a patient's head, wherein the headset may be anchored to the patient's head via a strap, a plurality of face pads coupled to an arched headset base, or other means. The headset can be configured to be positioned below a nose of the patient.

The housing can include a first panel and a second panel wherein the first panel includes a plurality of inward pointing ribs for positioning the therapeutic light source within the housing. The at least one therapeutic light source can be positioned via directed assembly with openings in the housing, glue or other fixation methods, or other means. The tubing attachment can be coupled to the housing by a pair of spacing ribs. The spacing ribs may be configured to a specific distance to optimize effectiveness of the therapeutic light. The housing can includes an opening to allow the therapeutic light to shine there through directed towards the tubing attachment. The device may include an optical lens for directing the therapeutic light.

The tubing attachment can be rotatable about an axis. The tubing attachment can be rotatable within a plane parallel to a plane defined by the housing. Rotating may allow improved comfort to the patient and improved directing of the therapeutic light. The energy source can be a battery housed within the first cover. The therapeutic light source can include a plurality of LEDs or other light source controlled by a printed circuit board within the housing and can be selected from a group include UV lights, UV-C lights, Far UV-C lights, infrared lights, near infrared lights, low level laser lights, and White light. The therapeutic light source can include a plurality of light sources arranged circumferentially about the housing. The housing can be disposed within the patient's tubing. The tubing attachment can be rigidly attached to the housing or the tubing attachment can be arranged coplanar with a plane defined by the housing. The therapeutic light source can be integrated into a facemask.

These and other features of the devices and systems of the subject invention will become more readily apparent to those having ordinary skill in the art to which the subject invention appertains from the following brief description of the drawings and the drawings themselves.

BRIEF DESCRIPTION OF THE DRAWINGS

So that those skilled in the art will readily understand how to make and use the devices and systems of the subject invention without undue experimentation, preferred embodiments thereof will be described in detail herein below with reference to the figures wherein:

FIG. 1 shows an isometric view of a therapeutic light arc configured to create arena style lighting effects;

FIG. 2 shows a front view of the light arc of FIG. 1;

FIG. 3 shows a front view of the light arc of FIG. 1;

FIG. 17 shows a therapeutic light arc with smoke evacuation features;

FIG. 18 shows a front view of the therapeutic light arc of FIG. 17;

FIG. 19 shows a side view of the therapeutic light arc of FIG. 17;

FIG. 30 shows a top view of the surgical site ring of FIG. 26;

FIG. 31 shows section H-H from FIG. 30;

FIG. 32 shows an enlarged view J from FIG. 31;

FIG. 46 shows an exploded isometric view of the therapeutic lights of FIG. 40;

FIG. 47 shows a top view of the therapeutic lights of FIG. 40;

FIG. 48 shows a sectional view of the therapeutic lights along line K-K from FIG. 43;

FIG. 49 shows an enlarged view N taken from FIG. 47;

FIG. 50 shows a sectional view along line M-M taken from FIG. 45;

FIG. 51 shows an enlarged view L taken from FIG. 44;

FIG. 52 shows an isometric view of a nasal insert and a rear lighting plate component of the therapeutic lights integrated into a nasal cannula assembly of FIG. 40;

FIG. 53 shows a bottom view of nasal insert and rear lighting plate component of the therapeutic lights of FIG. 40;

FIG. 54 shows a bottom, side, and top view of nasal insert and rear lighting plate component of the therapeutic lights of FIG. 40;

FIG. 55 shows a bottom, side, and top view of nasal insert and rear lighting plate component of the therapeutic lights of FIG. 40;

FIG. 56 shows an isometric view of a wire holder component of the therapeutic lights of FIG. 40;

FIG. 57 shows an isometric view of a PCB of the therapeutic lights of FIG. 40;

FIG. 58 shows an isometric view of a therapeutic light surgical site ring for open surgery;

FIG. 59 shows a front view of the therapeutic light surgical site ring of FIG. 58;

FIG. 60 shows a side view of the therapeutic light surgical site ring of FIG. 58;

FIG. 61 shows an isometric exploded view of the therapeutic light surgical site ring of FIG. 58;

FIG. 62 shows a sectional view s of the therapeutic light surgical site ring of FIG. 58 along line R-R taken from FIG. 63;

FIG. 63 shows a top view of the therapeutic light surgical site ring of FIG. 58;

FIG. 64 shows an isometric view of the therapeutic light surgical site ring of FIG. 58 when an outside housing and cover plate are removed;

FIG. 65 shows an enlarged view P taken from FIG. 62;

FIG. 66 shows an isometric view of inside body of the therapeutic light surgical site ring of FIG. 58;

FIG. 67 shows an isometric view of a PCB of the therapeutic light surgical site ring of FIG. 58 with a UV LED;

FIG. 67C is an isometric view of the light ring for open and laparoscopic surgery installed around a laparoscopic trocar/access port in a patient undergoing surgery

FIG. 104 shows rear view of the PCB of the therapeutic light of FIG. 84;

FIG. 105 shows a ventilator tube before installing the attachable therapeutic light of FIG. 84;

FIG. 106 shows a ventilator tube after installing the attachable therapeutic light of FIG. 84;

FIG. 106A shows the attachable therapeutic light of FIG. 84 for installing onto ventilator tube;

FIG. 106B shows the attachable therapeutic light of FIG. 84 for installing onto ventilator tube;

FIG. 107 shows therapeutic lights integrated into a tracheotomy tube;

FIG. 108 shows a front view of a PCB of the lights of FIG. 107;

FIG. 109 shows a side view of intermediate tubing of FIG. 107;

FIG. 110 shows an isometric view of the tracheotomy tubing of FIG. 107;

FIG. 111 shows a side view of the PCB of FIG. 107;

FIG. 112 shows an isometric view of a battery component of FIG. 107;

FIG. 113 shows a rear view of the PCB of FIG. 107;

Figure 107:
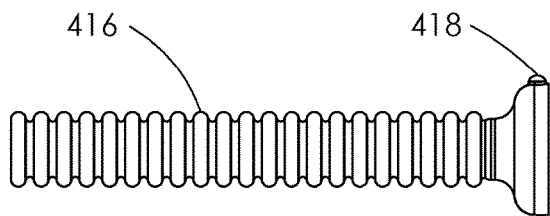
Figure 108:
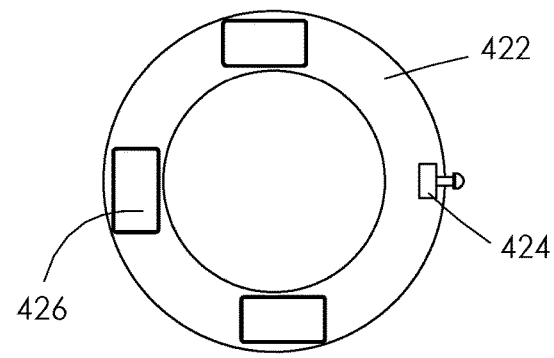
Figure 109:
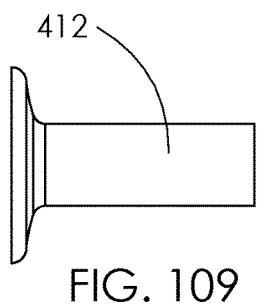
Figure 110:
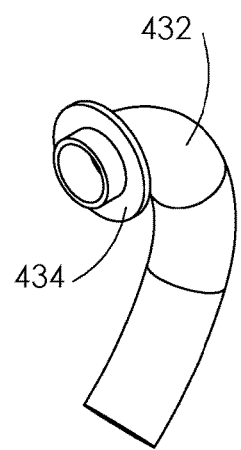
Figure 111:
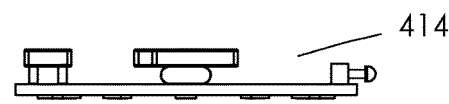
Figure 112:
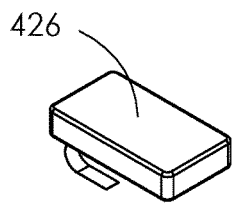
Figure 113:
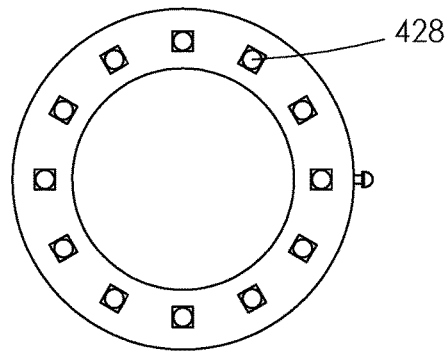
Figure 114:
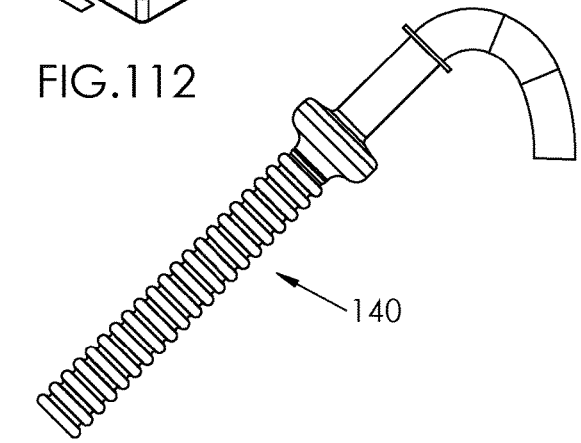
Figure 115:
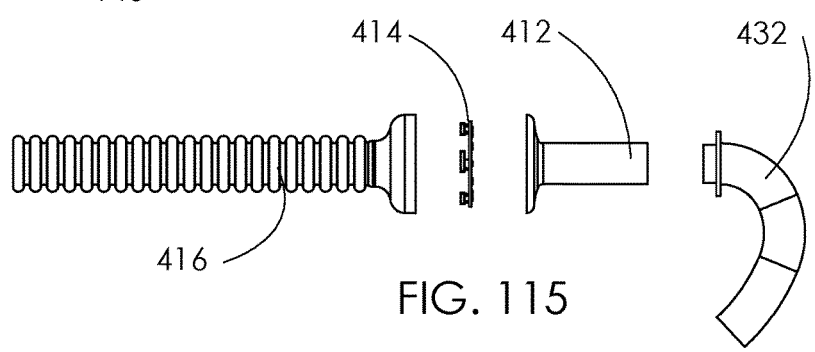
Figure 115A:
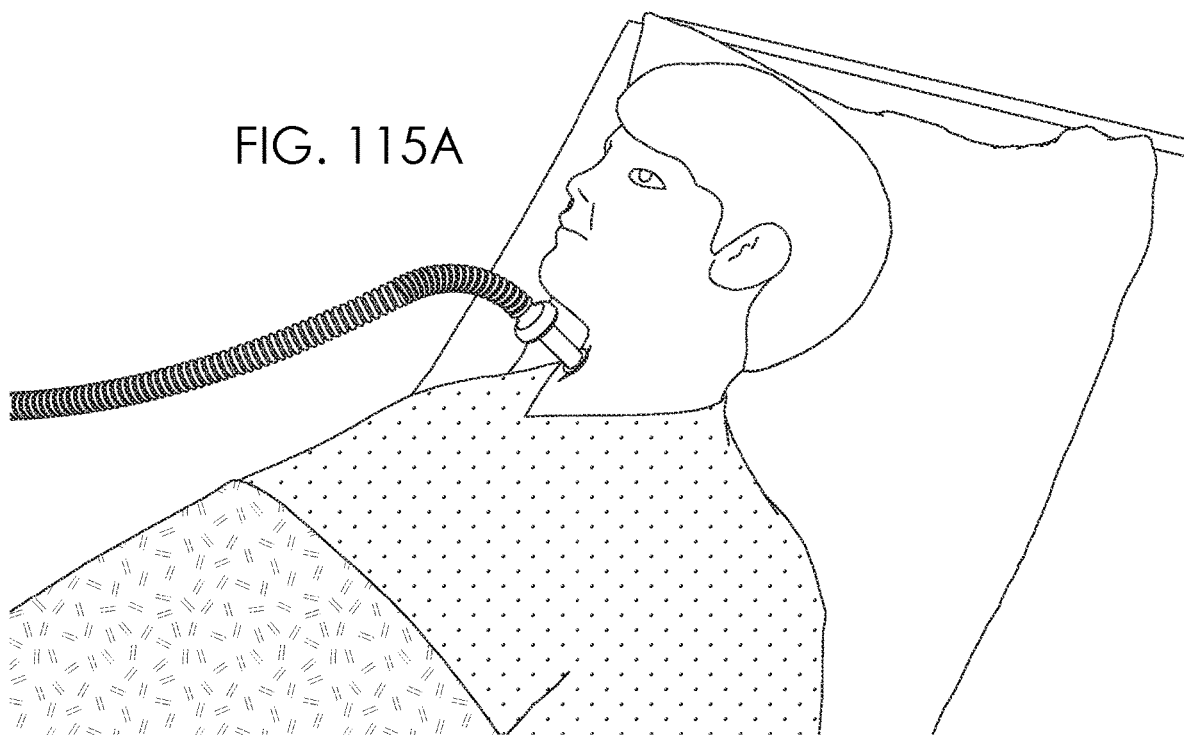
Figure 115B:
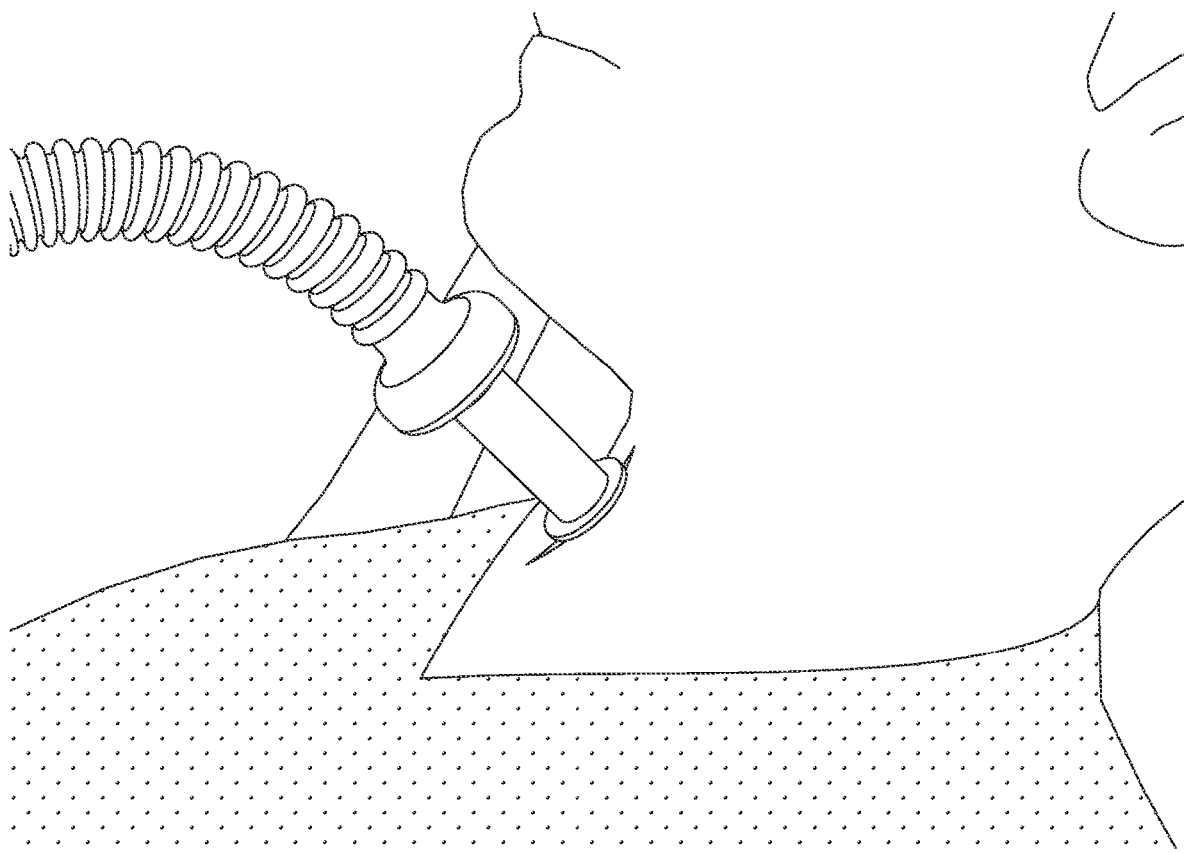
Figure 125A:
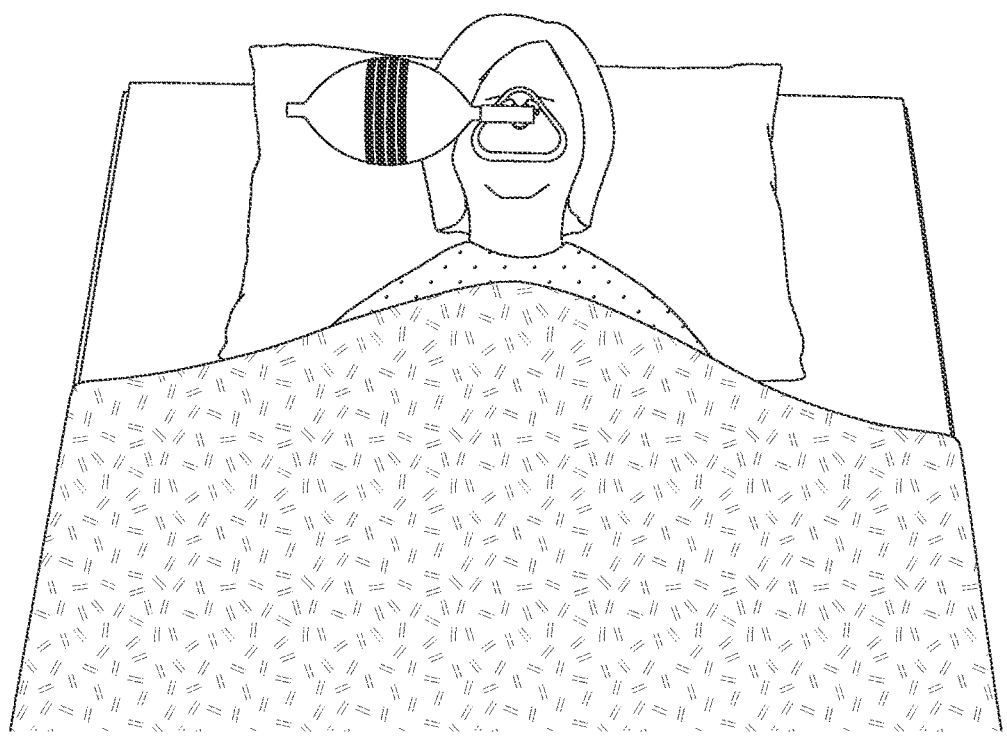
Figure 125B:
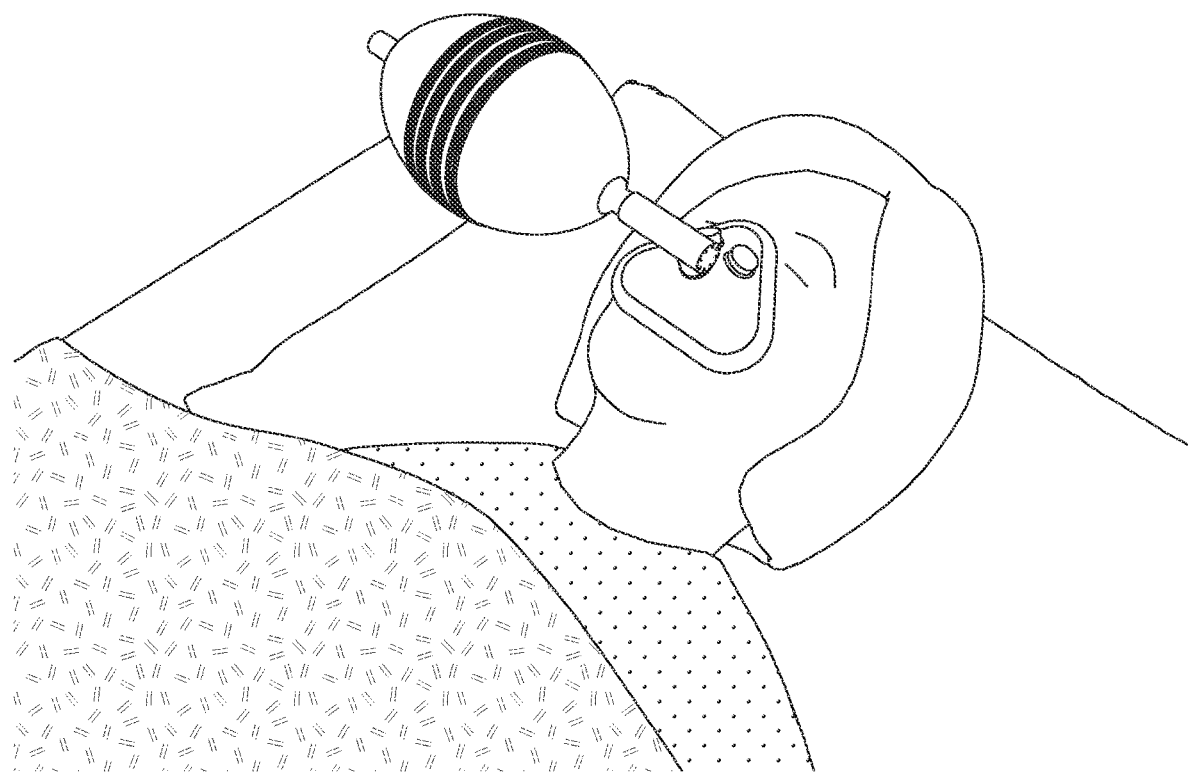
Figure 126:
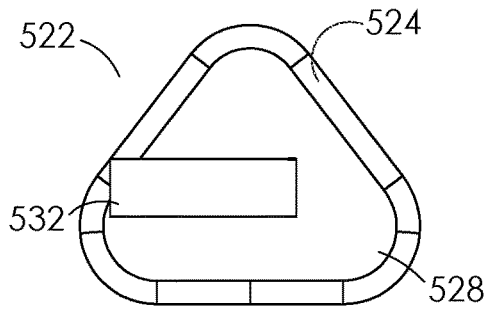
Figure 127:
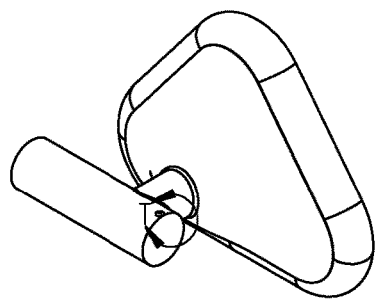
Figure 128:
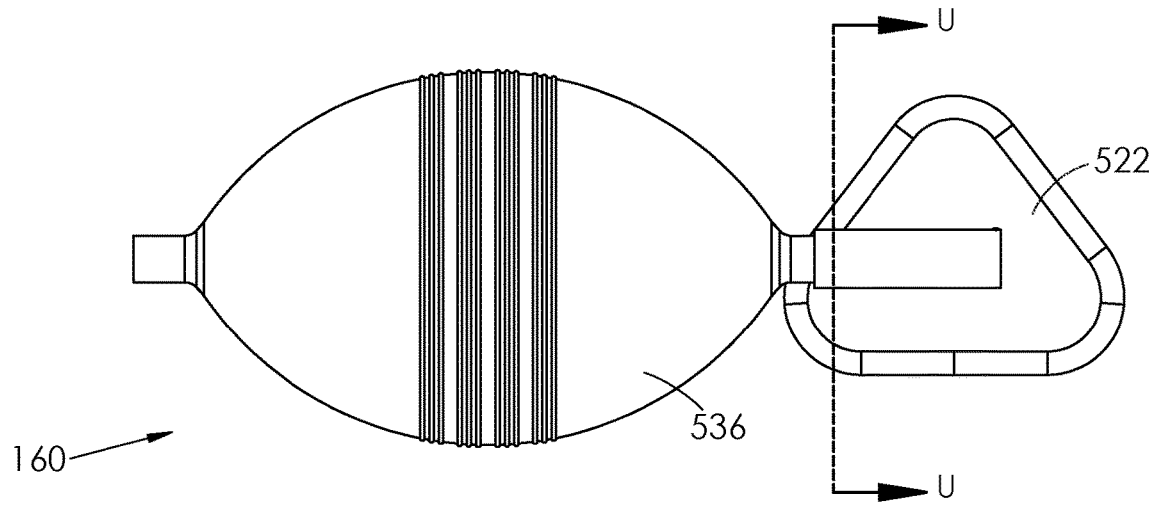
Figure 129:
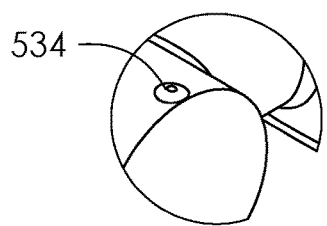
Figure 130:
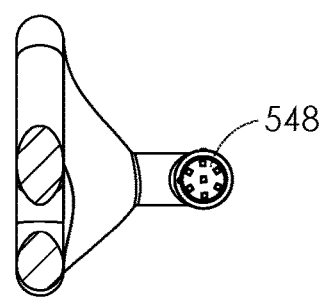
Figure 135:
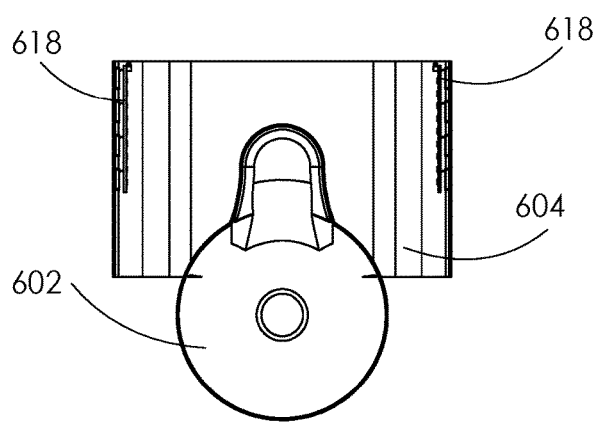
Figures 136, 137:
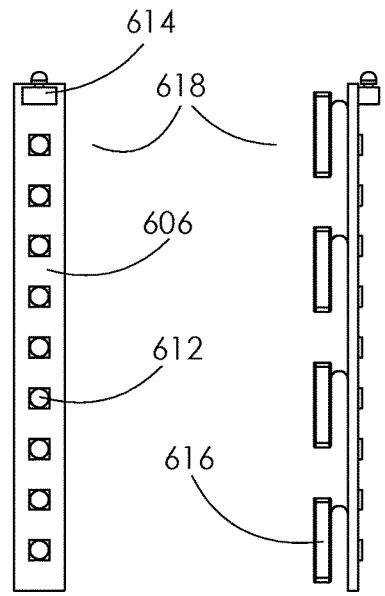
Figure 138:
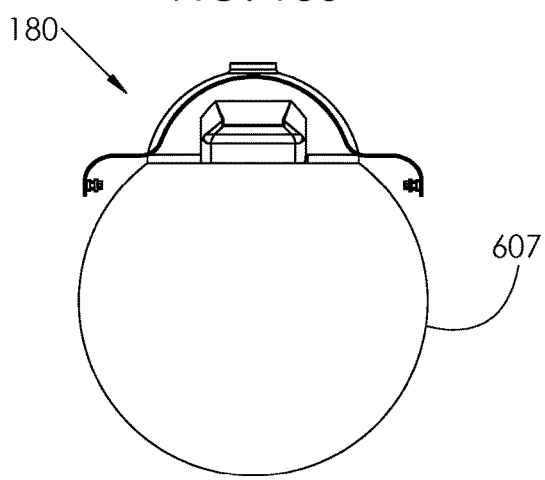
Figure 139:
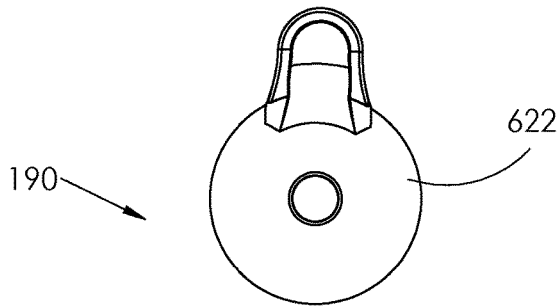
Figure 140:
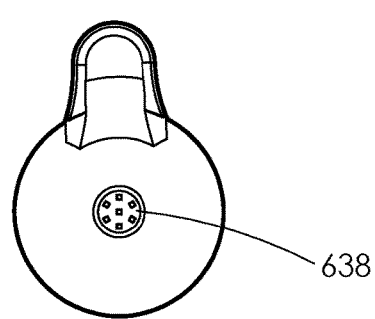
Figure 140A:
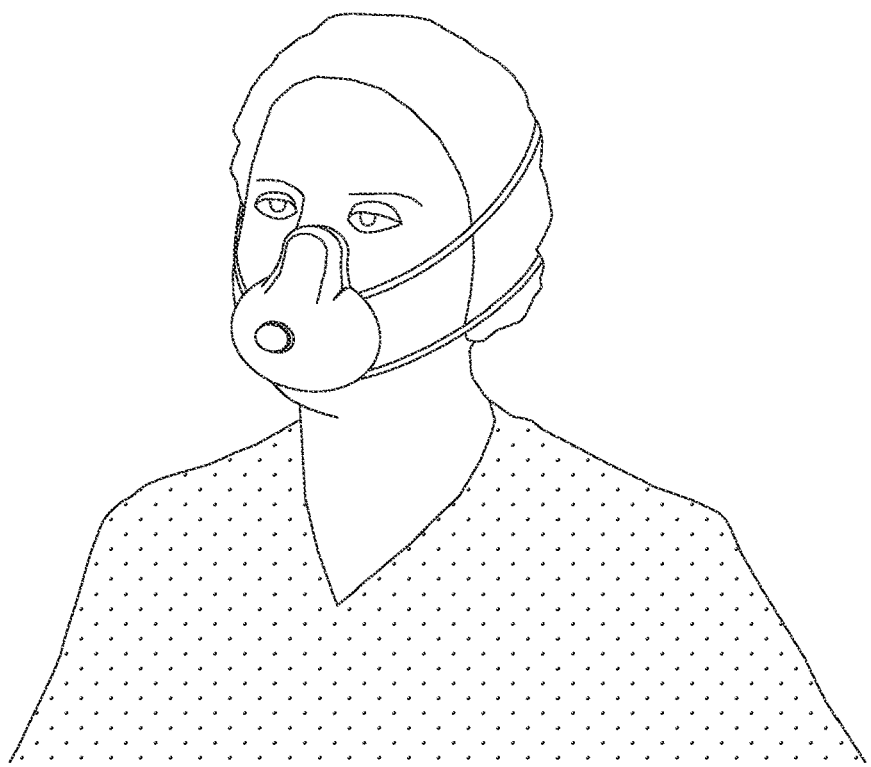
Figure 140B:
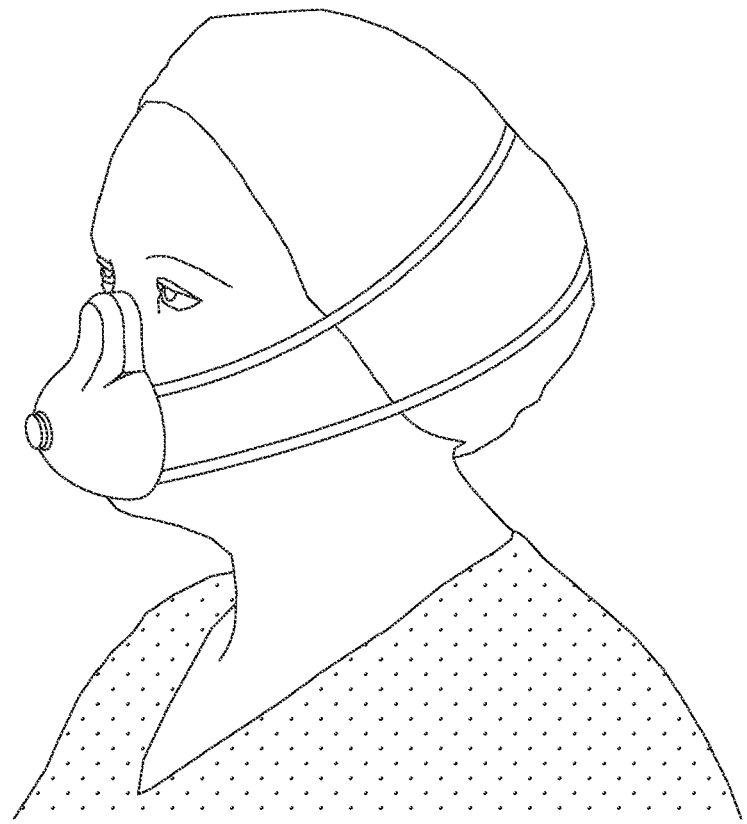

FIG. 114 shows a side view of therapeutic light integrated into tracheotomy tube FIG. 115 shows an exploded view of the therapeutic light of FIG. 107 integrated into a tracheotomy tube;

FIGS. 115A and 115B show the therapeutic light of FIG. 107 integrated into a tracheotomy tube used on a patient with a tracheotomy in a hospital bed;

FIG. 116 shows a front view therapeutic lighting bag mask ventilation device;

FIG. 117 shows a side view of the therapeutic lighting bag mask ventilation device of FIG. 116;

FIG. 118 shows a front view of a PCB component of the lighting bag mask ventilation device of FIG. 116;

FIG. 119 shows a front view of a PCB component of the lighting bag mask ventilation device of FIG. 116 with a battery installed;

FIG. 120 shows a side view of the PCB of the lighting bag mask ventilation device of FIG. 116;

FIG. 121 shows a rear view of the PCB of the lighting bag mask ventilation device of FIG. 116;

FIG. 122 shows a side view of a battery of the lighting bag mask ventilation device of FIG. 116;

FIG. 123 shows is a rear view of a mask component the lighting bag mask ventilation device of FIG. 116;

FIG. 124 shows a the bag the lighting bag mask ventilation device of FIG. 116;

FIG. 125 shows a front view of the therapeutic lighting mask bag ventilation device assembly of FIG. 116;

FIGS. 125A and 125B show the therapeutic lighting mask bag ventilation device of FIG. 116 used on a patient in a hospital bed;

FIG. 126 shows a front view of a mask component of a therapeutic lighting bag ventilation device;

FIG. 127 shows an isometric view of a mask component of a therapeutic lighting bag ventilation device of FIG. 126;

FIG. 128 shows a front view of therapeutic lighting bag ventilation device assembly of FIG. 126;

FIG. 129 shows an enlarged view T taken from FIG. 127;

FIG. 130 shows section U-U taken from FIG. 128;

FIG. 131 shows a front view of a mask component of a therapeutic lighting mask for ventilator device;

FIG. 132 shows a top view of the therapeutic lighting mask for ventilator device assembly of FIG. 131;

FIG. 133 shows a front view of the therapeutic lighting mask for ventilator device assembly of FIG. 131;

FIG. 134 shows a rear view of the therapeutic lighting mask for ventilator device assembly of FIG. 131;

FIG. 135 shows a therapeutic light personal protective mask for health care providers;

FIG. 136 shows a front view of a PCB of the therapeutic light personal protective mask of FIG. 135;

FIG. 137 shows a side view of a PCB of the therapeutic light personal protective mask of FIG. 135;

FIG. 138 shows a top view of the therapeutic lighting mask of FIG. 135 with integrated face shield assembly;

FIG. 139 shows a front view of the mask component of the therapeutic lighting mask of FIG. 135 with integrated face shield;

FIG. 140 shows a rear view of the mask component of the therapeutic lighting mask of FIG. 135 with integrated face shield; and FIGS. 140A and 140B show a healthcare provider with therapeutic lighting mask device installed.

ENABLING DESCRIPTION OF EMBODIMENTS
OF THE INVENTION

Described below are a set of devices and methods for protecting Health Care Providers (HCPs) via the reduction of viral count, bacteria count, or other potentially infectious or infection-causing agents by applying therapeutic light directed at the source (typically the mouth and nose area of an infectious or potentially infectious patient) to denature, deactivate, kill, or otherwise render harmless a portion of these infectious agents. Therapeutic lights can be used to penetrate and kill viruses suspended in the air without being harmful to humans. Integrating such therapeutic lights to devices such as intubation tubes and masks as well as suction tubing commonly used during surgery as described in detail below can be used to reduce or eliminate the associated viral load, thereby reducing the risk of transmission and infection to HCPs, and other with close contact to affected respiratory droplets, while performing intubations, surgeries, and other similar airway related procedures.

Specifically therapeutic lights include can include UV light, UV-C light, Far UV-C light, infrared light, near infrared light, low level laser light, White light, and other short-wavelength ultraviolet light for germicidal irradiation (UVGI) which damages the DNA in microorganisms. Specifically, UV-C therapy has been noted to promote wound healing as well. Furthermore, UV-C light, has started to prove more useful in the prophylaxis of SSI, with one study revealing a decrease in infection rate from 10% to 0.24% with ultraviolet light therapy. Commercial UV-sterilizing devices most commonly known for consumer disinfection of mobile phones.

Figure 4:
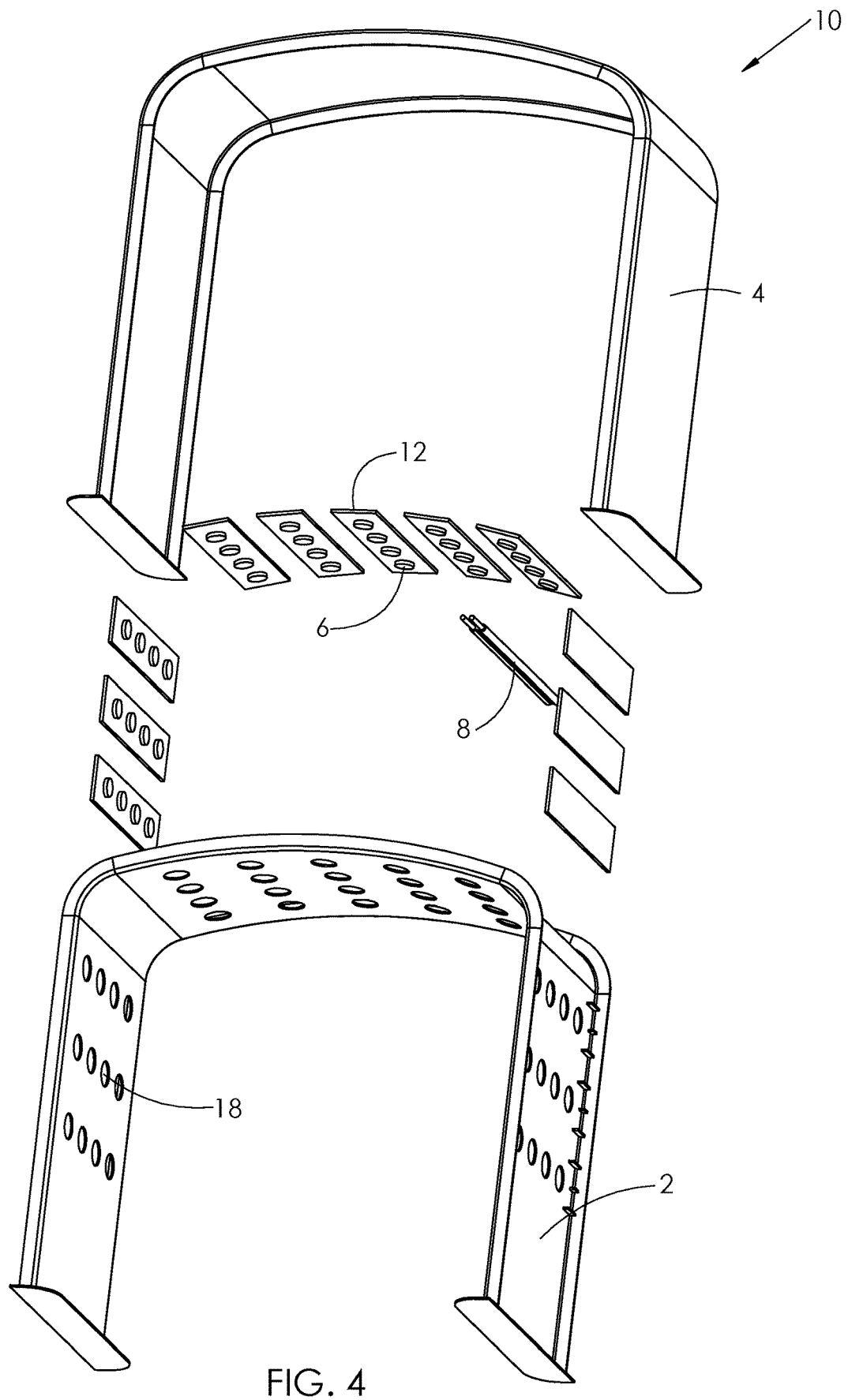
FIG. 4 shows an exploded isometric view of the light arc of FIG. 1.
Figure 5:
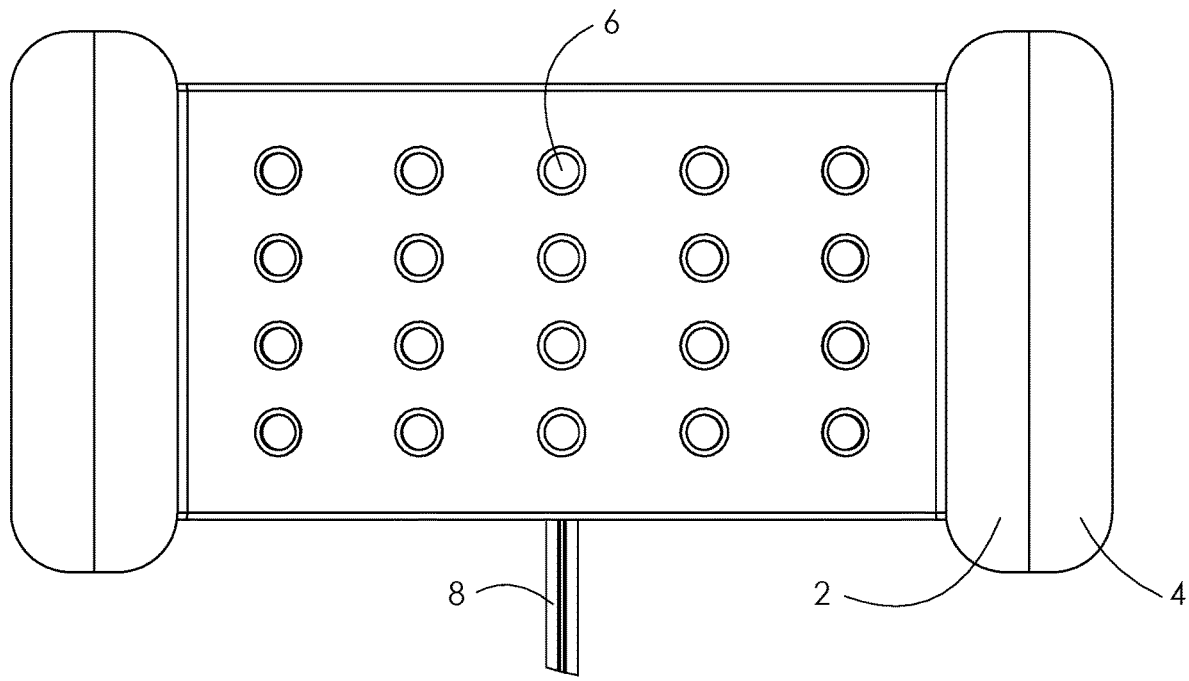
FIG. 5 shows a bottom view of the light arc of FIG. 1.
Figure 6:
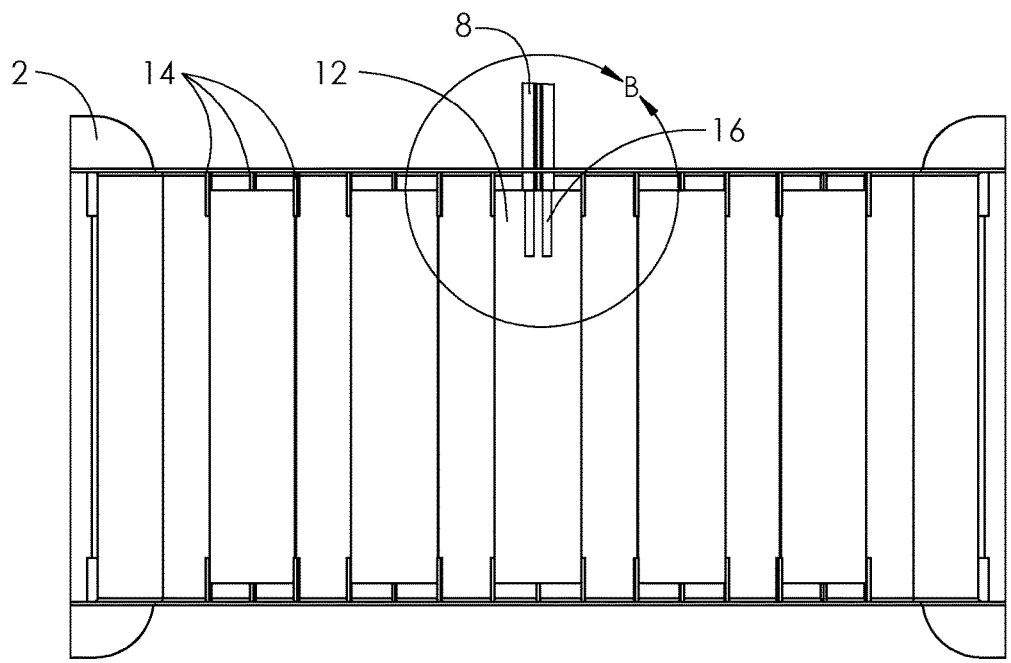
FIG. 6 shows a top view of the light arc of FIG. 1 with a top housing removed.
Figure 7:
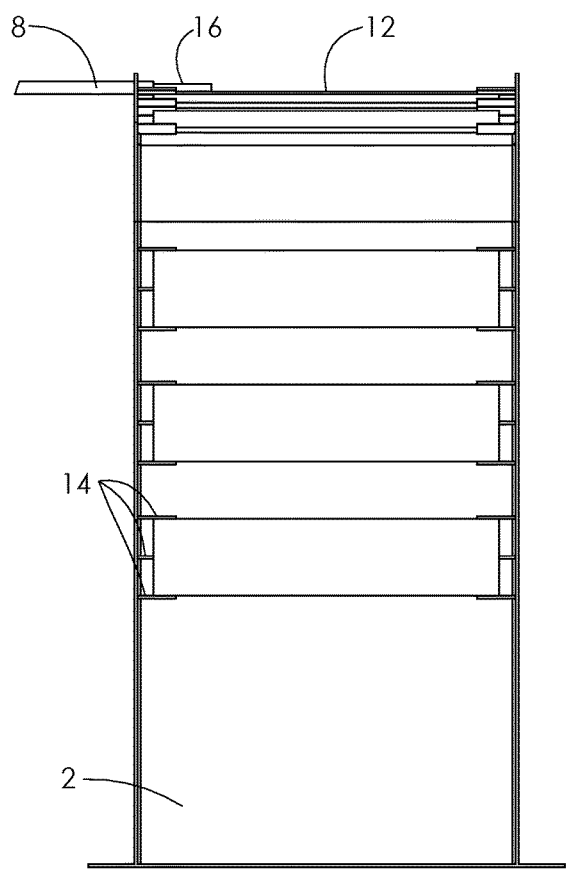
FIG. 7 shows a side view of the light arc of FIG. 1 with the top housing removed.
Figure 8:
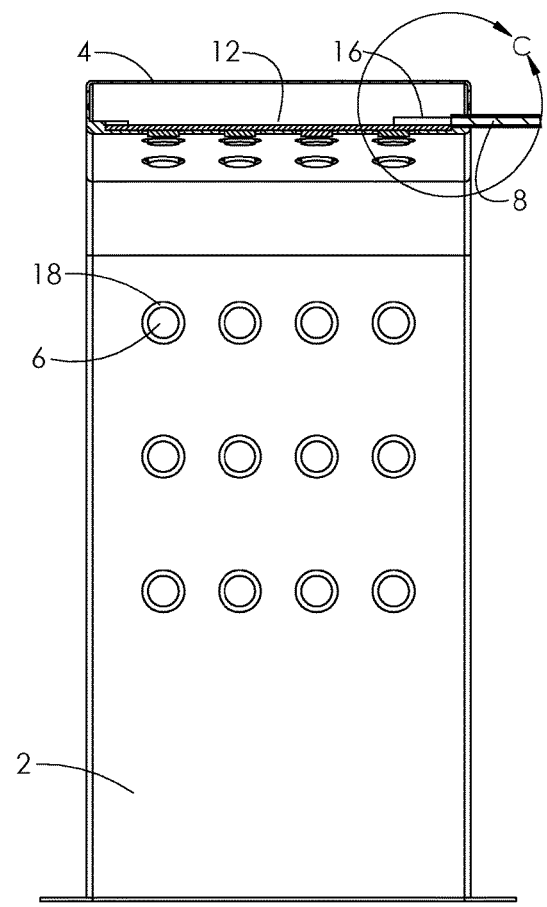
FIG. 8 shows sectional view along A-A taken from FIG. 2
Figure 9:
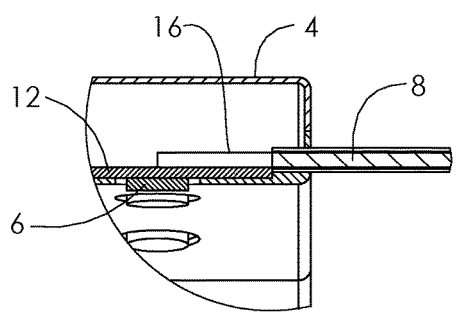
FIG. 9 shows an enlarged view C taken from FIG. 8
Figure 10:
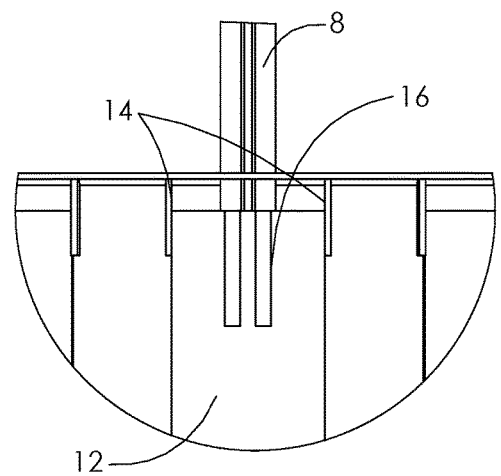
FIG. 10 shows an enlarged view B taken from FIG. 6
Figure 11:
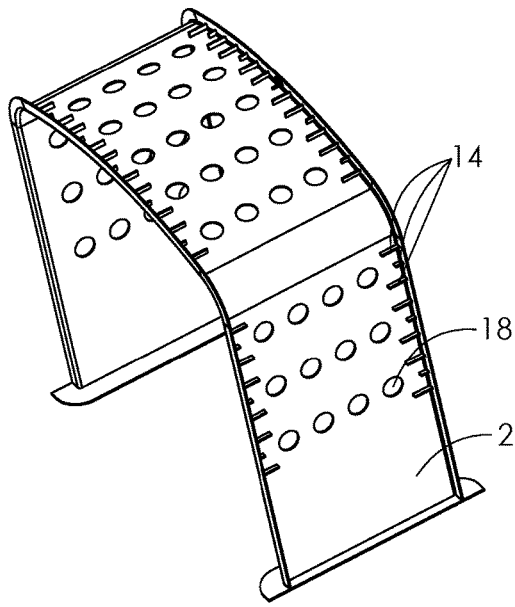
FIG. 11 shows an isometric view of a bottom housing of the light arc of FIG. 1.
Figure 12:
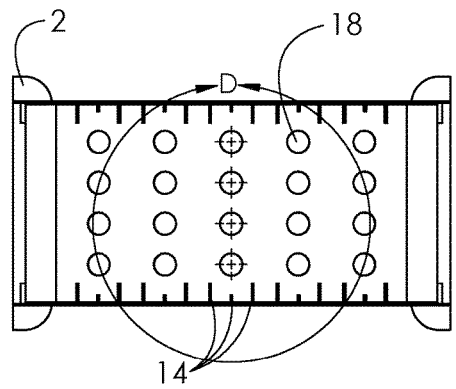
FIG. 12 shows a top view of the bottom housing of the light arc of FIG. 1.
Figure 14:
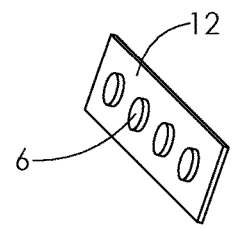
FIG. 14 shows an isometric view of a PCB with a UV LED.
Figure 13:
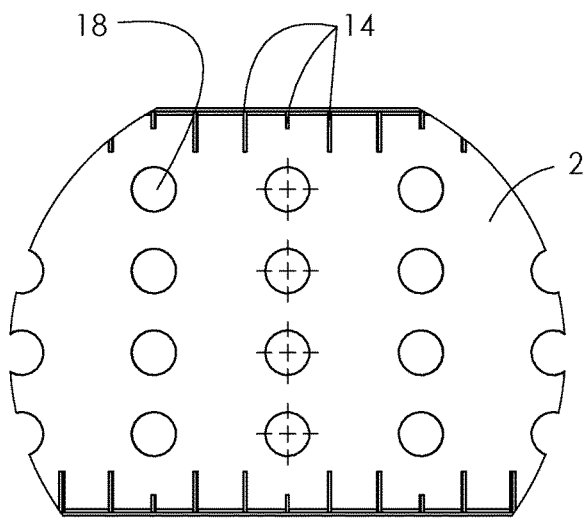
FIG. 13 shows an enlarged view D taken from FIG. 12.
Figure 15:
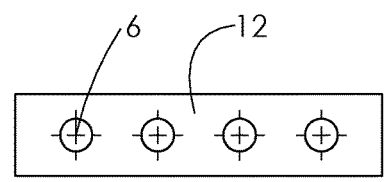
FIG. 15 shows a bottom view of the PCB.
Figure 16:
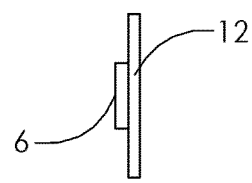
FIG. 16 shows a side view of the PCB.
Figure 16A:
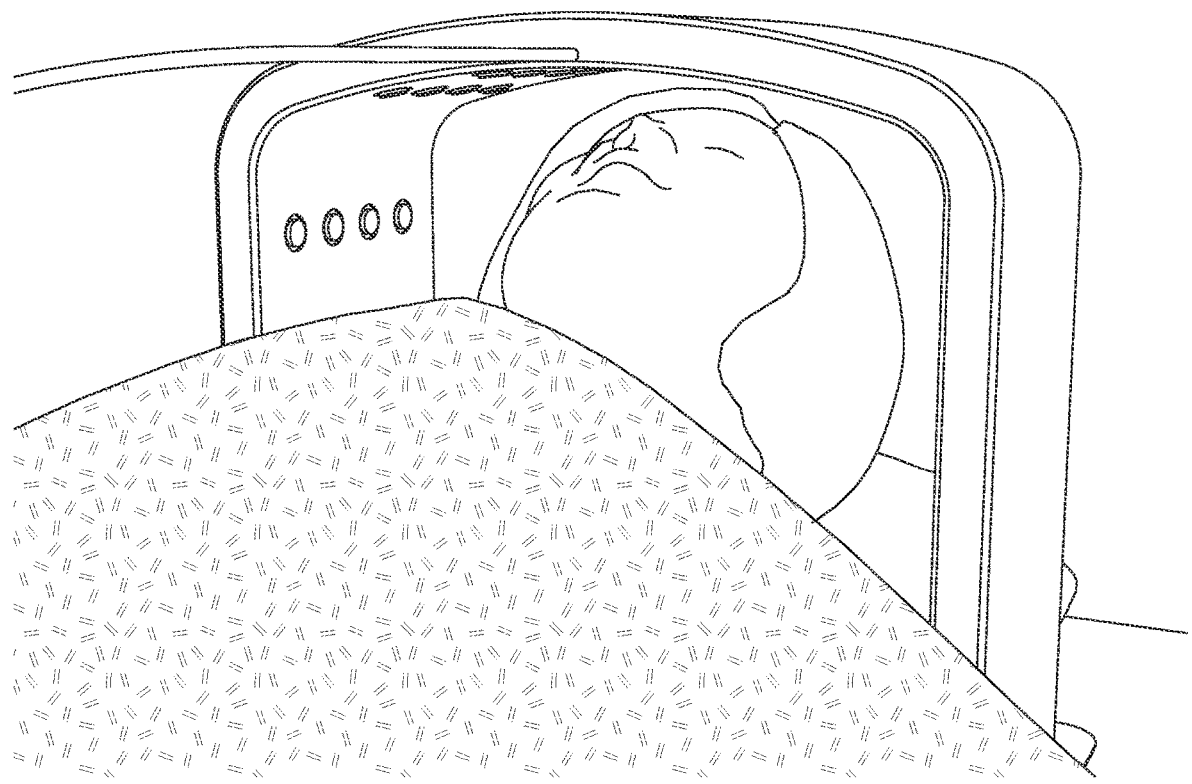
FIG. 16A and FIG. 16B shows therapeutic light arc of FIG. 1 installed onto a hospital bed with patient lying underneath.
Figure 16B:
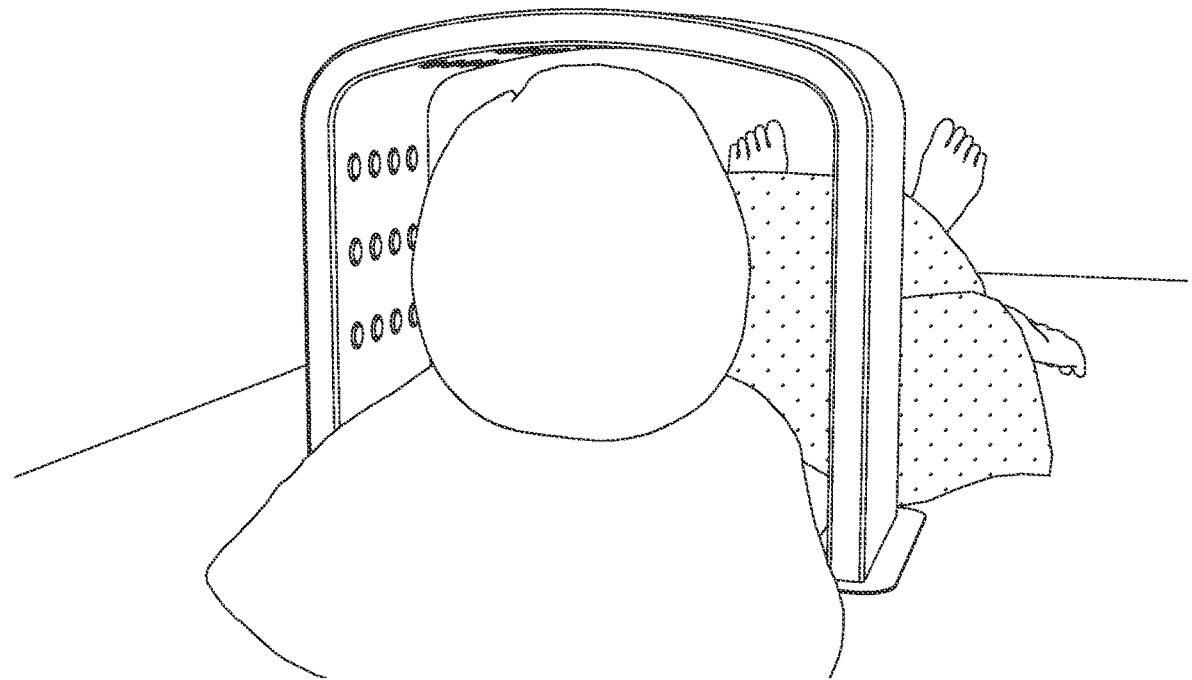
Figure 16C:
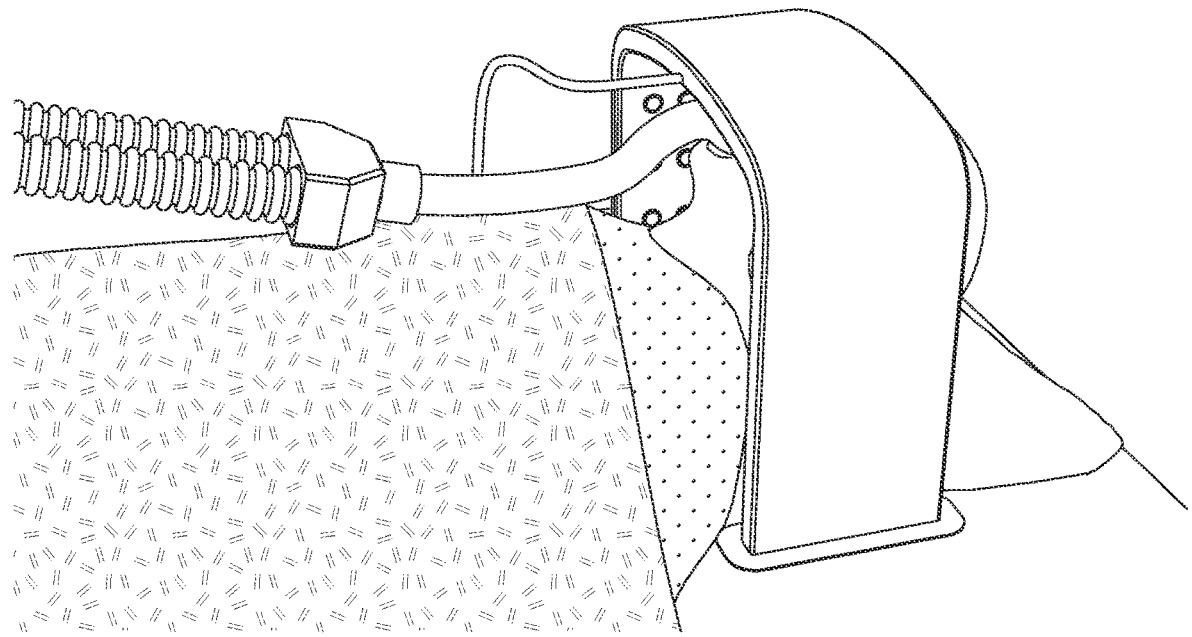
FIG. 16C shows the therapeutic light arc of FIG. 1 installed onto a hospital bed with an intubated patient using ventilator lying underneath.
Figure 16D:
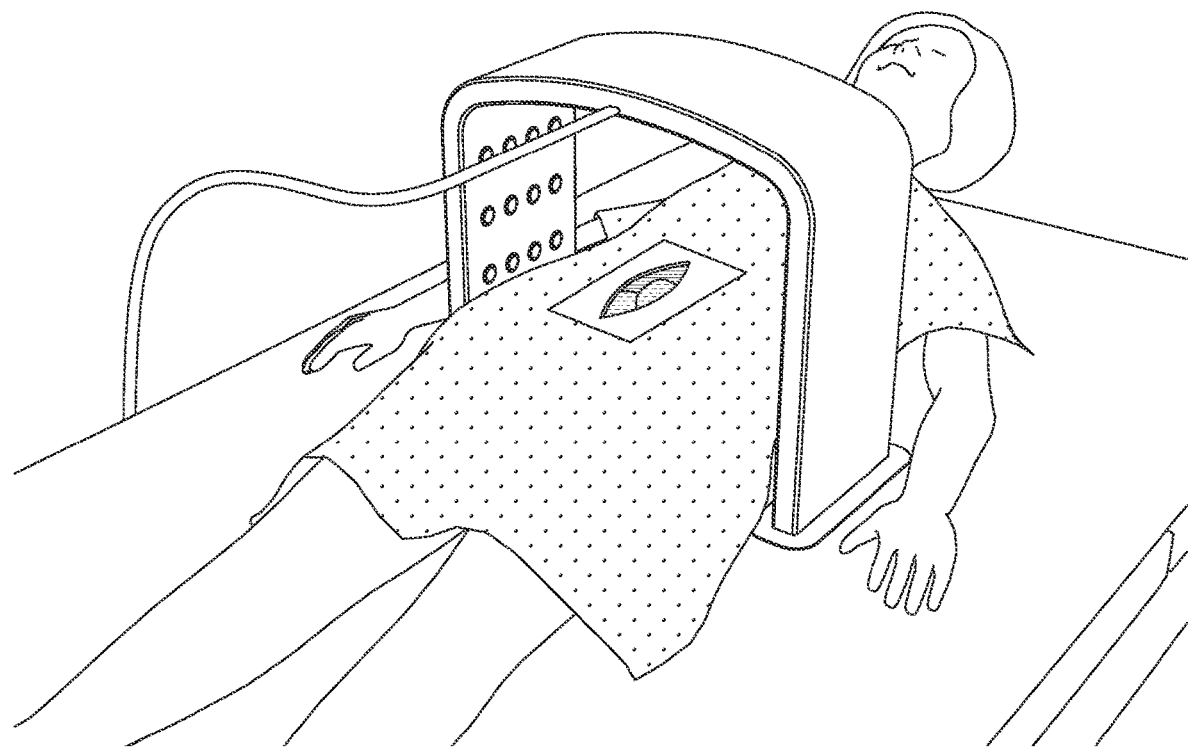
FIG. 16D shows the therapeutic light arc of FIG. 1 installed onto a surgical table while patient is undergoing surgery.
Figure 20:
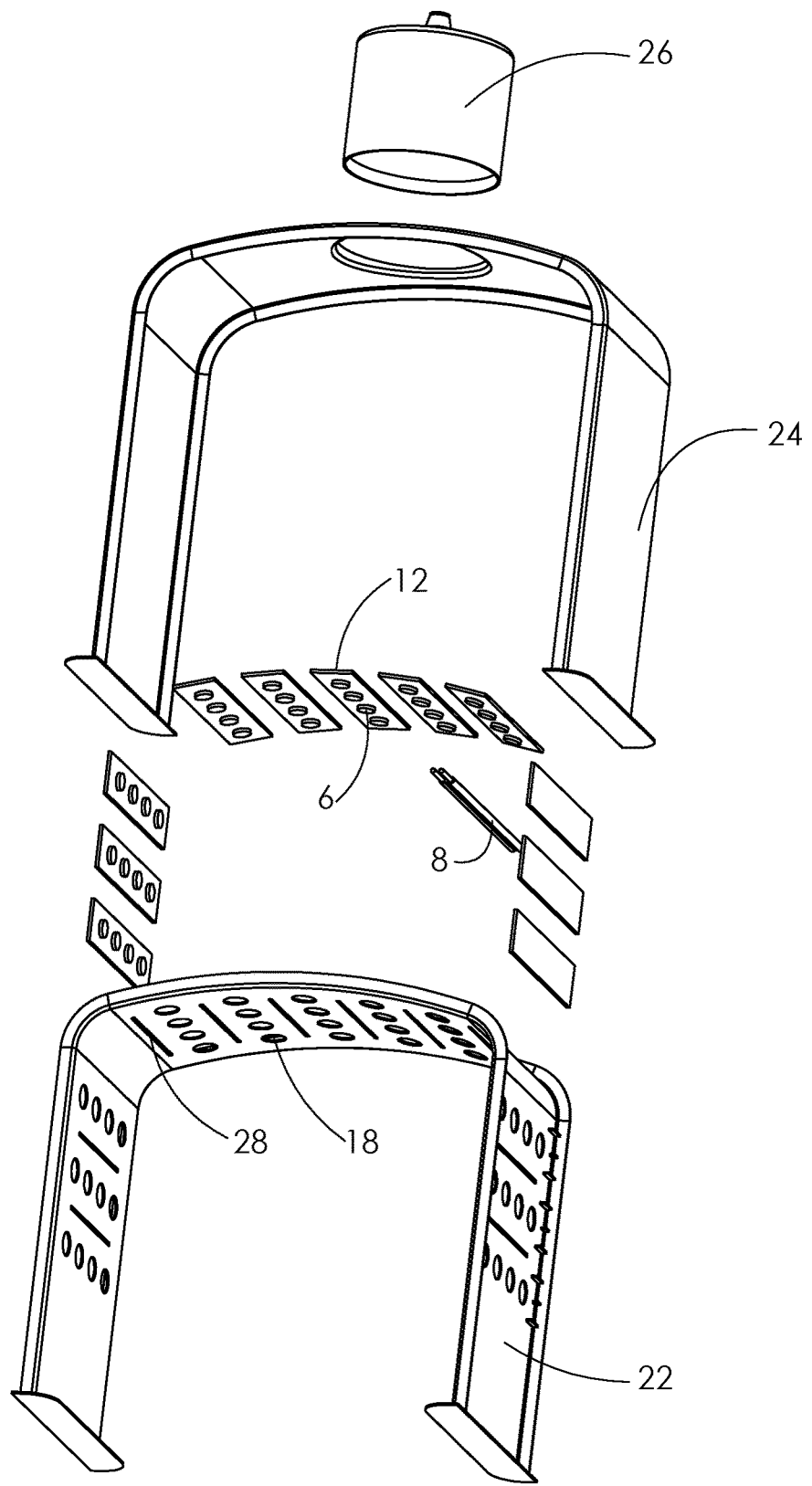
FIG. 20 shows an exploded isometric view of the assembly of the light arc of FIG. 17.
Figure 21:
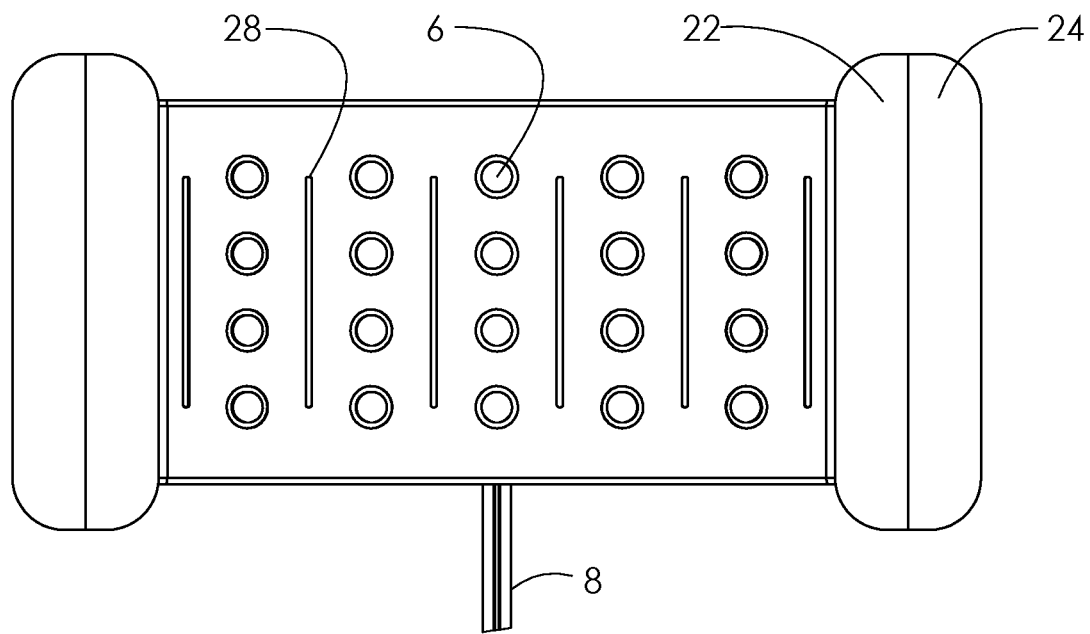
FIG. 21 shows a bottom view of the light arc of FIG. 17.
Figure 22:
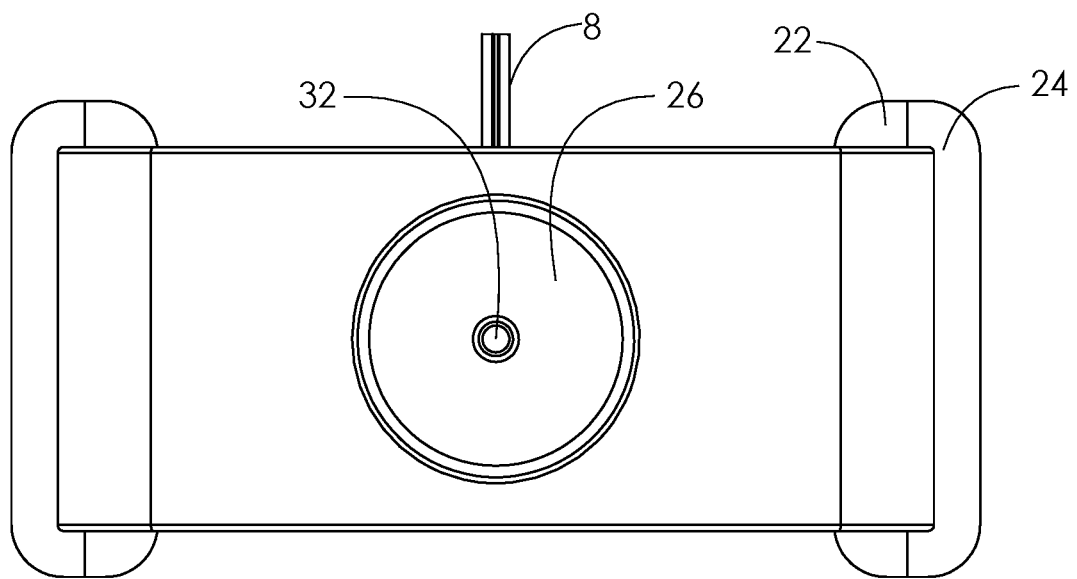
FIG. 22 shows a top view of the light arc of FIG. 17.
Figure 23:
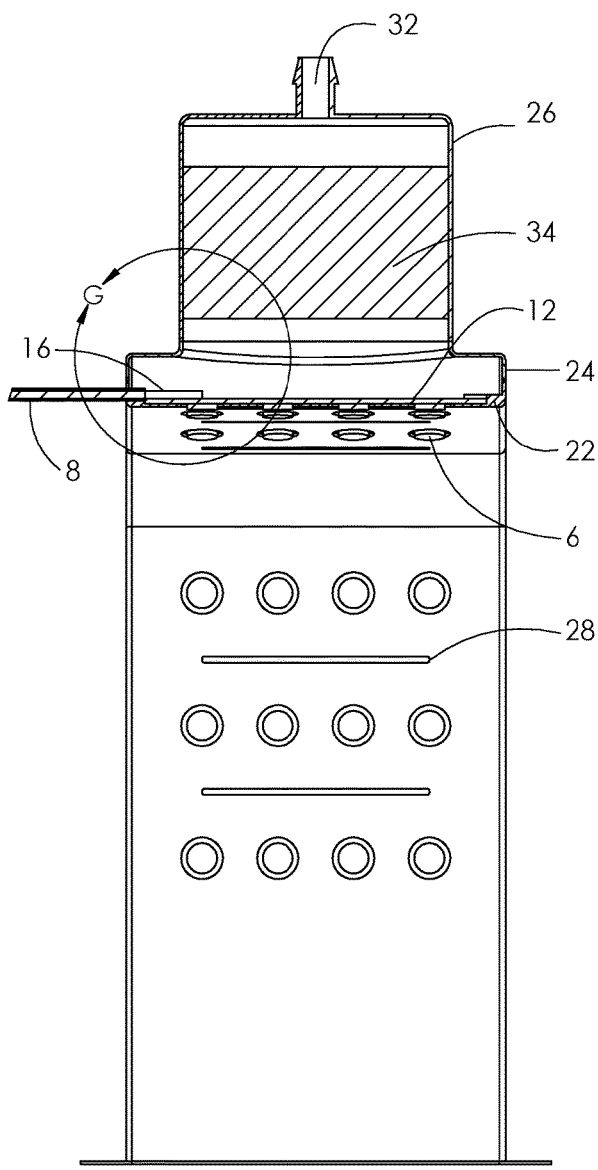
FIG. 23 shows a sectional view E-E taken from FIG. 18.
Figure 24:
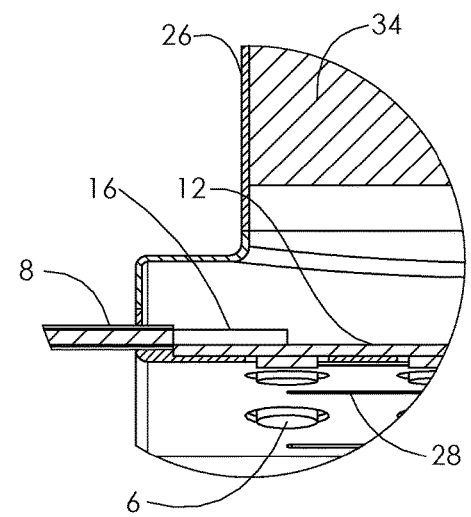
FIG. 24 shows an enlarged view G taken from FIG. 23.
Figure 25:
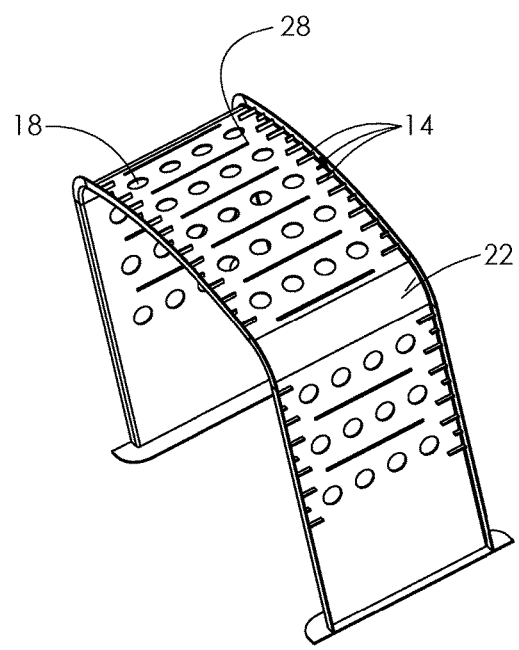
FIG. 25 shows an isometric view of a bottom housing of the light arc of FIG. 17.
Figure 25A:
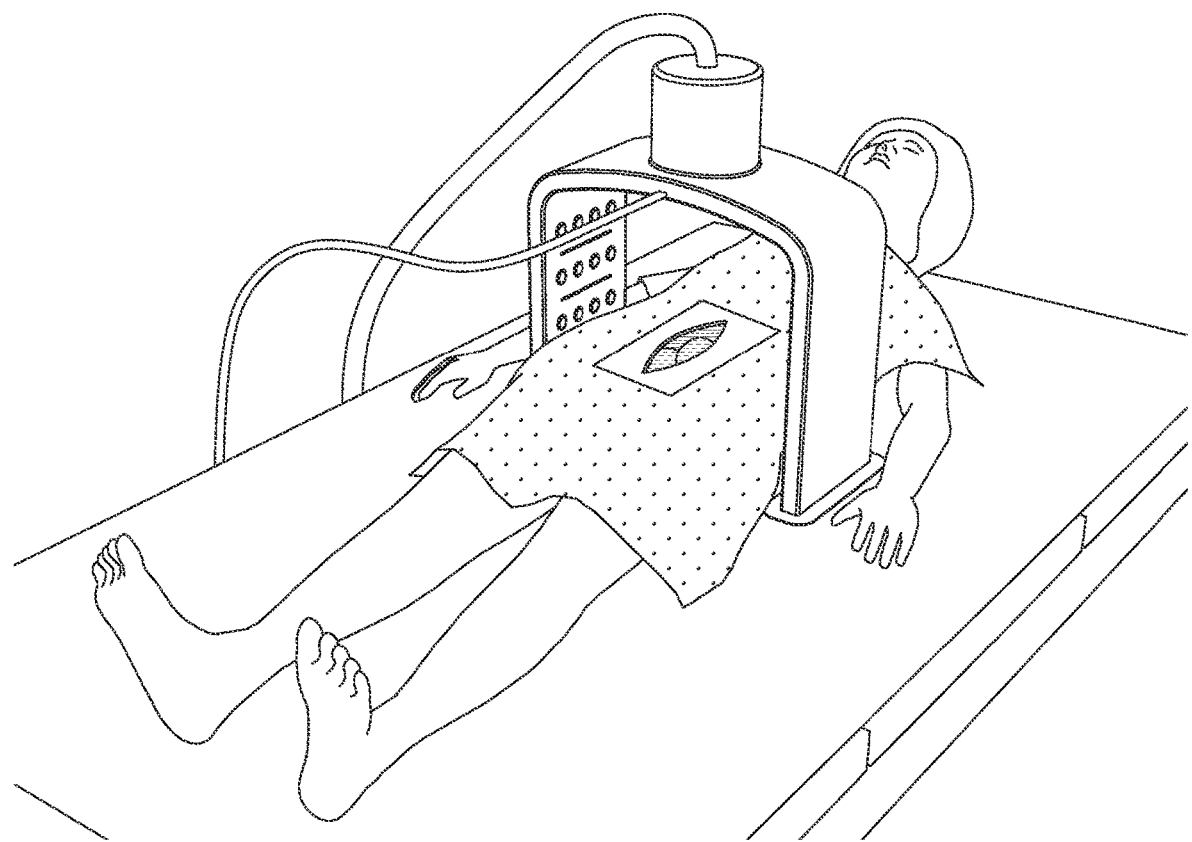
FIG. 25A shows the light arc of FIG. 17 installed on surgical table while patient is undergoing surgery.
Figure 26:
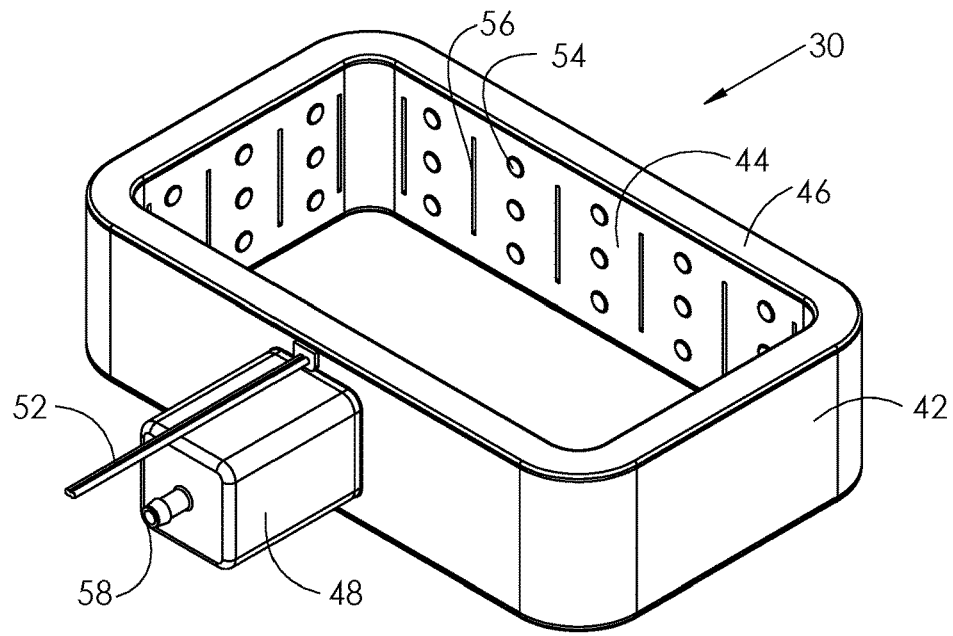
FIG. 26 shows a therapeutic light surgical site ring with smoke evacuation.
Figure 27:
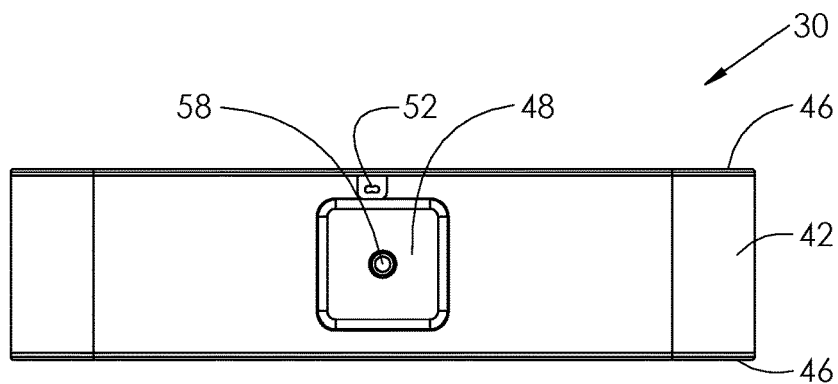
FIG. 27 shows a front view of the surgical site ring of FIG. 26.
Figure 28:
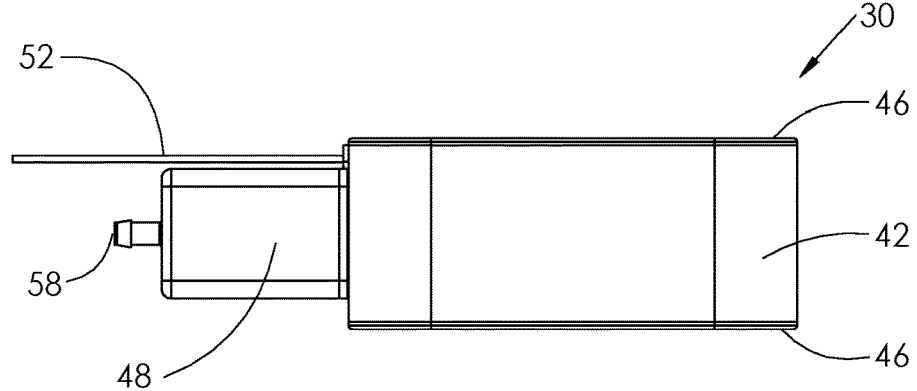
FIG. 28 shows a side view of the surgical site ring of FIG. 26.
Figure 29:
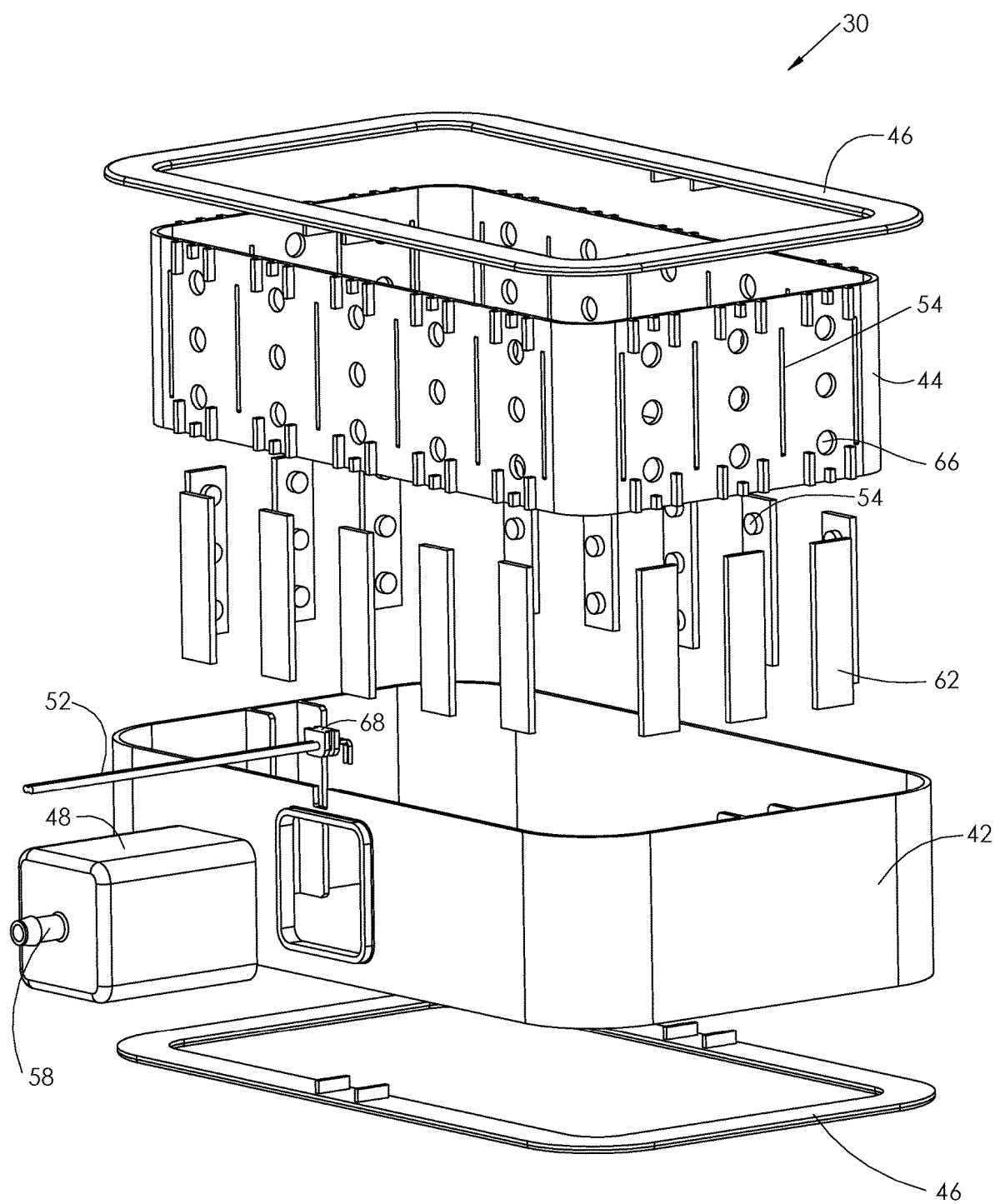
FIG. 29 shows an exploded view of the surgical site ring of FIG. 26.
Figure 33:
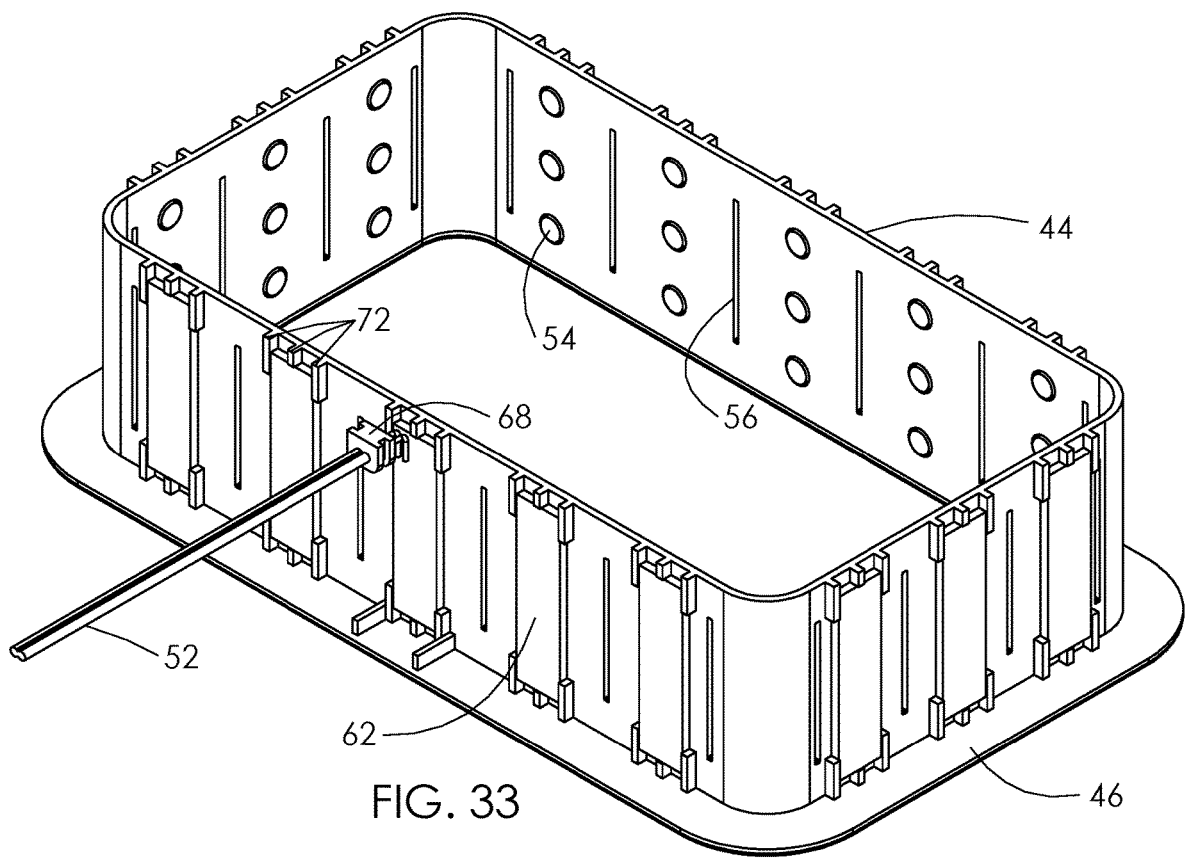
FIG. 33 shows an isometric view the surgical site ring of FIG. 26 with a cover plate and a filter removed.
Figure 34:
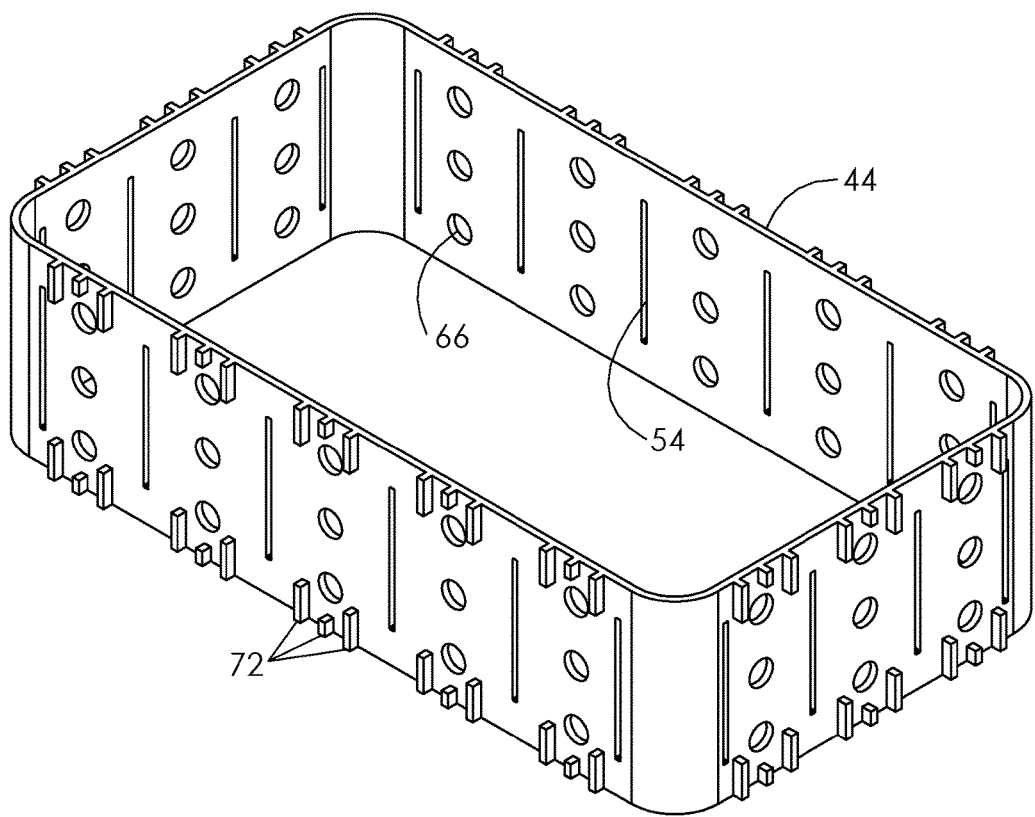
FIG. 34 shows an isometric view of an inside of the surgical site ring of FIG. 26.
Figure 35:
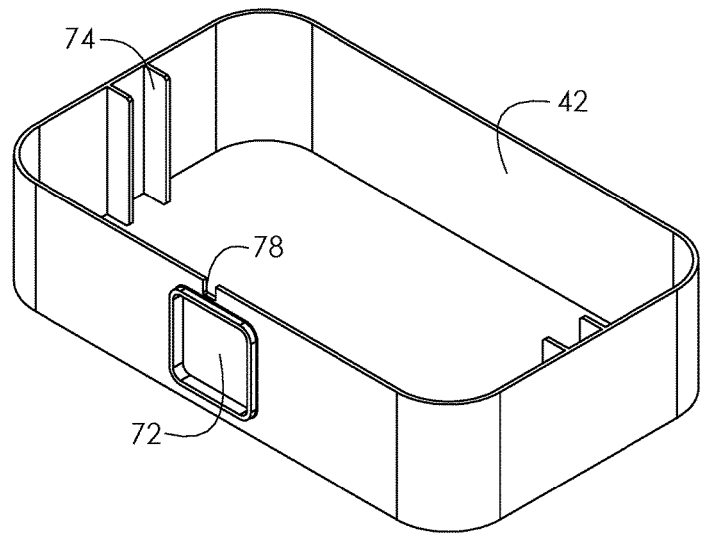
FIG. 35 shows an isometric view of an outside of the housing of the surgical site ring of FIG. 26.
Figure 36:
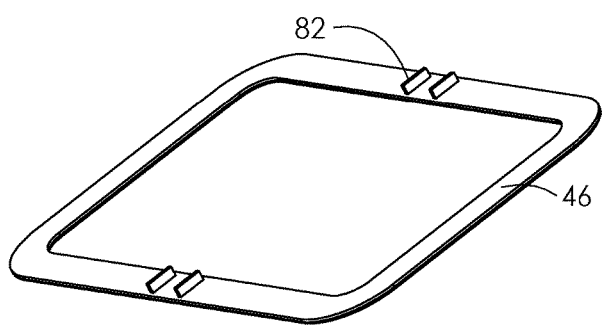
FIG. 36 shows an isometric view of a cover plate of the surgical site ring of FIG. 26.
Figure 37:
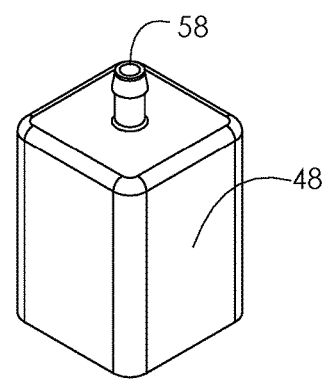
FIG. 37 shows an isometric view of a filter enclosed within a chamber of the surgical site ring of FIG. 26.
Figure 38:
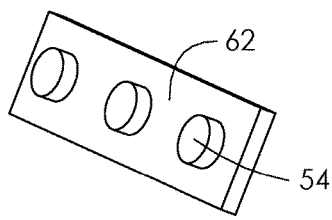
FIG. 38 shows an isometric view of a PCB with a UV LED.
Figure 39:
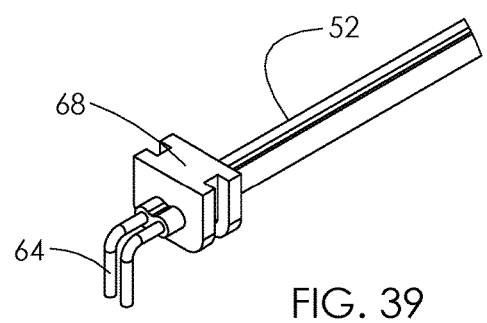
FIG. 39 shows an isometric broken view of an electrical wire and a connector of the surgical site ring of FIG. 26.
Figure 39A:
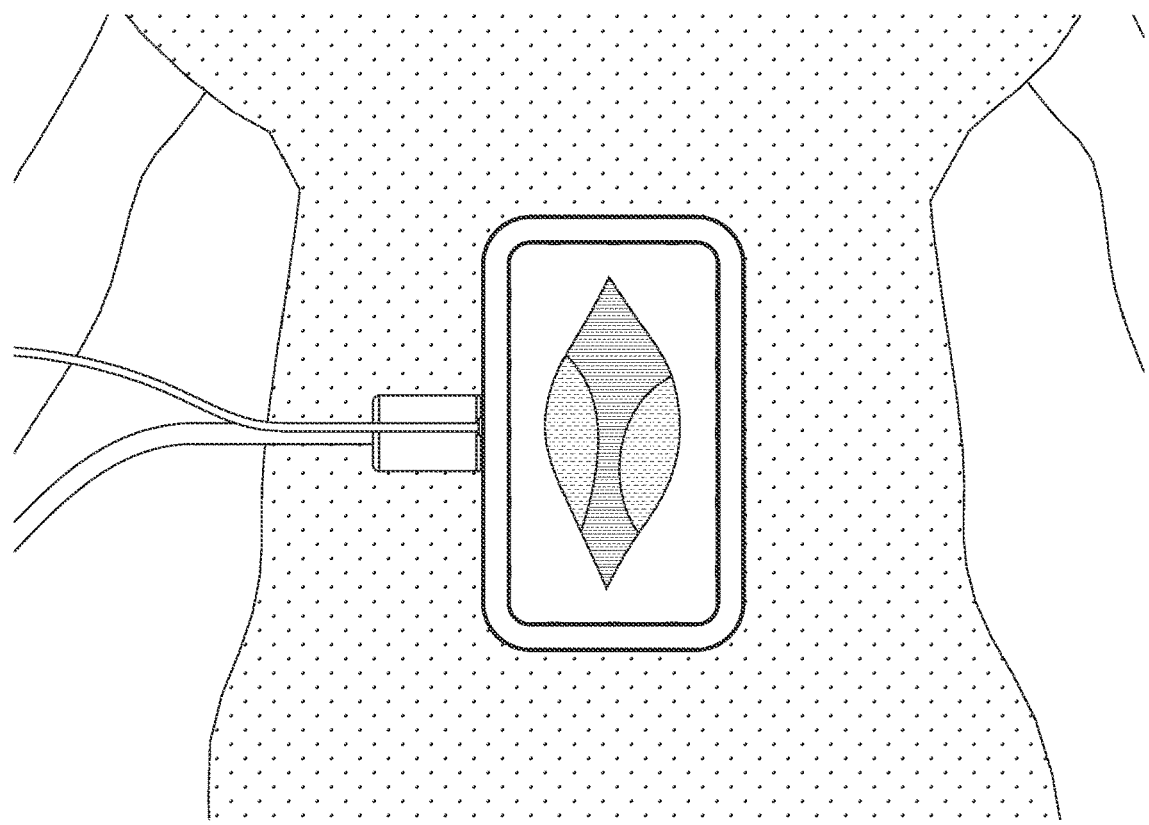
FIG. 39A shows a top view of the light ring of FIG. 26 around a surgical wound on a patient undergoing surgery.
Figure 39B:
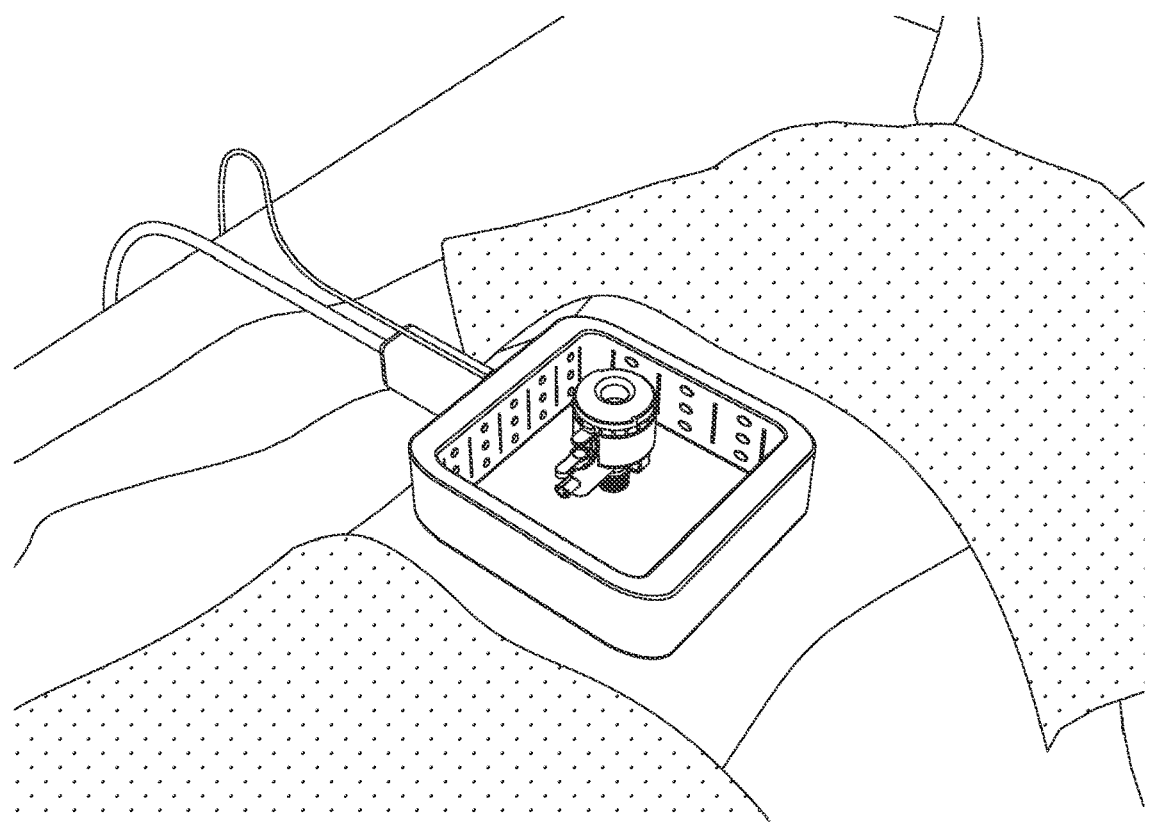
FIG. 39B shows an isometric view of the light ring of FIG. 26 around a laparoscopic trocar/access port in a patient undergoing surgery.
Figure 40:
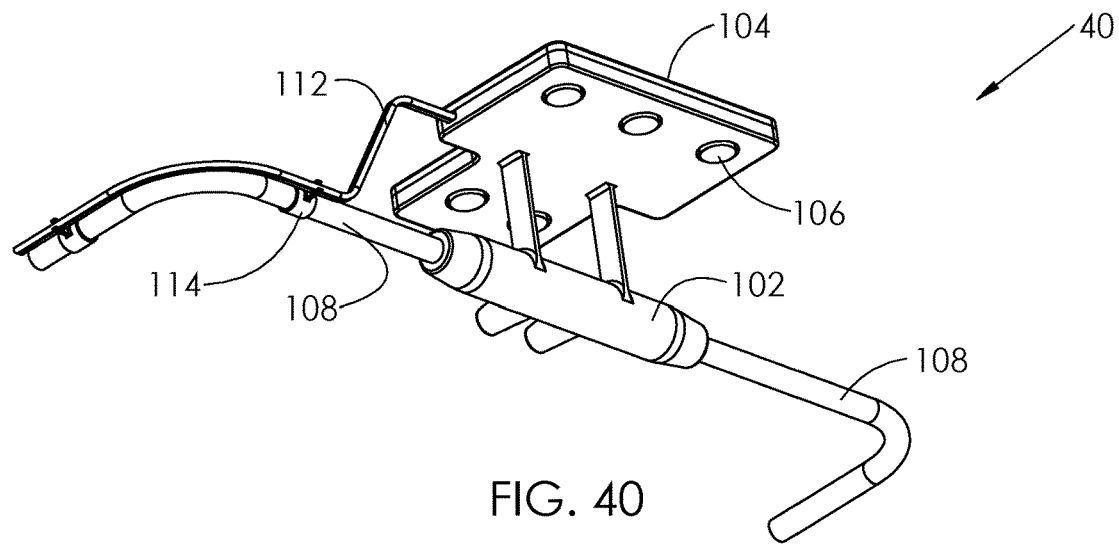
FIG. 40 shows an embodiment having therapeutic lights integrated into a nasal cannula assembly for providing supplemental oxygen.
Figure 41:
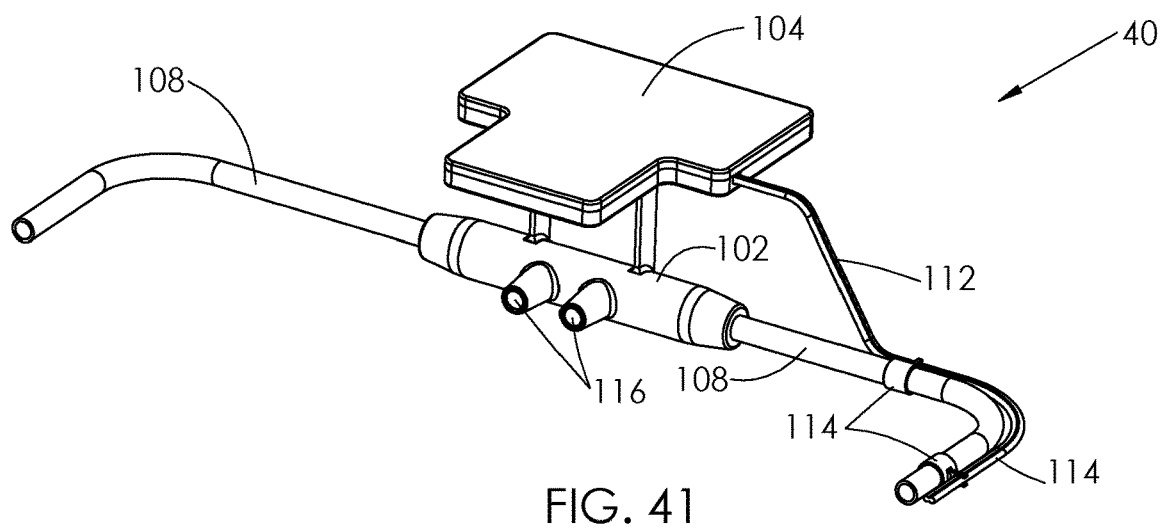
FIG. 41 shows an alternate perspective view of the therapeutic lights of FIG. 40.
Figure 42:
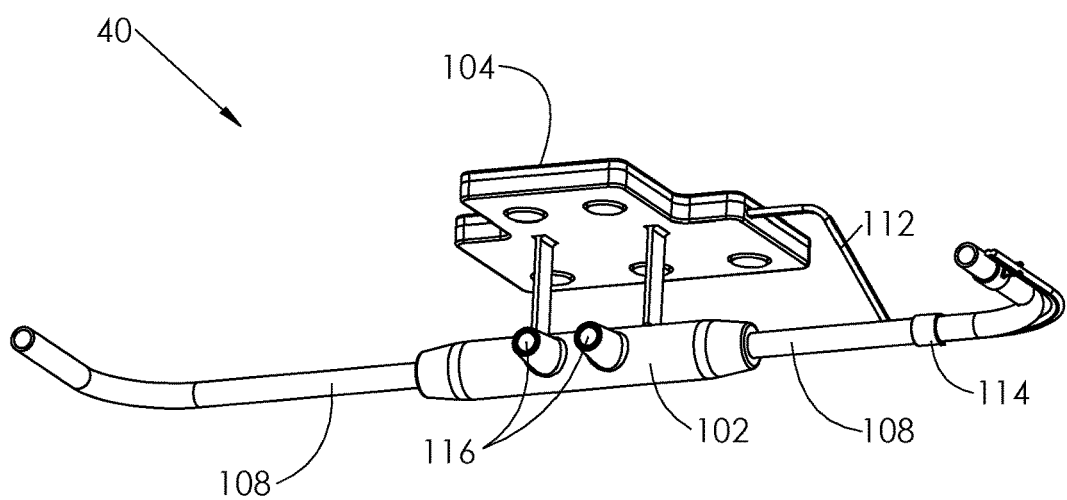
FIG. 42 shows an alternate perspective view of the therapeutic lights of FIG. 40.
Figure 43:
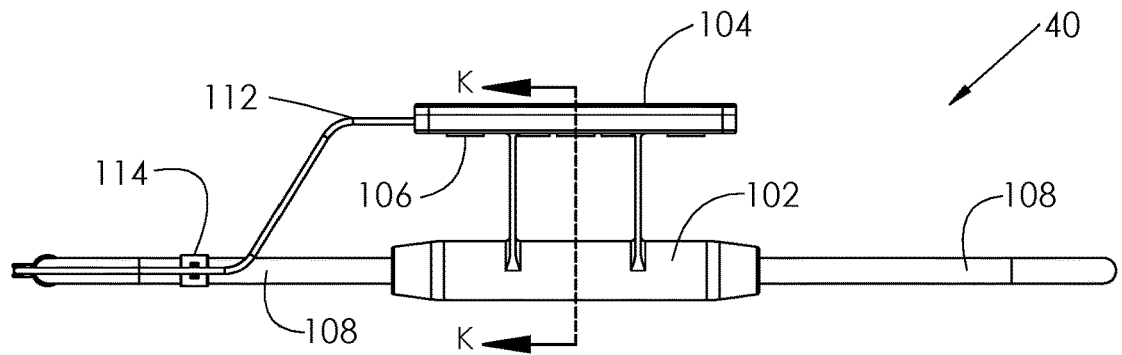
FIG. 43 shows a bottom view of the therapeutic lights of FIG. 40.
Figure 44:
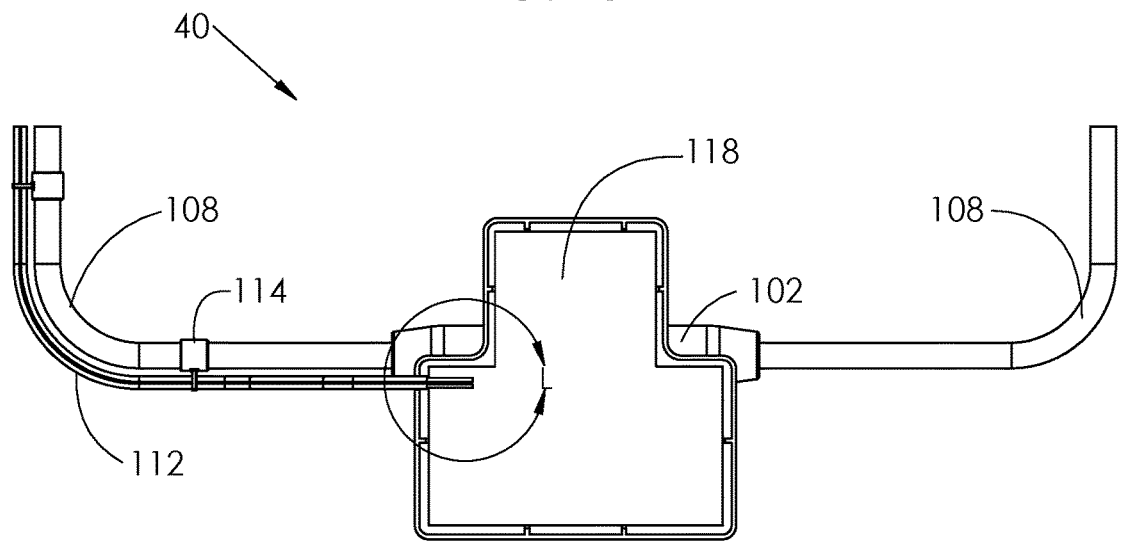
FIG. 44 shows a front view of the therapeutic lights of FIG. 40 with a front plate removed.
Figure 45:
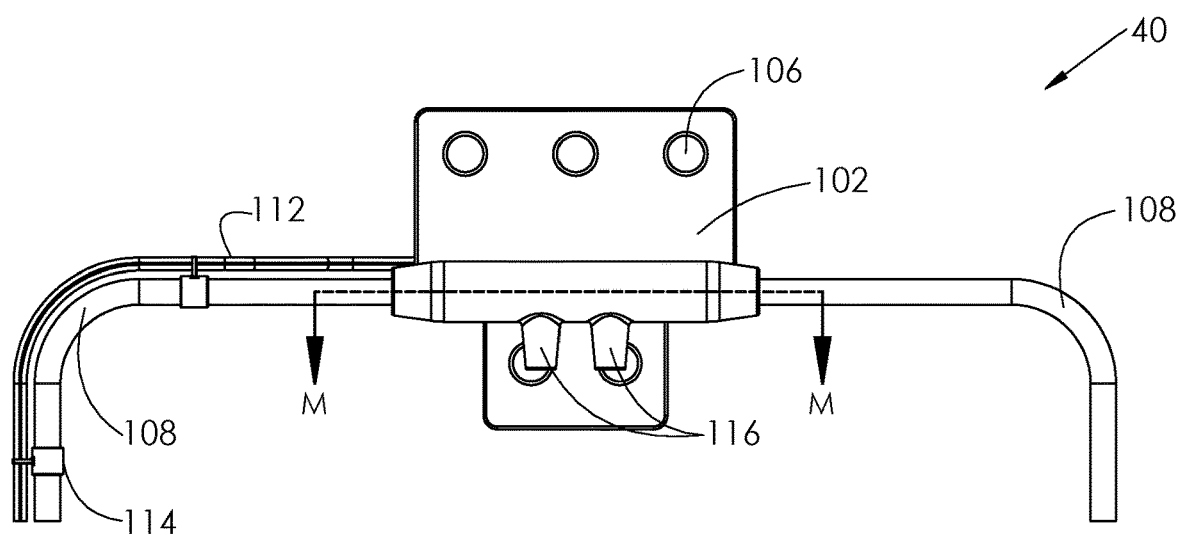
FIG. 45 shows a rear view of the therapeutic lights of FIG. 40.
Figure 57A:
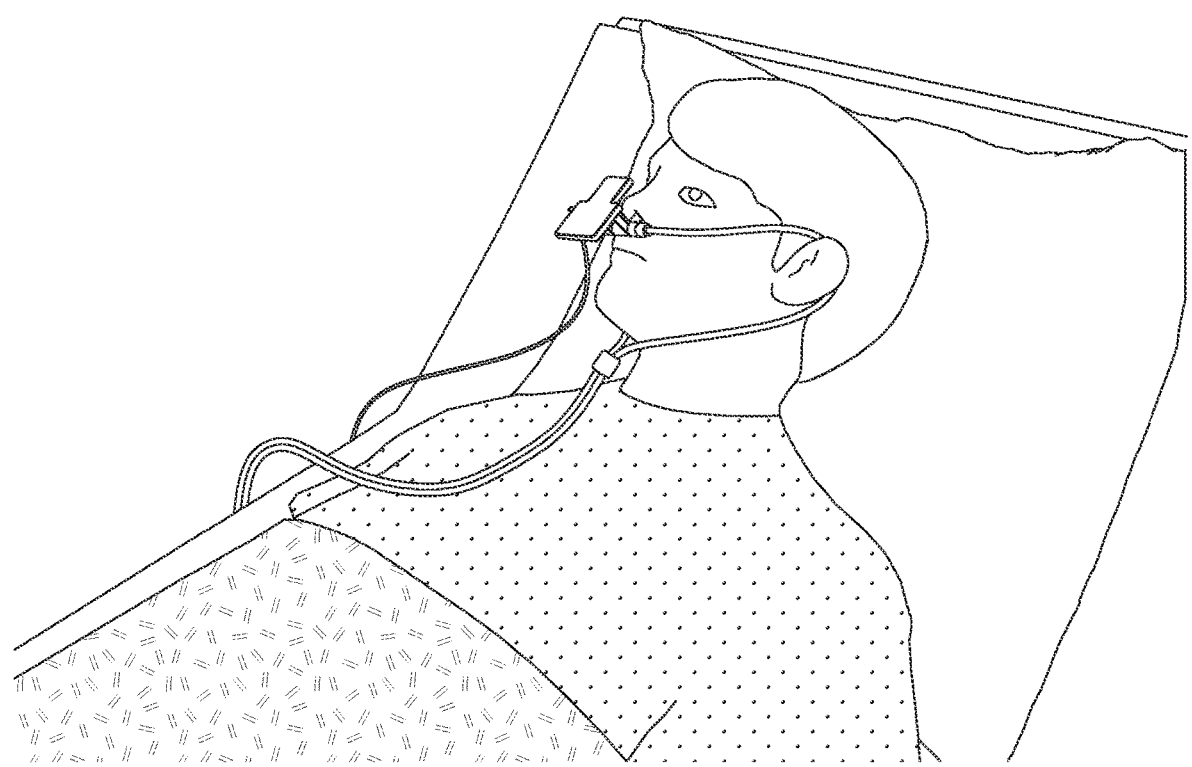
FIG. 57A and FIG. 57B show views of therapeutic light integrated in a nasal cannula assembly of FIG. 40 installed onto a patient resting on a hospital bed.
Figure 57B:
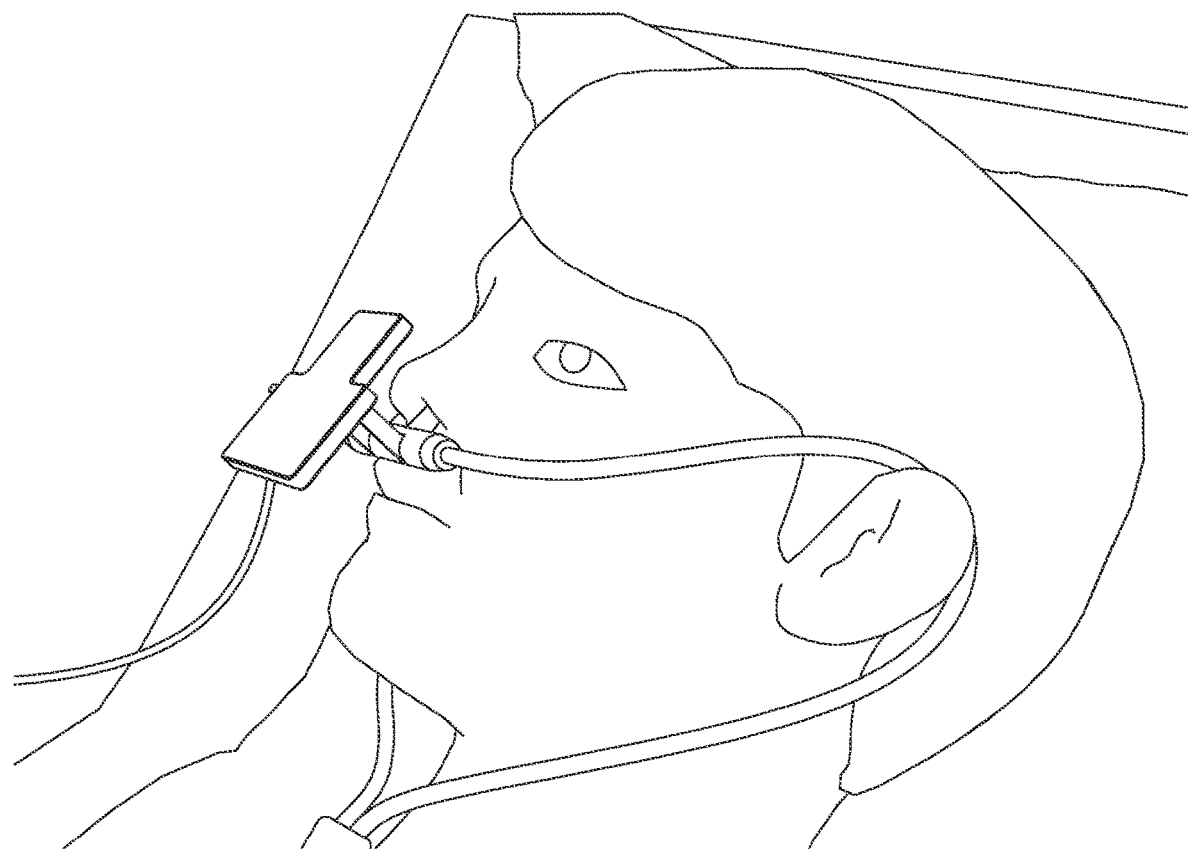
Figure 58:
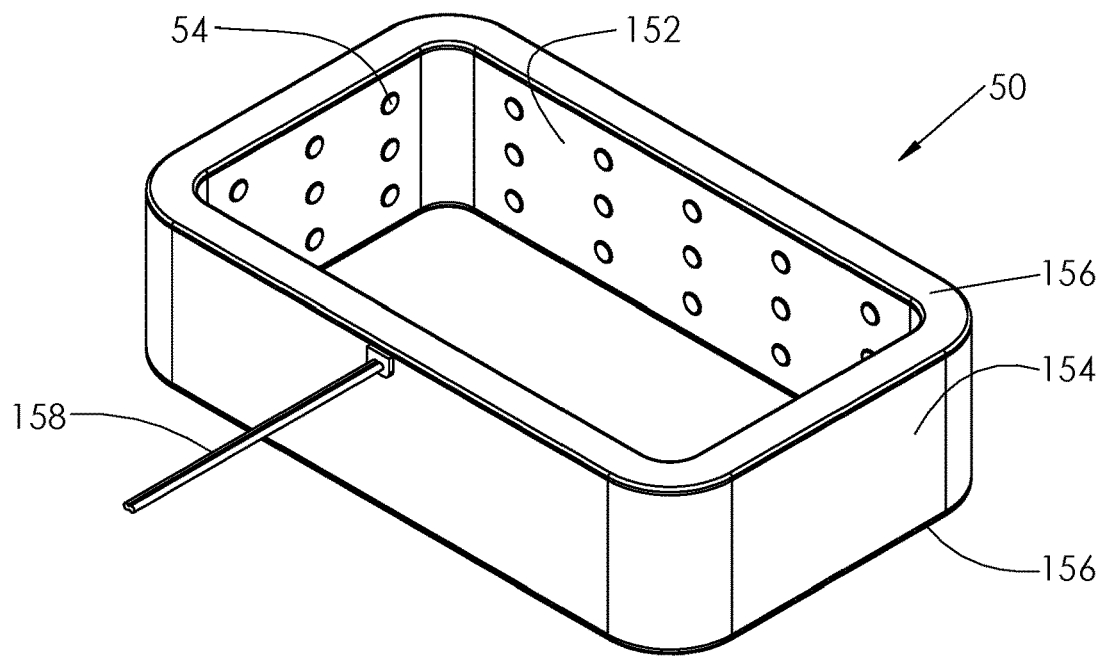
FIG. 58 to 67C show a therapeutic light surgical site ring for open surgery.
Figure 59:
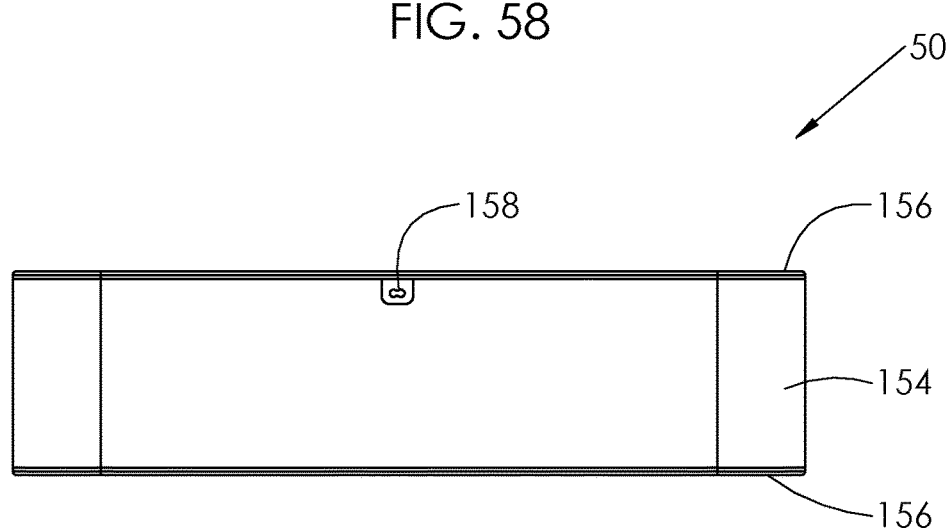
Figure 60:
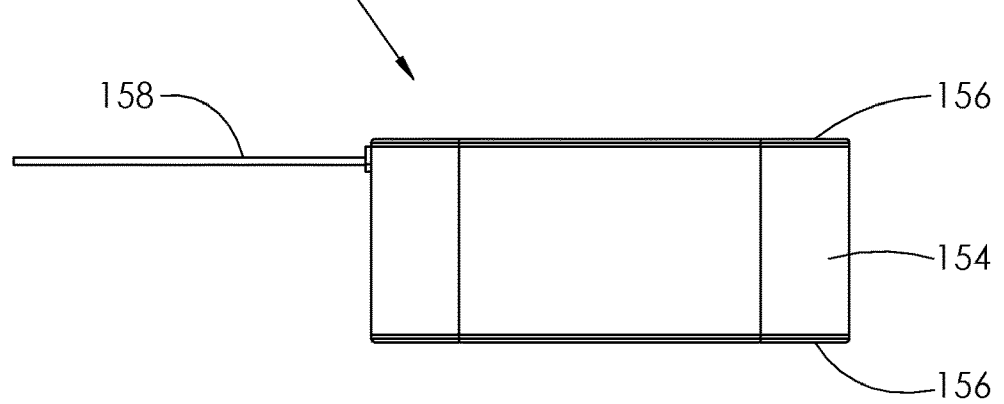
Figure 61:
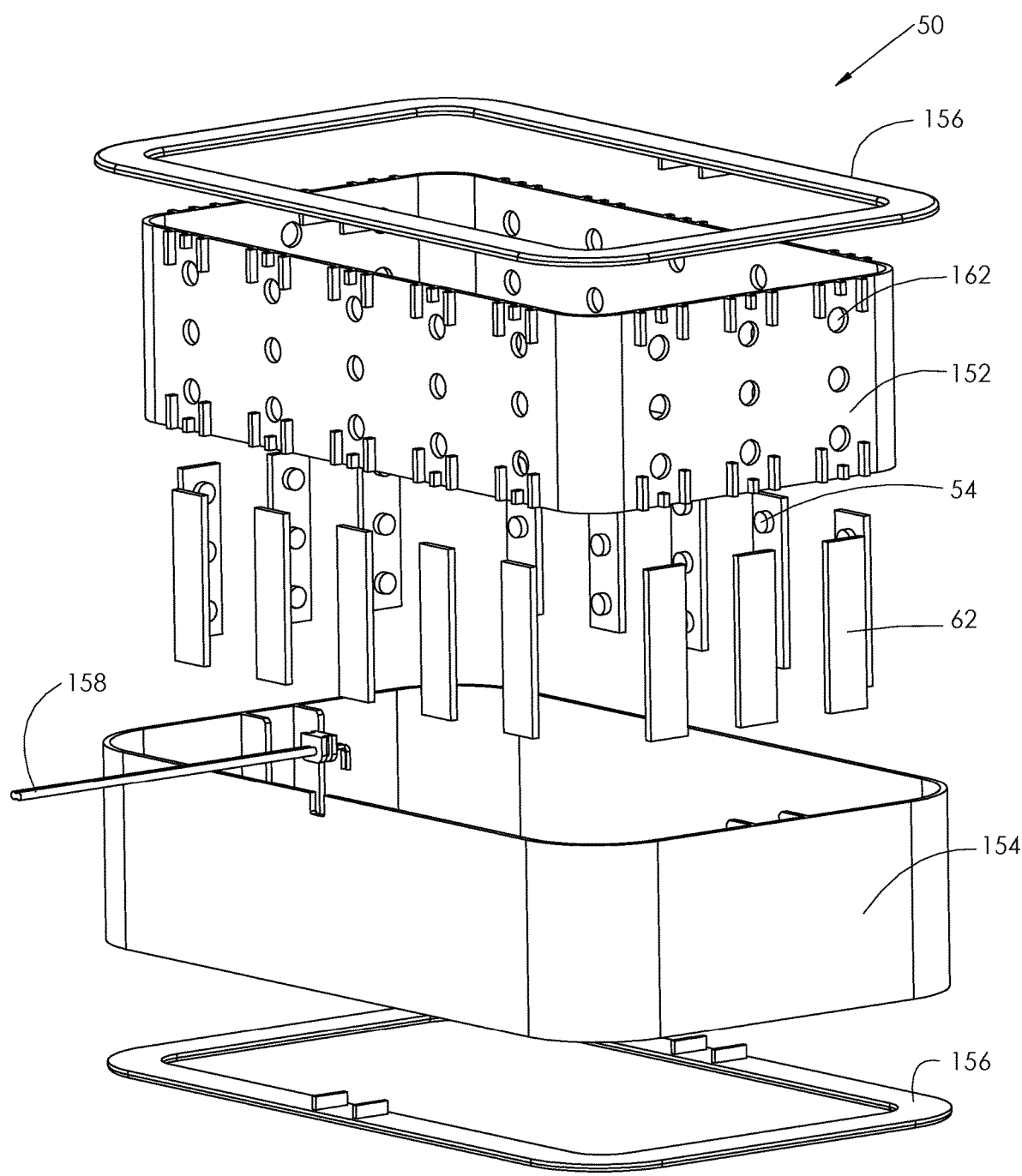
Figure 62:
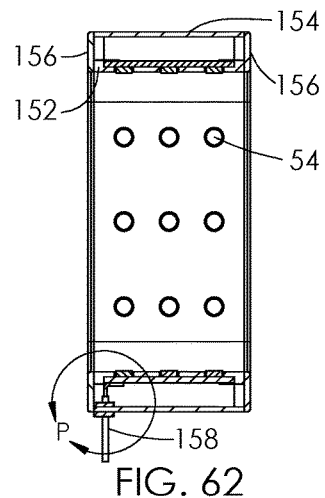
Figure 63:
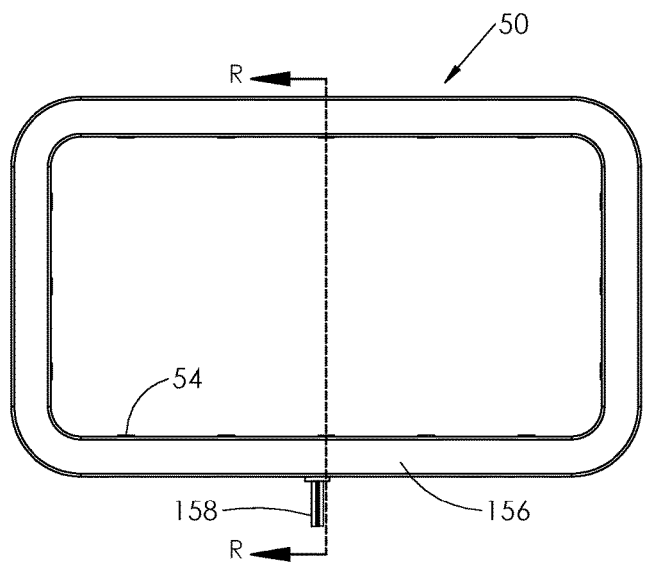
Figure 64:
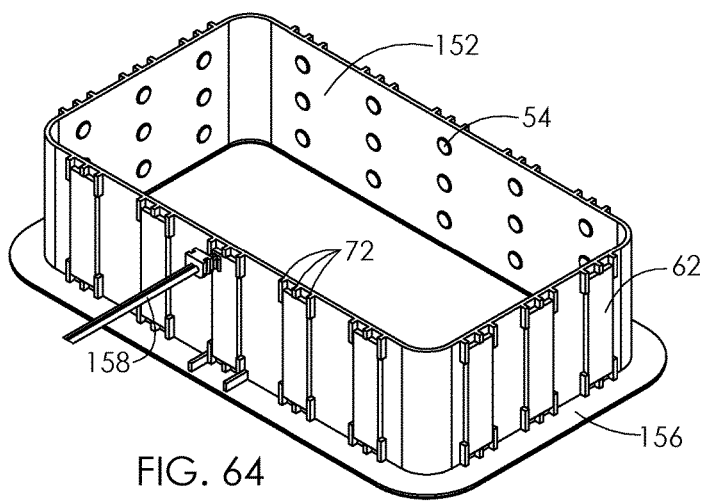
Figure 65:
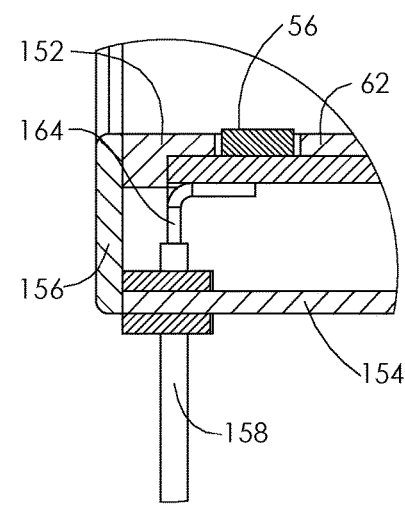
Figure 66:
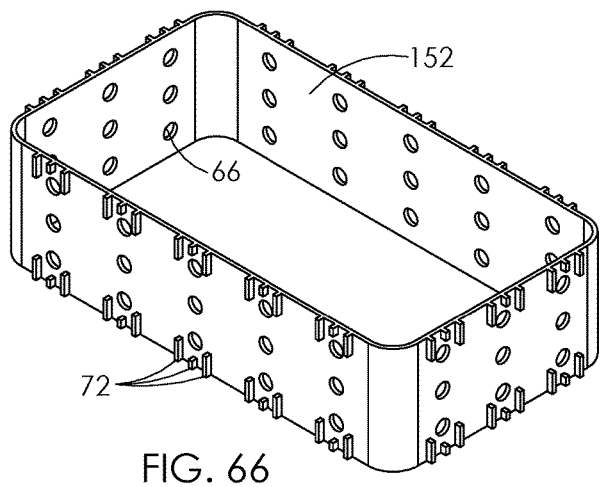

Referring now to the drawings wherein like reference numerals identify similar structural elements and features of the subject invention, there is shown in FIGS. 1-16D a therapeutic light arc 10 designed to create "arena"-style therapeutic light from a therapeutic light source 6 around a critical treatment area to reduce infectious agent counts. One embodiment shown allows a patient, whether intubated (FIG. 16C) or not, to be in bed with the arc 10 over their head localized to treat their mouth and nose area.

The arc 10 includes an inner 2 and outer 4 paneling to make up the arc 10 body and be powered through electrical cord 8 and leads 16. Inner paneling 2 can include a plurality of apertures of holes 18 for the therapeutic light source 6 to shine through. The therapeutic light source 6 is packaged between the inner 2 and outer paneling 4 by a plurality of strips 12. Each of the strips 12 are held in place by ribs 14 emanating from the edges of the inner panel 2. The exhaled air and droplets therein will be treated with the therapeutic light. The arc 10, shown here as a three-sided arc, can be resting on the bed, but in alternate embodiments users could hook the arc around the patient's head or around the back of a chair/upright hospital bed. A patient can wear UV protective glasses if needed. A further version would utilize the arc around an open surgical site in which the light works to counter any infectious agent that is aerosolized during surgery, either via electrocautery, blood spurts, smoke, or air current. The concept shown includes wired power but the device could be battery-powered. This embodiment could also have the impact of reducing infection rate of the patient by treating bacteria, viruses, and other harmful agents that may be present in the surgical cavity.

Referring to FIGS. 17-25A, there is shown a therapeutic light arc 20 made of inner 22 and outer panels 24 with smoke evacuation capabilities through evacuator 26. A filter element 34 is embedded within the evacuator 26 to filter particulate and harmful materials from the cauterizing smoke and a conduit 32 to evacuate the smoke. This arc 20, shown here as a three-sided arc, works actively remove air or smoke surrounding an infectious patient and could be used to suction and kill infectious agents from a breathing patient or from smoke generated at a surgical site. Inner paneling 22 includes a plurality of apertures of holes 18 for the therapeutic light source 6 to shine through. The therapeutic light source 6 is packaged between the inner 22 and outer paneling 24 by a plurality of strips 12. Each of the strips 12 are held in place by ribs 14 emanating from the edges of the inner panel 2. A wired power source 8 is shown but it could be battery-powered. Inner paneling 24 also include slits 28 to allow the evacuator 26 to pull the smoke through the light arc 20. This embodiment shows a conduit 32 connecting to an external suction source but there an internal fan or pump that pulls untreated air into the therapeutic light area (and/or filter) and treats it right at the operative site is also considered.

Referring now to FIGS. 26-39B, there is shown a therapeutic light surgical site ring 30 which forms an enclosed space defined by inner 44 and outer 42 panels and braces 46 to connect the panels 44 and 42 with smoke evacuation capabilities. Outer panel 42 includes guides 74 to align the braces and corresponding ribs 82. Ring device 30 surrounding a surgical site or an endoscopic or laparoscopic surgical port site, includes slits 56 to allow the smoke through, a filter element 68 and a conduit 58 attached to a suction device such as a smoke evacuator or wall suction. The suction evacuates surgical smoke and gases from the surgical area generated by electrocautery devices or other sources. Infectious agents carried in that smoke or gas can be treated with the therapeutic light source 54 aligned on sheets 62 and held in place by ribs 72 to shine through ports 66. The filter element may consist of a paper filter, a carbon or activated charcoal filter, or other type of filter. The embodiment shown connects via a wire 52 and lead 64 to an external power source but it could utilize integral battery power. Although positioning ribs 82 are shown in this and other embodiments, it is within the scope of this disclosure that other positioning mechanisms can be used to align therapeutic light sources with enclosures or housings.

Referring to FIGS. 40-57B, there is shown therapeutic lights integrated into a nasal cannula assembly 40. Patients with some respiratory distress may be treated with supplemental Oxygen through a Nasal Cannula. This pumps additional oxygen into the nose of a patient in order to improve oxygen saturation and help with respiratory distress. Therapeutic lights are integrated into, assembled, or attached to a nasal cannula to apply therapeutic light to the nose and mouth area of a potentially infectious patient. The assembly 40 includes a housing for storing the LEDs 106. The LEDs 106 are associated with a circuit board 118 between the inner 102 and outer 104 plates. The inner plate 101 includes apertures 122 for allowing the therapeutic light source 106 to shine through, as well as a plurality of ribs 124 for fixating the therapeutic light source board 118. The inner plate 101 is attached to a pair of spacing ribs 128 which include an attachment mechanism for coupling to the nasal cannula 102. The nasal cannula 102 with tubing 108 and wire support rings 114 also includes a pair of ports 116. The spacing ribs 128 are placed adjacent to the ports 116 in order to place the therapeutic light source 106 at a specified distance to the patient's nose and mouth. One embodiment of therapeutic lights connected to a nasal cannula with wired power 112 is shown as item, though other shapes and connection points are included within the scope of this disclosure. The device may also be battery powered.

Referring now to FIGS. 58-67C, there is shown a therapeutic light surgical site ring. This device is an assembly built to surround an open surgical site and apply radially inward therapeutic light to reduce viral load from any escaping infectious agents from the surgical site. Especially for surgeons and nurses who may need to be close to an open surgical site in order to see what they are doing, this is a critical safety device that could work to reduce the risk that they breathe in any infectious agent that is aerosolized during surgery, either via electrocautery, blood spurts, smoke, or air current. One rectangular embodiment is shown by item 50. The therapeutic light surgical site rectangle 50 which forms an enclosed space defined by inner 152 and outer 154 panels and braces 156 to connect the panels 152 and 154. Outer panel 154 includes guides 155 to align the braces 156 and corresponding ribs 157. Any infections agents can be treated with the therapeutic light emanating from therapeutic light source 54 aligned on sheets 62 and held in place by ribs 72 to shine through ports 162. The embodiment shown connects via a wire 158 and lead 164 to an external power source but it could utilize integral battery power.

Figure 67:
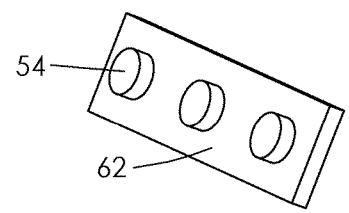
Figure 67A:
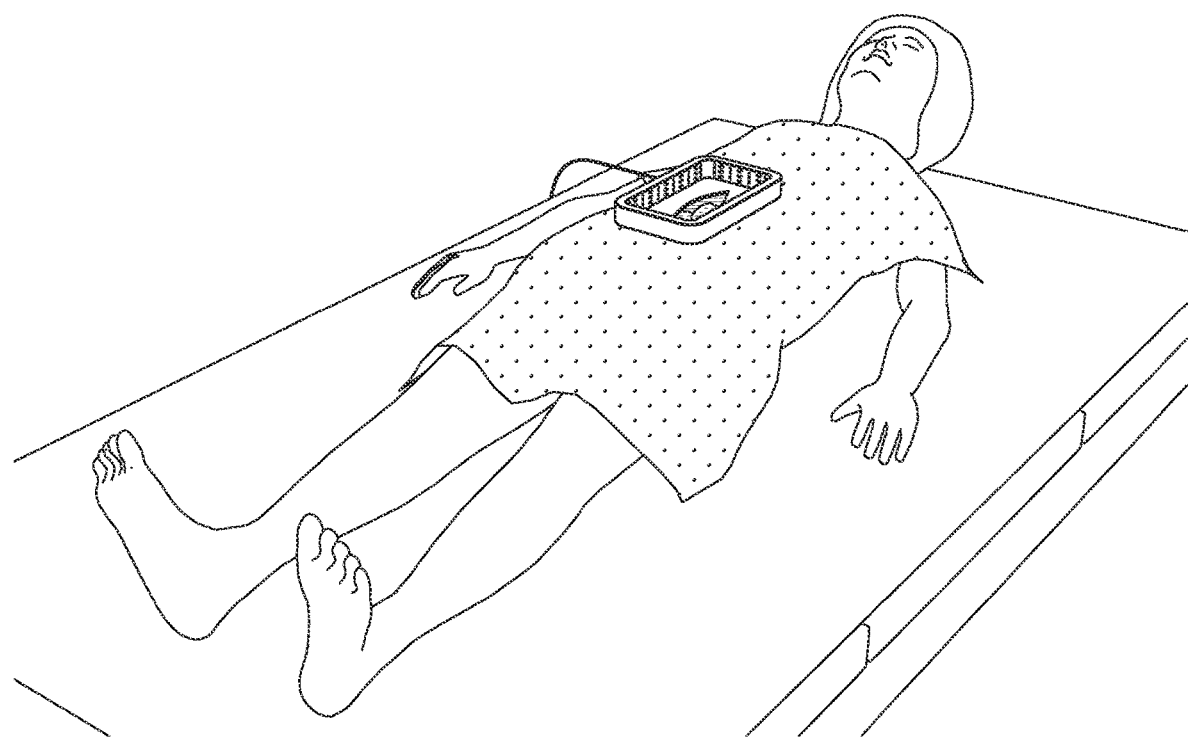
FIG. 67A shows the light ring for open and laparoscopic surgery of FIG. 58 installed around a surgical wound on a patient undergoing surgery.
Figure 67B:
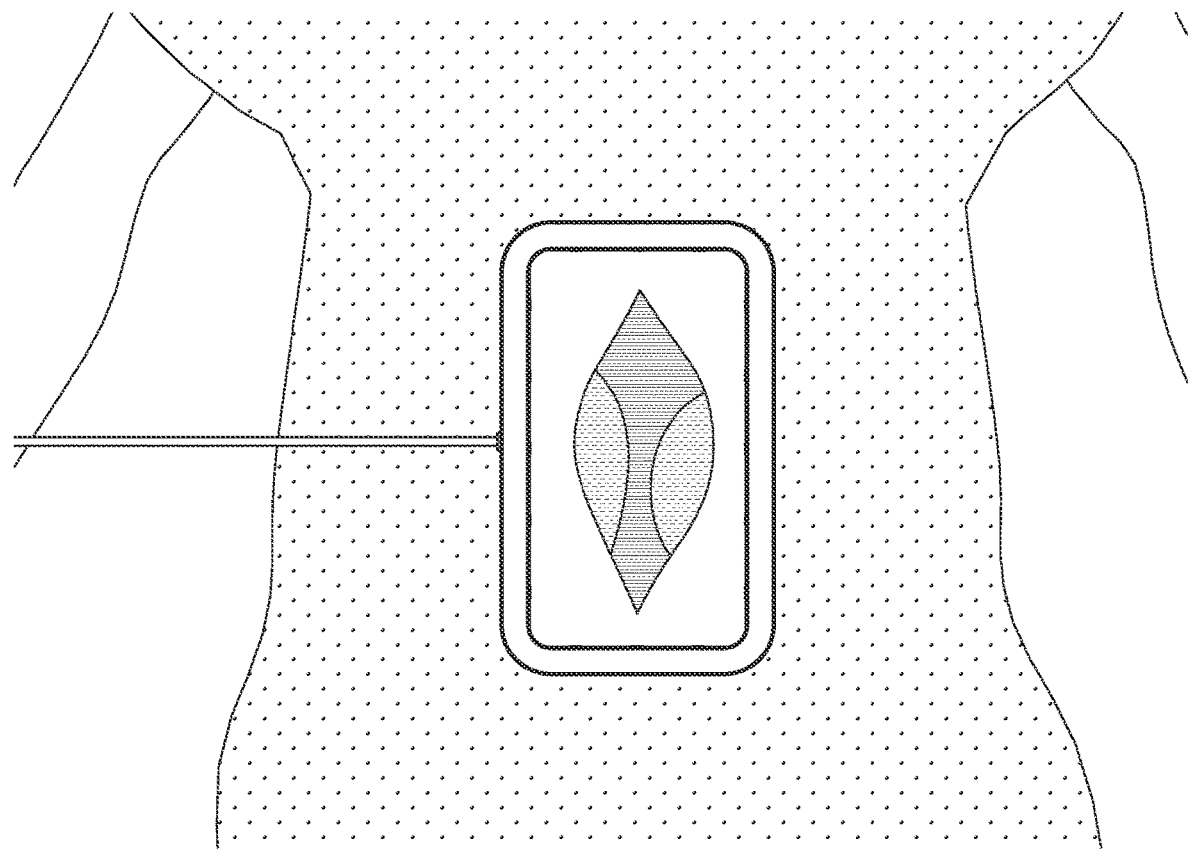
FIG. 67B shows a top view of the light ring for open and laparoscopic surgery of FIG. 67A installed around a surgical wound on a patient undergoing surgery.
Figure 67C:
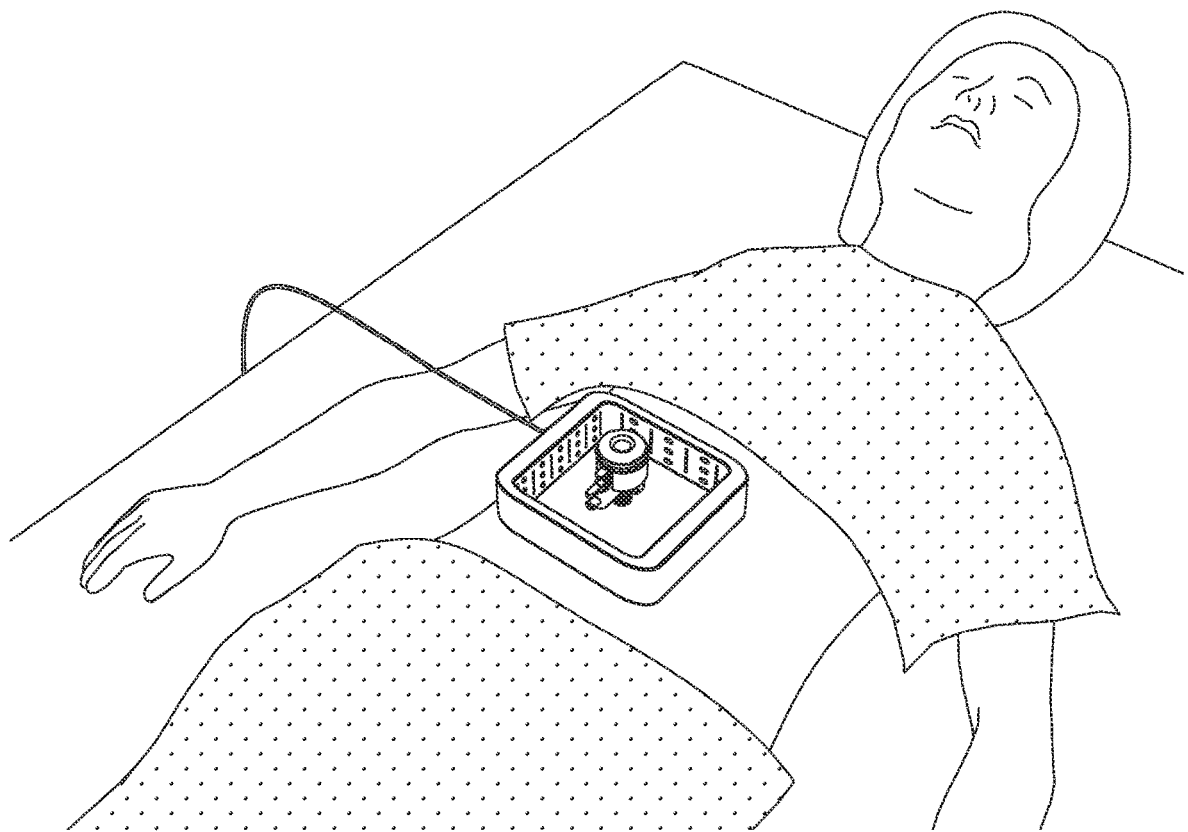
Figure 68:
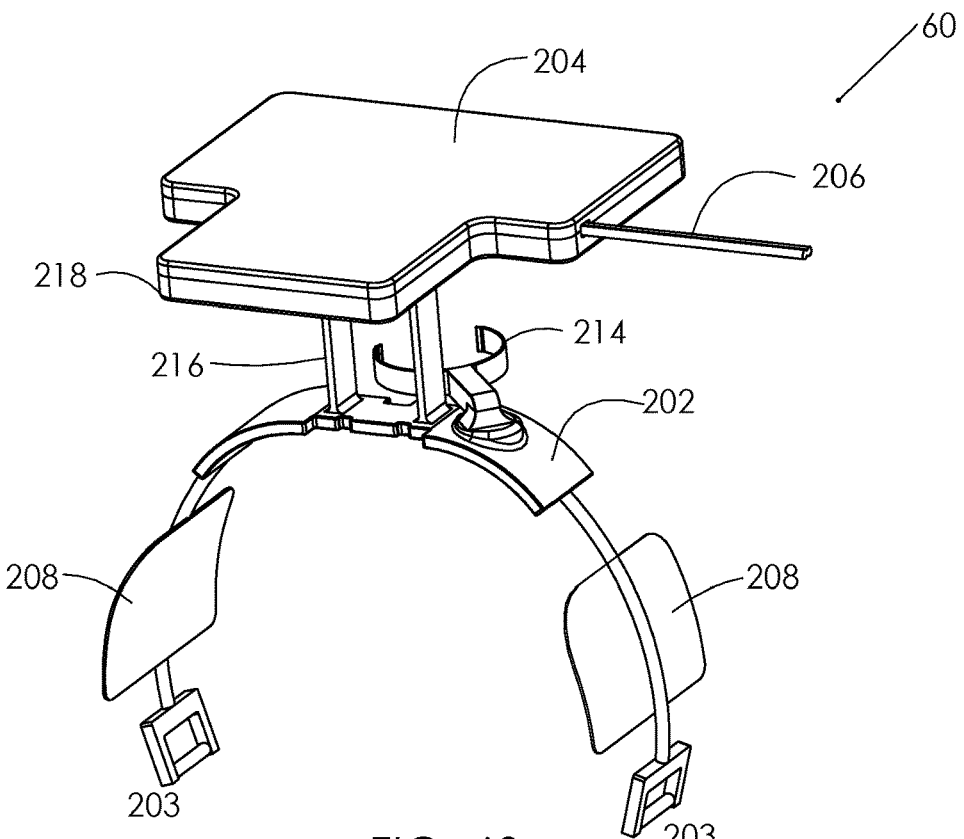
FIG. 68 shows therapeutic light integrated into a ventilator mouthpiece or head strap for intubated patients.
Figure 69:
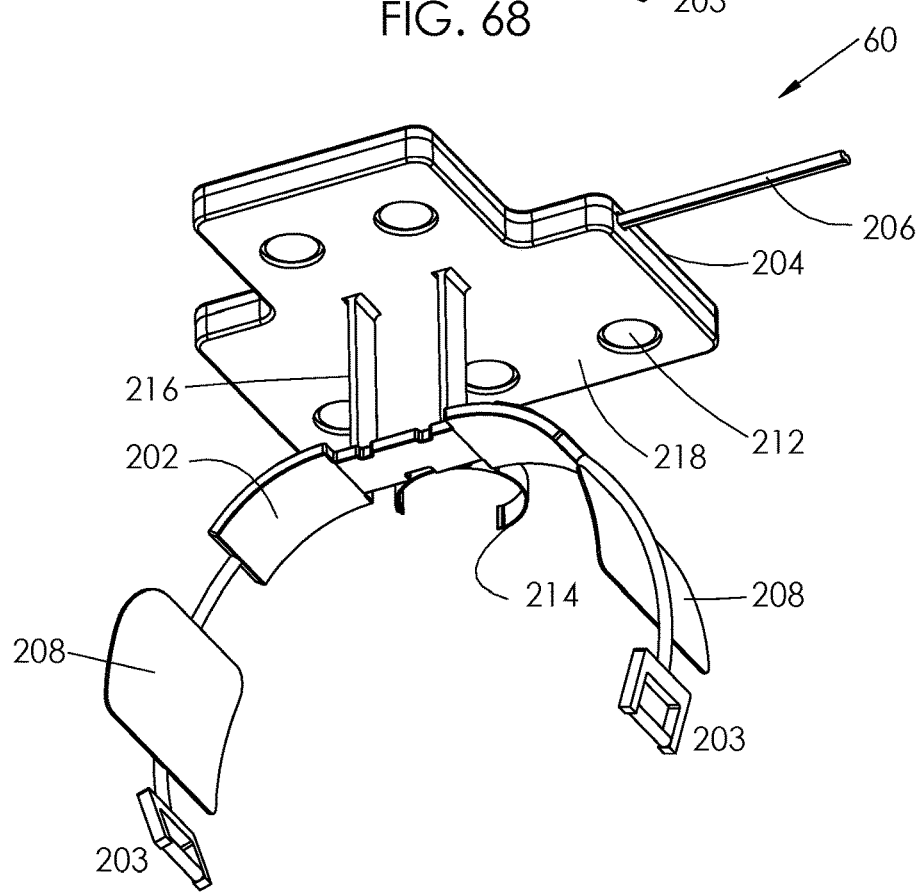
FIG. 69 shows an isometric view of the therapeutic light of FIG. 68.

To protect the device from accidental movement device can be attached to the patient skin or a drape via adhesive tape or it may be weighted to hold in place. An alternate embodiment with a smaller shape and dimensions can be used for laparoscopic surgery for by placing it around a laparoscopic port. This could be particularly helpful for insufflated surgical cavities in which pressurized insufflation gas may leak from a port or a port site while carrying an infectious agent, this is shown in FIG. 67C. During surgery, multiple rings could be used such that each laparoscopic port site had a therapeutic light ring.

Figure 70:
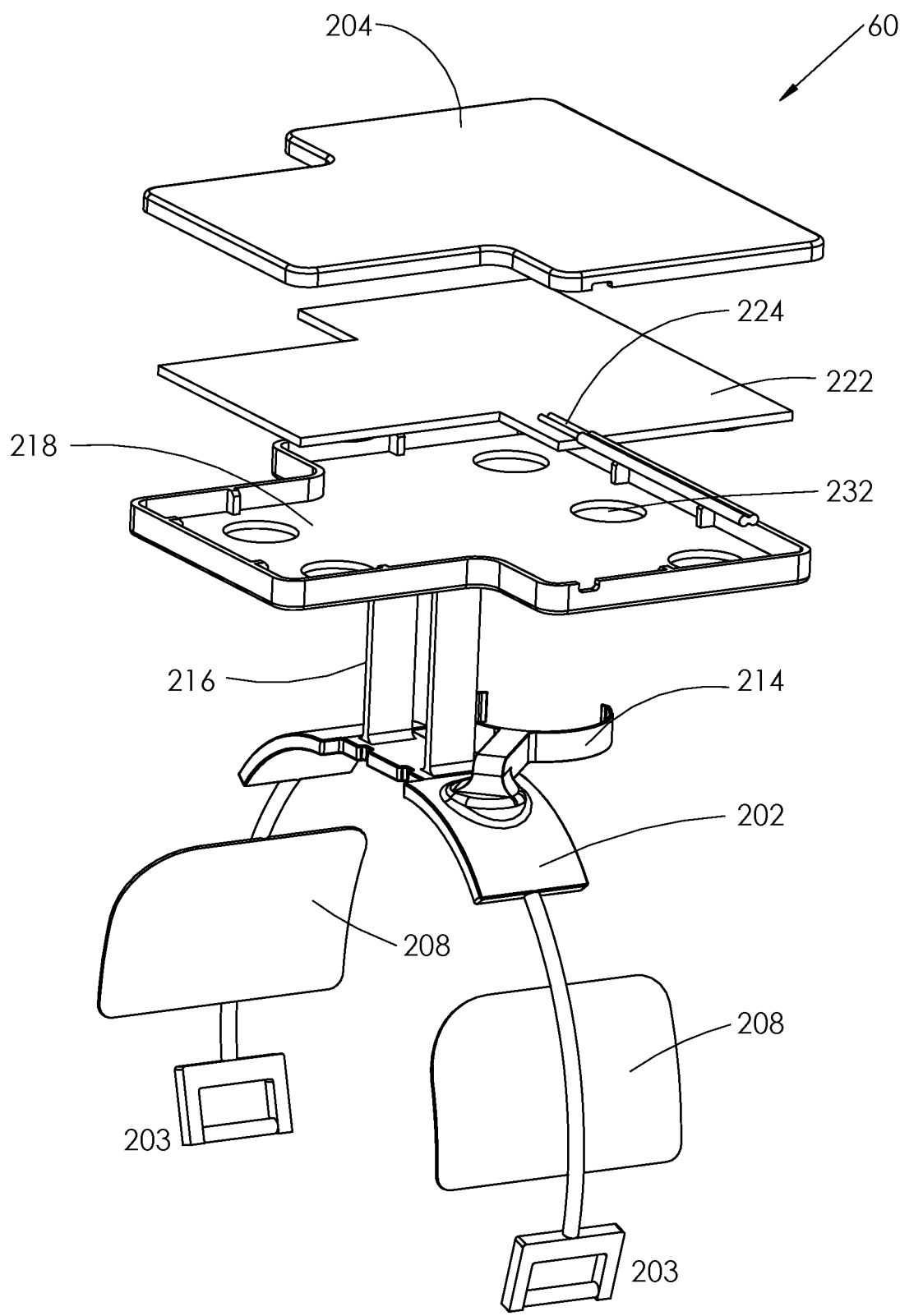
FIG. 70 shows an exploded view the therapeutic light of FIG. 68.
Figure 71:
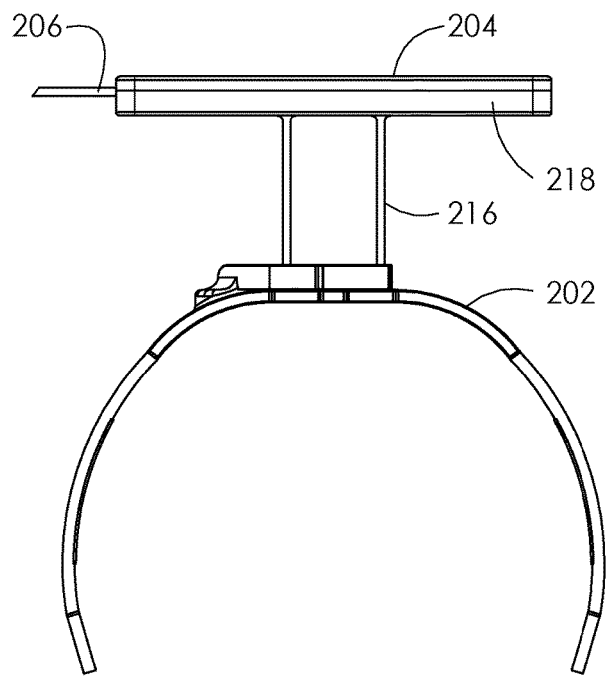
FIG. 71 shows a top view of the therapeutic light of FIG. 68.
Figure 72:
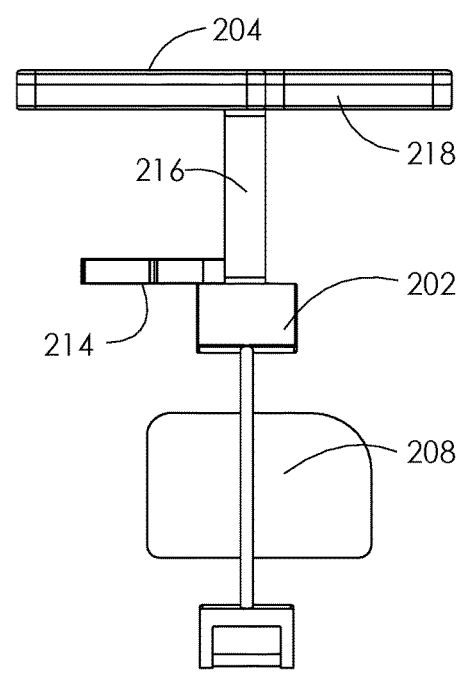
FIG. 72 shows a side view of the therapeutic light of FIG. 68.
Figure 73:
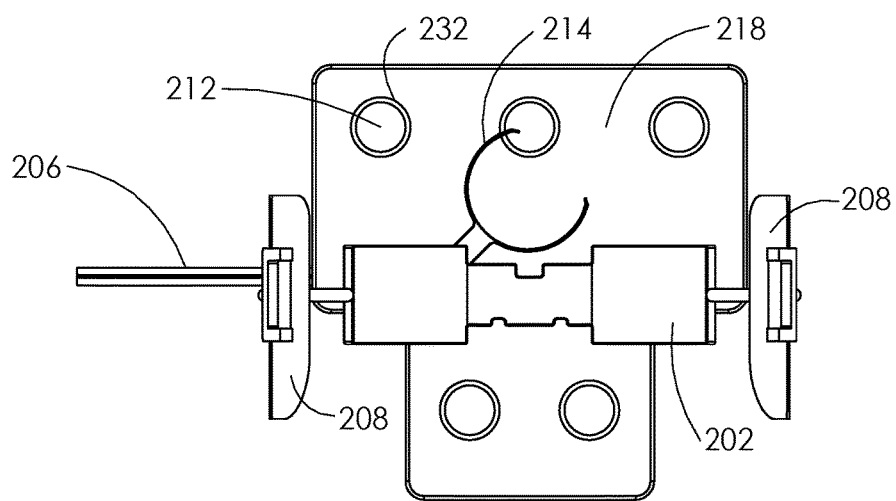
FIG. 73 shows a rear view of the therapeutic light of FIG. 68.
Figure 74:
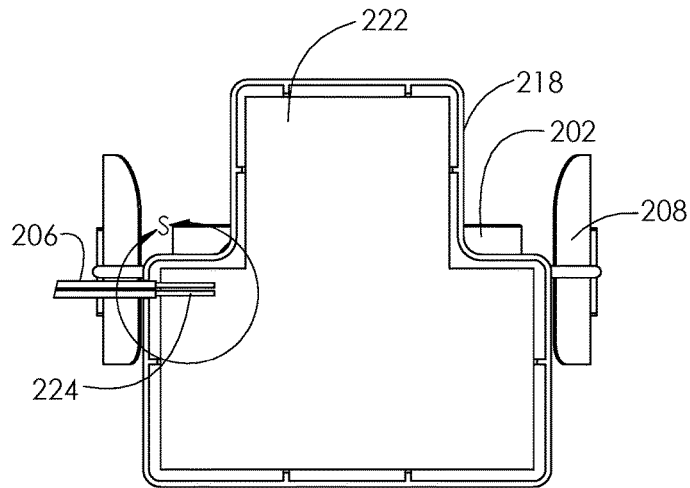
FIG. 74 shows a front view of an assembly of the therapeutic light of FIG. 68 with a front cover removed.
Figure 75:
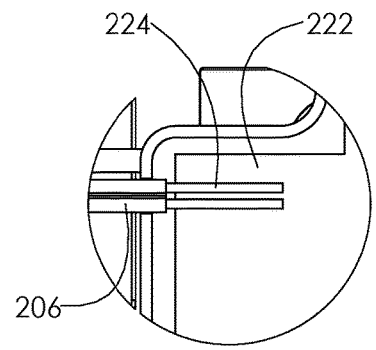
FIG. 75 shows an enlarged view S taken from FIG. 74.
Figure 76:
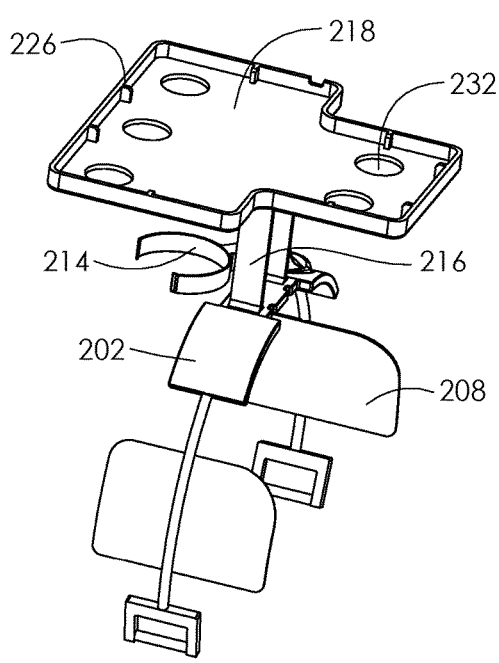
FIG. 76 shows an isometric view of an assembly of the therapeutic light of FIG. 68 when a front cover and PCB are removed.
Figure 77:
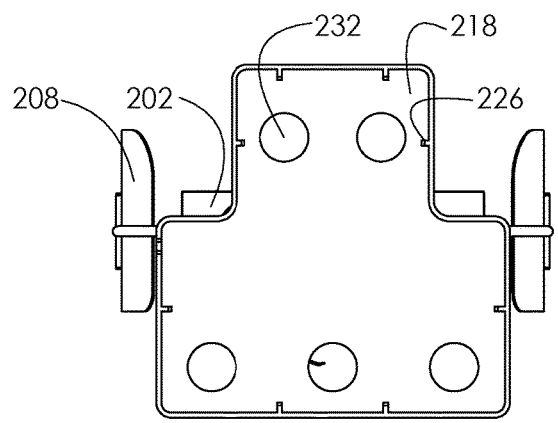
FIG. 77 shows a front view of the assembly of the therapeutic light of FIG. 68 when the front cover and PCB removed.
Figure 78:
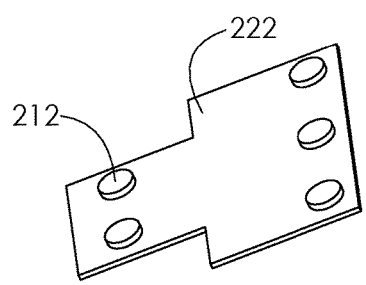
FIG. 78 shows an isometric view of the PCB of the therapeutic light of FIG. 68.
Figure 80:
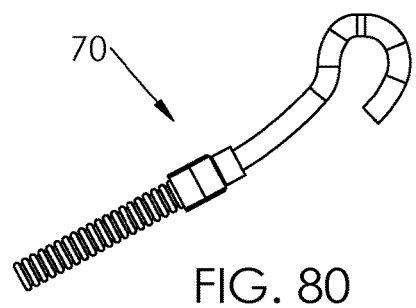
FIG. 80 shows a side view of a ventilator tubbing of FIG. 68.
Figure 79:
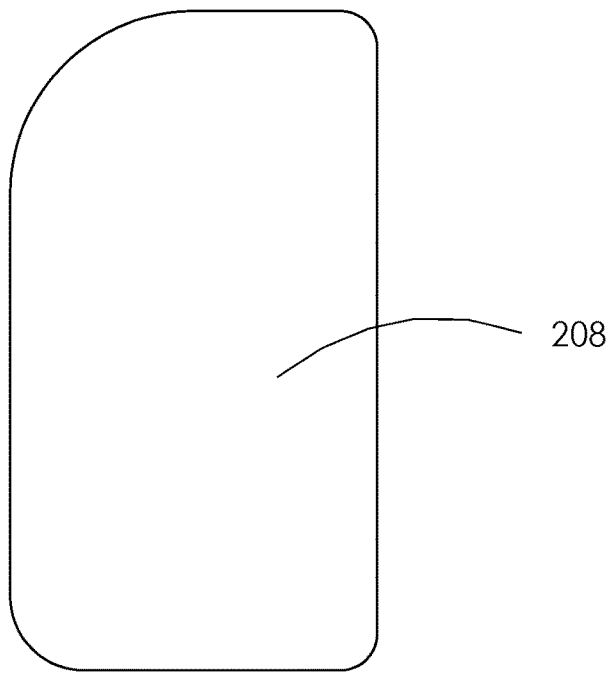
FIG. 79 shows a rear view of a face pad of the therapeutic light of FIG. 68.
Figure 81:
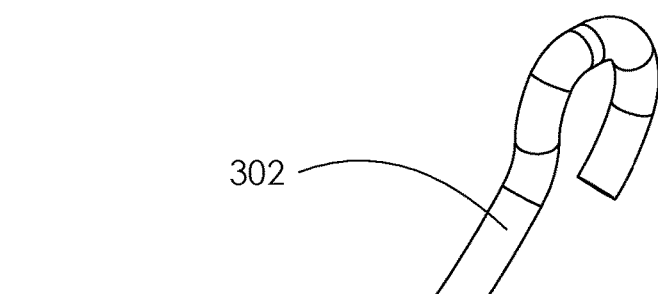
FIG. 81 shows an isometric view of the ventilator tubing of FIG. 68.
Figure 82:
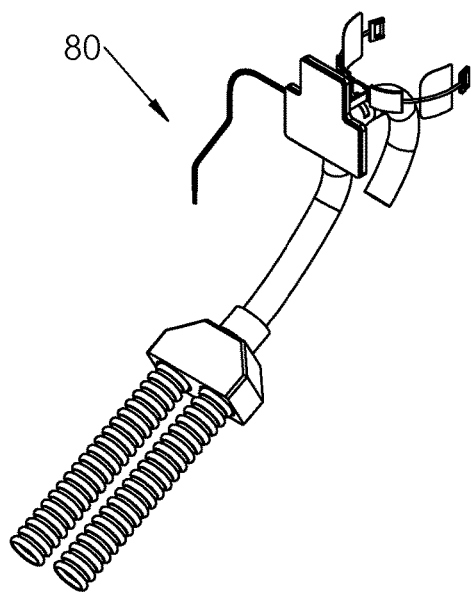
FIG. 82 shows an isometric view of ventilator tubing with attached therapeutic light assembly of FIG. 68.
Figure 83:
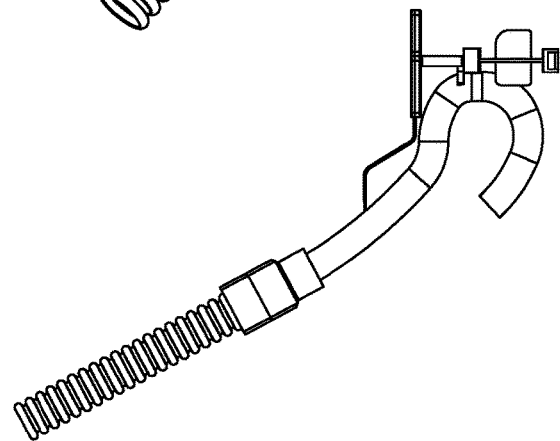
FIG. 83 shows a side view of ventilator tubing with attached therapeutic light assembly of FIG. 68.
Figure 83A:
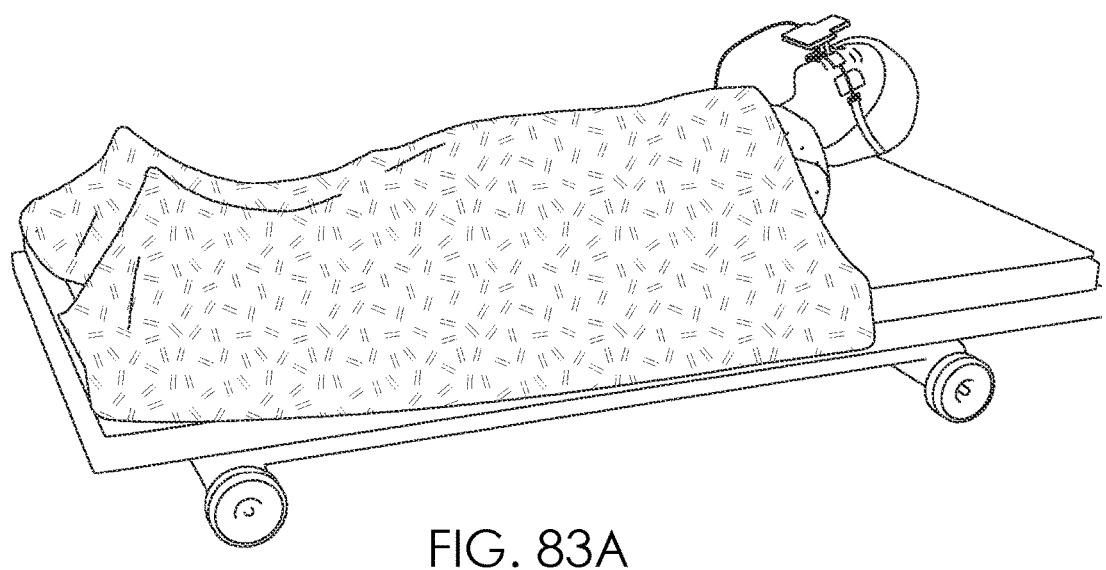
FIG. 83A shows the therapeutic light of FIG. 68 integrated into a ventilator mouthpiece for intubated patients installed onto a patient without the ventilator tubing.
Figure 83B:
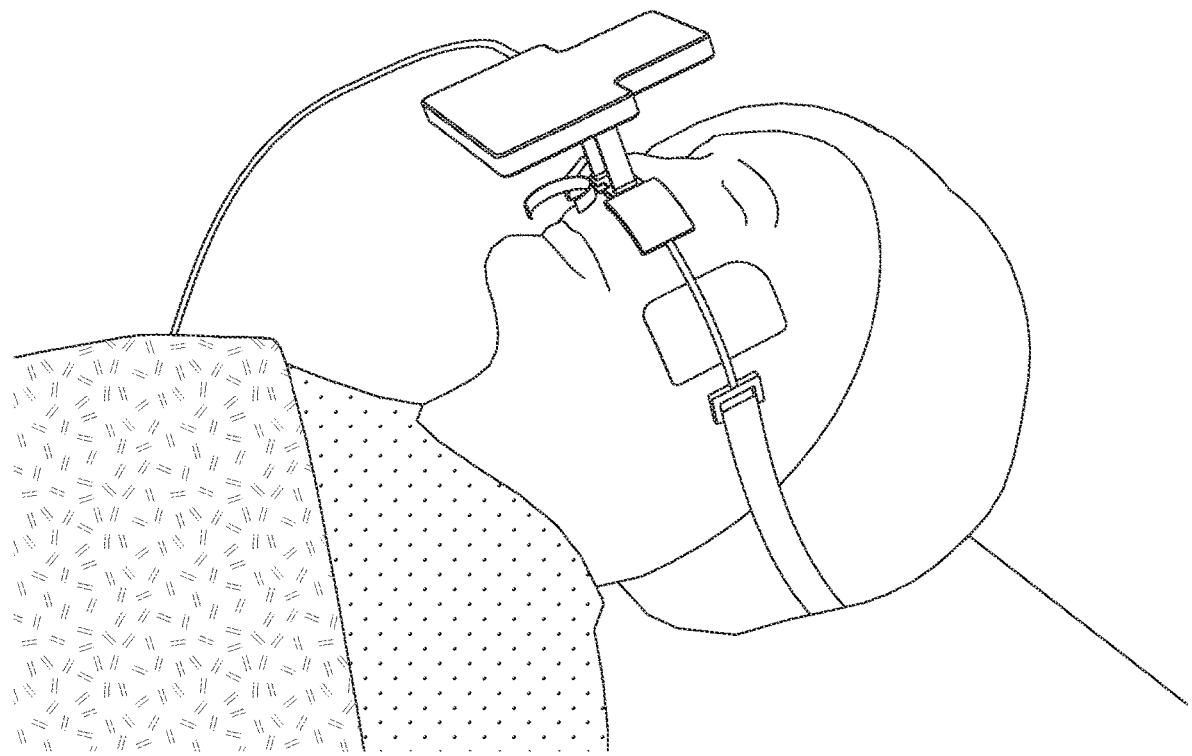
FIG. 83B shows the therapeutic light of FIG. 68 integrated into a head strap for intubated patients installed onto a patient without the ventilator tubing.
Figure 83C:
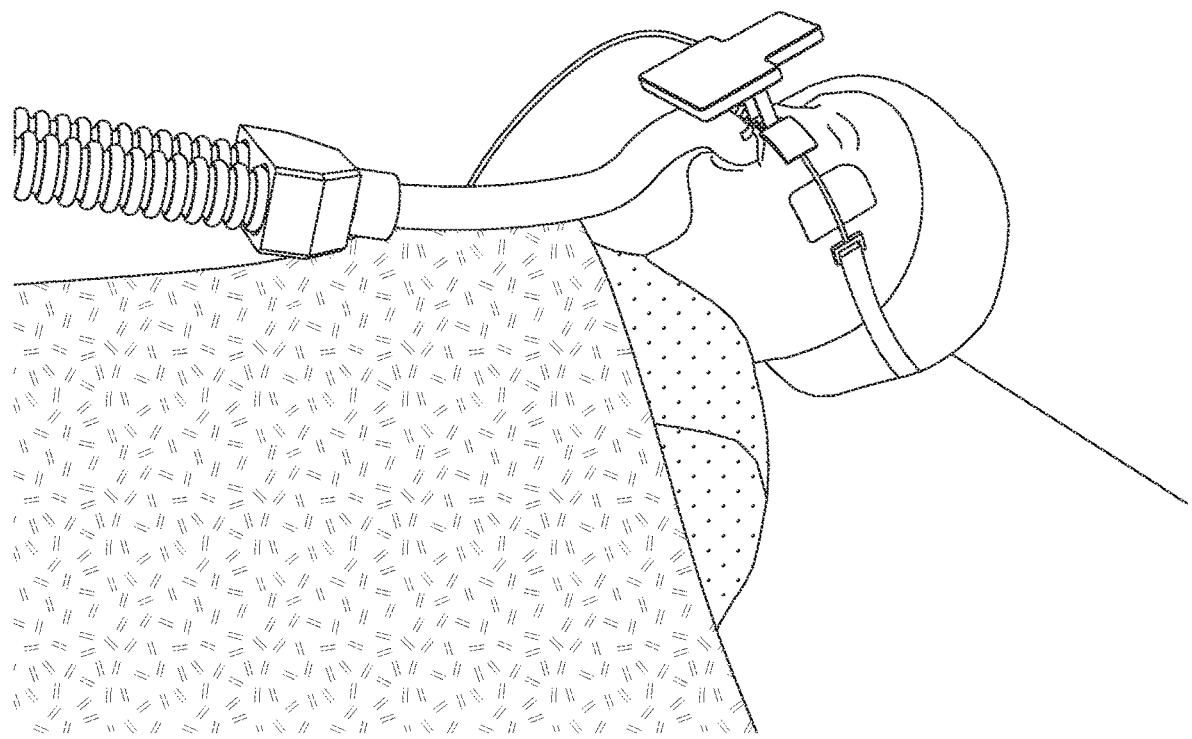
FIG. 83C shows the therapeutic light FIG. 68 integrated into a ventilator mouthpiece or head strap for intubated patients installed onto an intubated patient with ventilator tubing.
Figure 84:
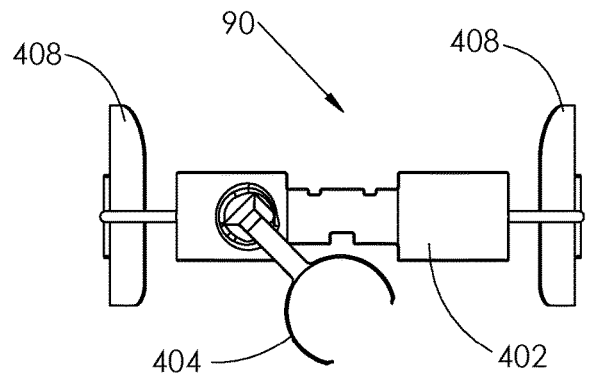
FIG. 84 shows a front view of a holding structure assembly with therapeutic lights integrated into a ventilator tube for intubated patients.
Figure 85:
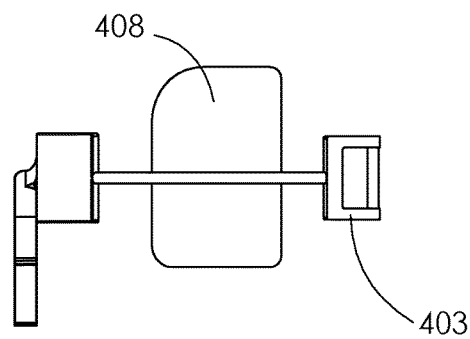
FIG. 85 shows a side view of the holding structure assembly of FIG. 84 with therapeutic lights integrated into a ventilator tube for intubated patients.
Figure 86:
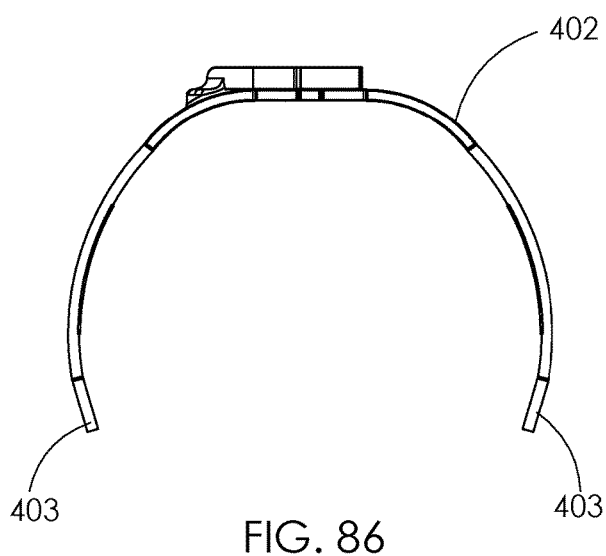
FIG. 86 shows a top view of the holding structure assembly of FIG. 84 with therapeutic lights integrated into a ventilator tube for intubated patients.
Figure 87:
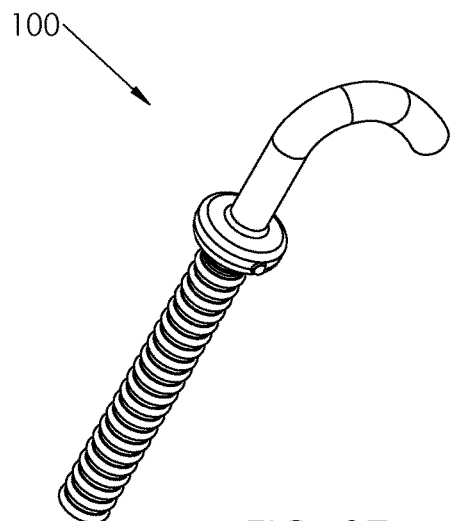
FIG. 87 shows an isometric view of the therapeutic light of FIG. 84 integrated into a ventilator tube.
Figure 88:
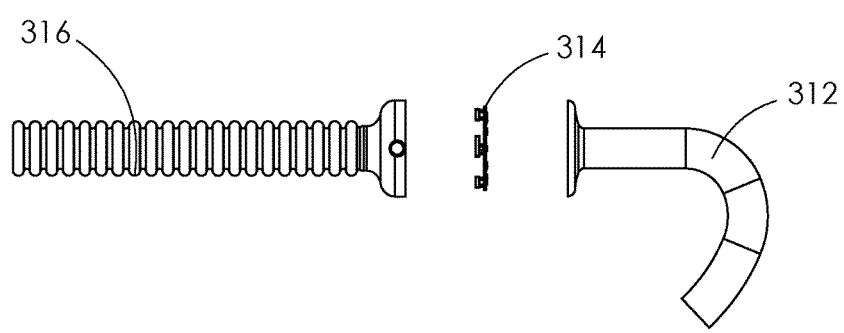
FIG. 88 shows an exploded view of the therapeutic light of FIG. 84 integrated into a ventilator tube.
Figure 89:
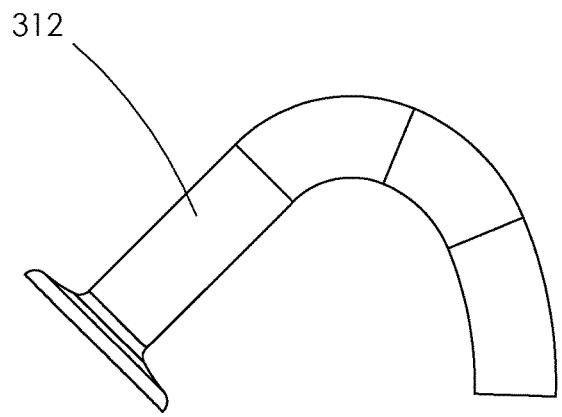
FIG. 89 shows a view of intubation tubing of FIG. 84.
Figure 90:
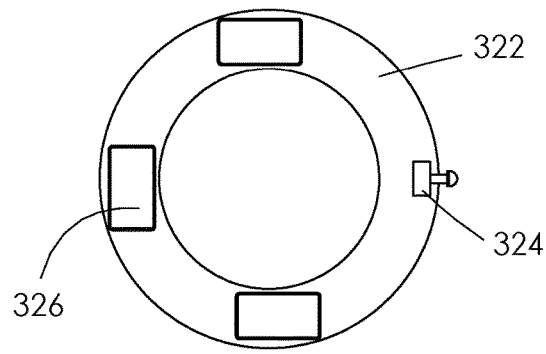
FIG. 90 shows a bottom view of a PCB of FIG. 84 with a UV LED.
Figure 91:
FIG. 91 shows a side view of the PCB of FIG. 84.
Figure 92:
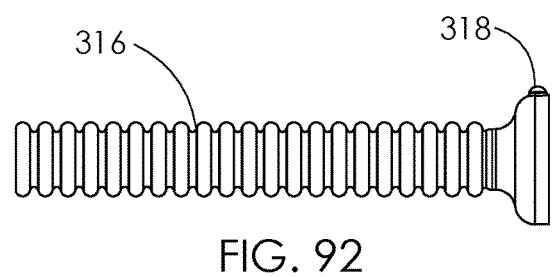
FIG. 92 shows a side view of a ventilator tubing of FIG. 84 showing an area for installing the PCB.
Figure 94:
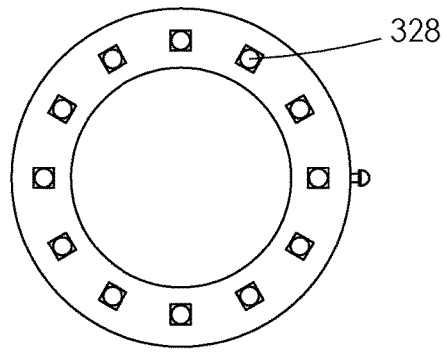
FIG. 94 shows a top view of a PCB of the therapeutic light of FIG. 84 with a UV LED.
Figure 93:
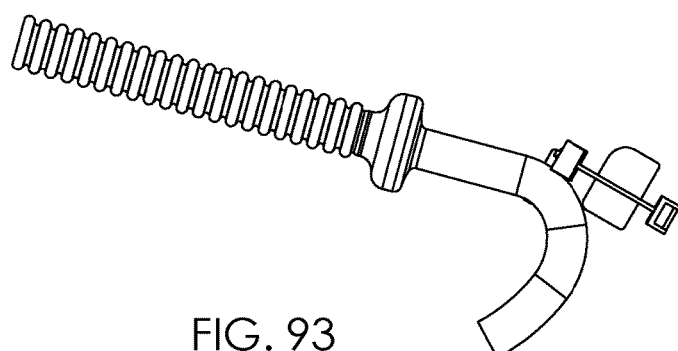
FIG. 93 shows an isometric view of tubing of FIG. 84 with a therapeutic light and holding structure assembly.
Figure 95:
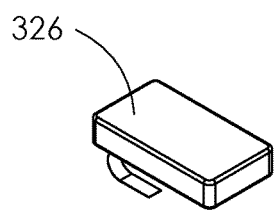
FIG. 95 shows an isometric view of a battery component of the therapeutic light of FIG. 84.
Figure 96:
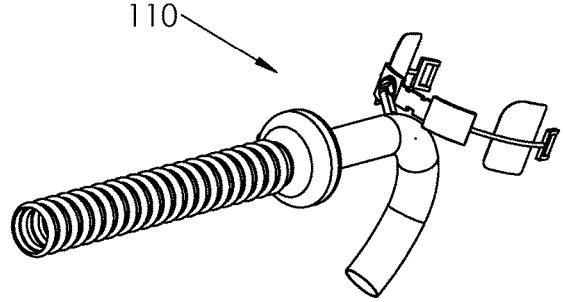
FIG. 96 shows an isometric view of assembly with the therapeutic light of FIG. 84 integrated into ventilator tubing and a holding structure assembly.
Figure 96A:
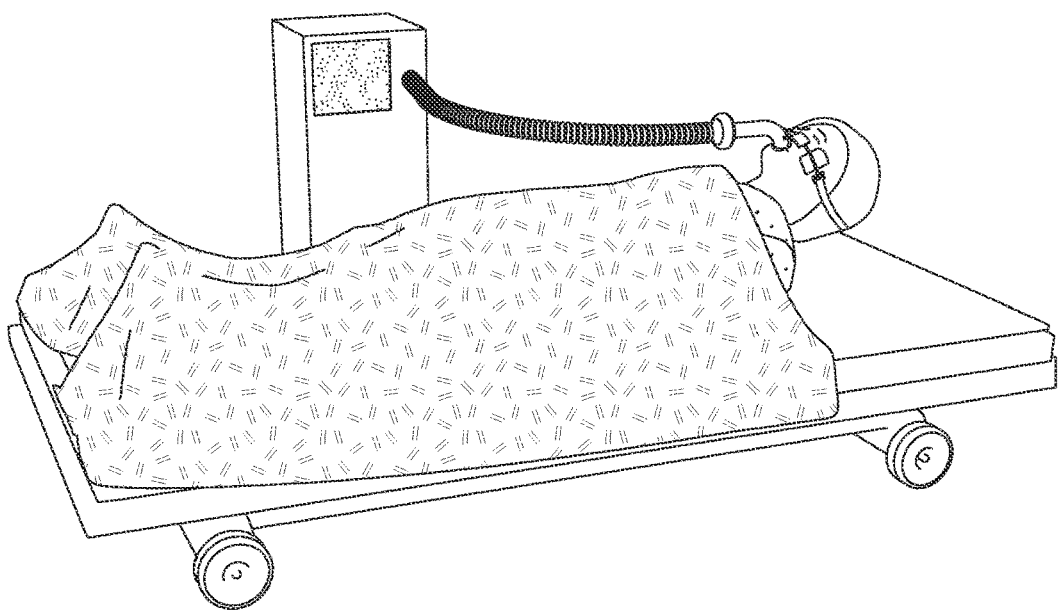
FIG. 96A shows the therapeutic light of FIG. 84 integrated into ventilator tubing and holding structure assembly installed onto an intubated patient in a hospital bed connected to a ventilator.
Figure 96B:
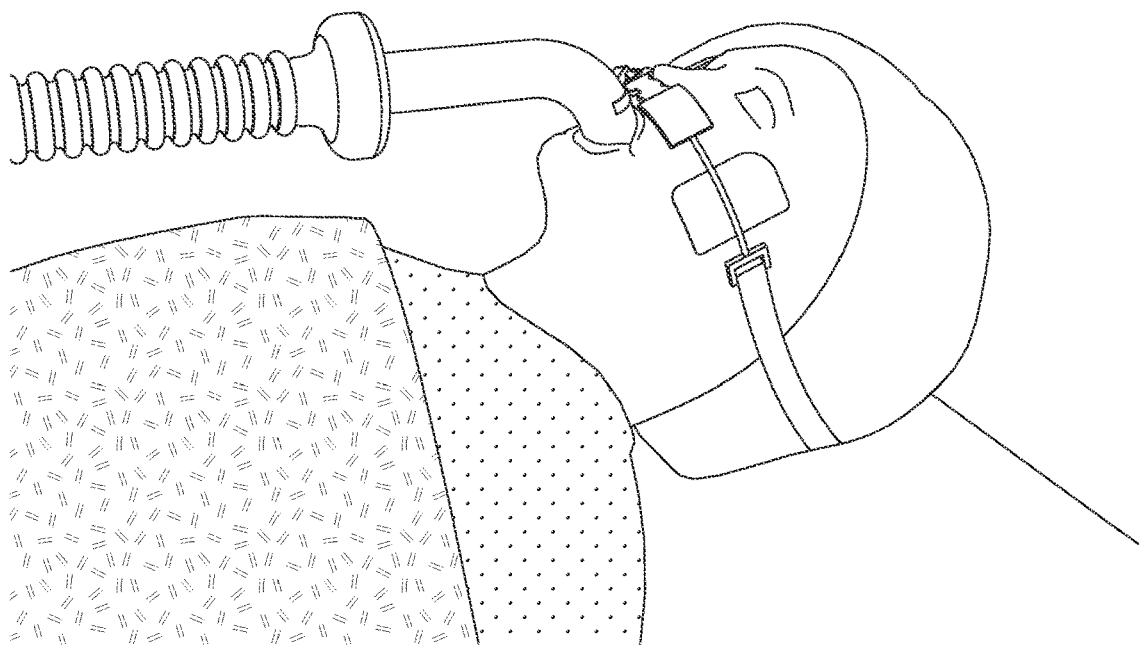
FIG. 96B shows the therapeutic light of FIG. 84 integrated into ventilator tubing and holding structure assembly installed onto an intubated patient in a hospital bed connected to a ventilator.
Figure 97:
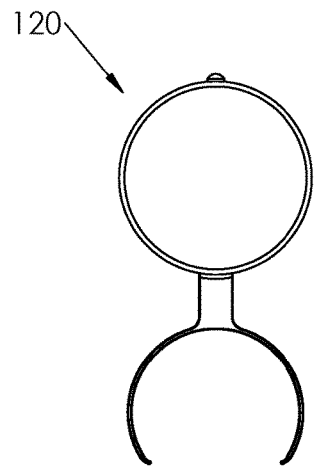
FIG. 97 shows a rear view of attachable therapeutic lights with a ventilator tube for intubated patients.
Figure 98:
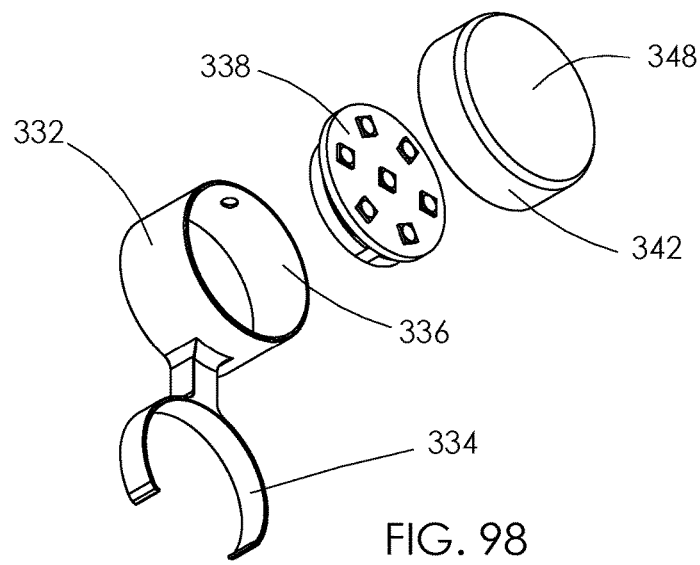
FIG. 98 shows an exploded view of the therapeutic light of FIG. 84.
Figure 99:
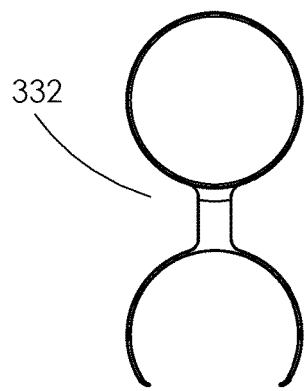
FIG. 99 shows a front view of a body component of the therapeutic light of FIG. 84.
Figure 100:
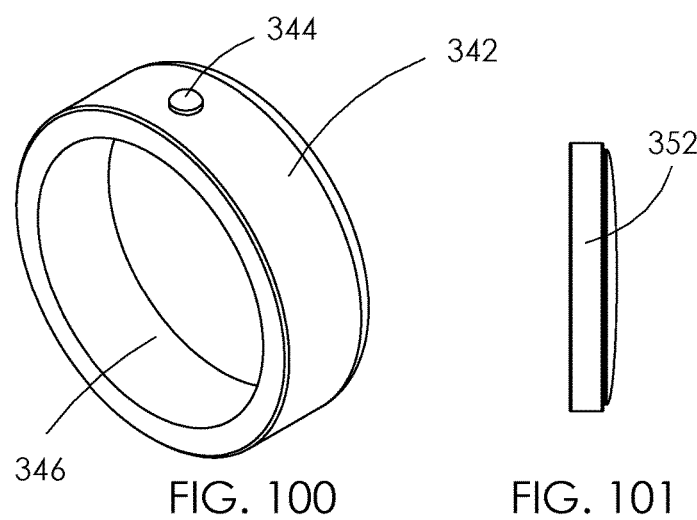
FIG. 100 shows an isometric view of a lens cover component of the therapeutic light of FIG. 84.
Figure 101:
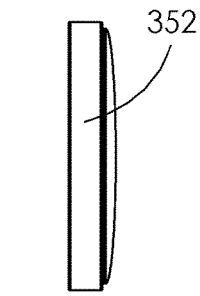
FIG. 101 shows a side view of a battery component of the therapeutic light of FIG. 84.
Figure 102:
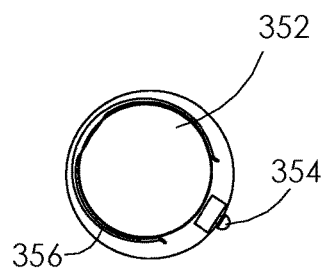
FIG. 102 shows a front view of a battery and a PCB assembly of the therapeutic light of FIG. 84.
Figure 103:
FIG. 103 shows a side of the PCB of the therapeutic light of FIG. 84.
Figure 104:
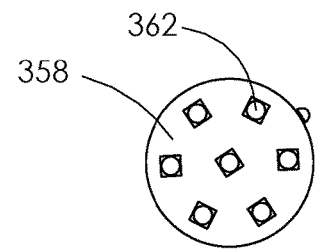
Figure 105:
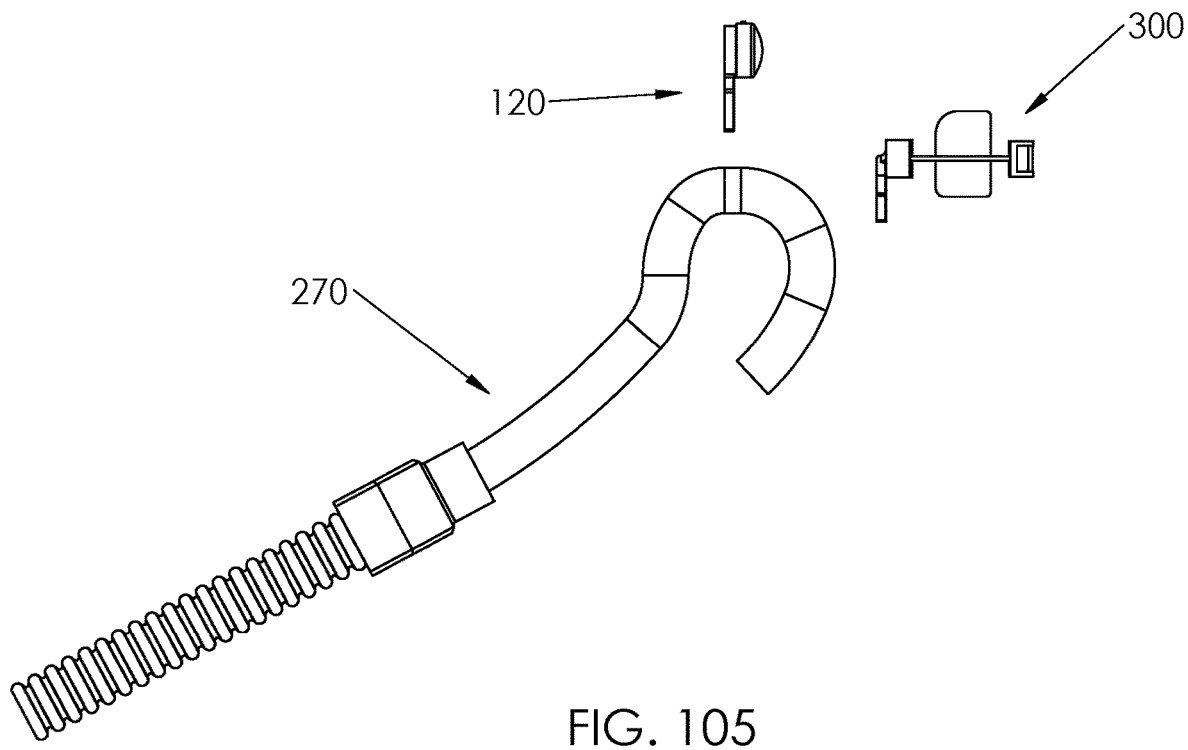
Figure 106:
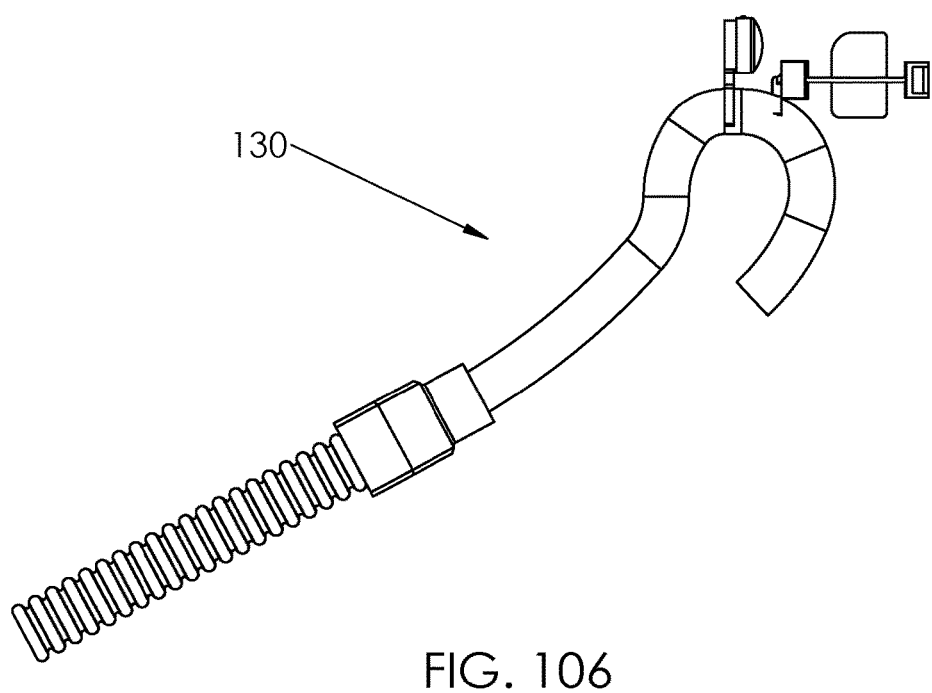
Figure 106A:
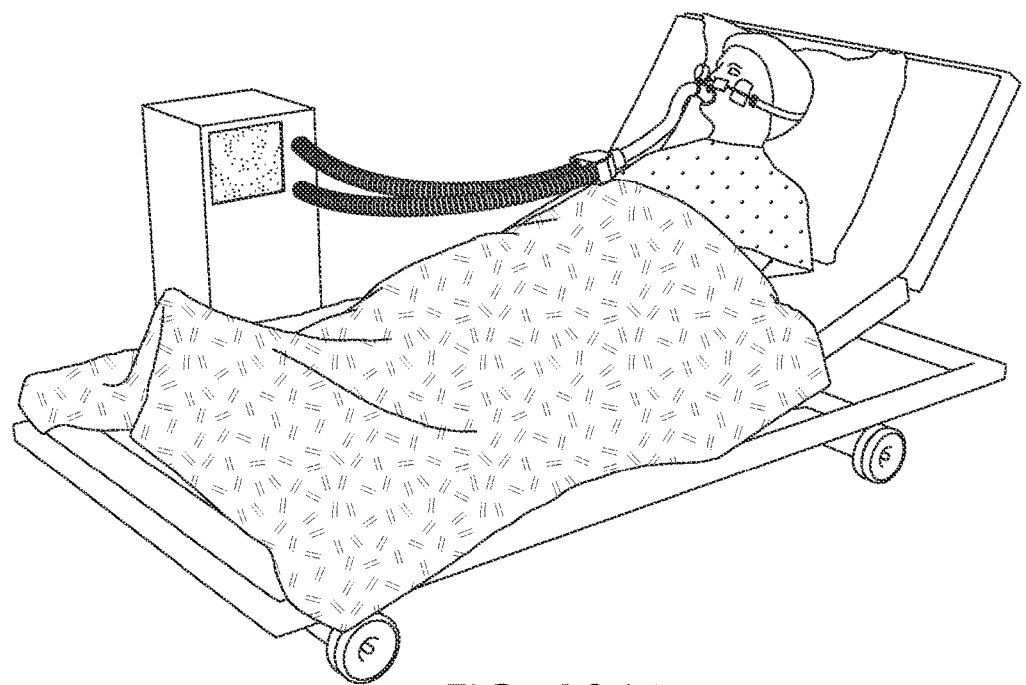
Figure 106B:
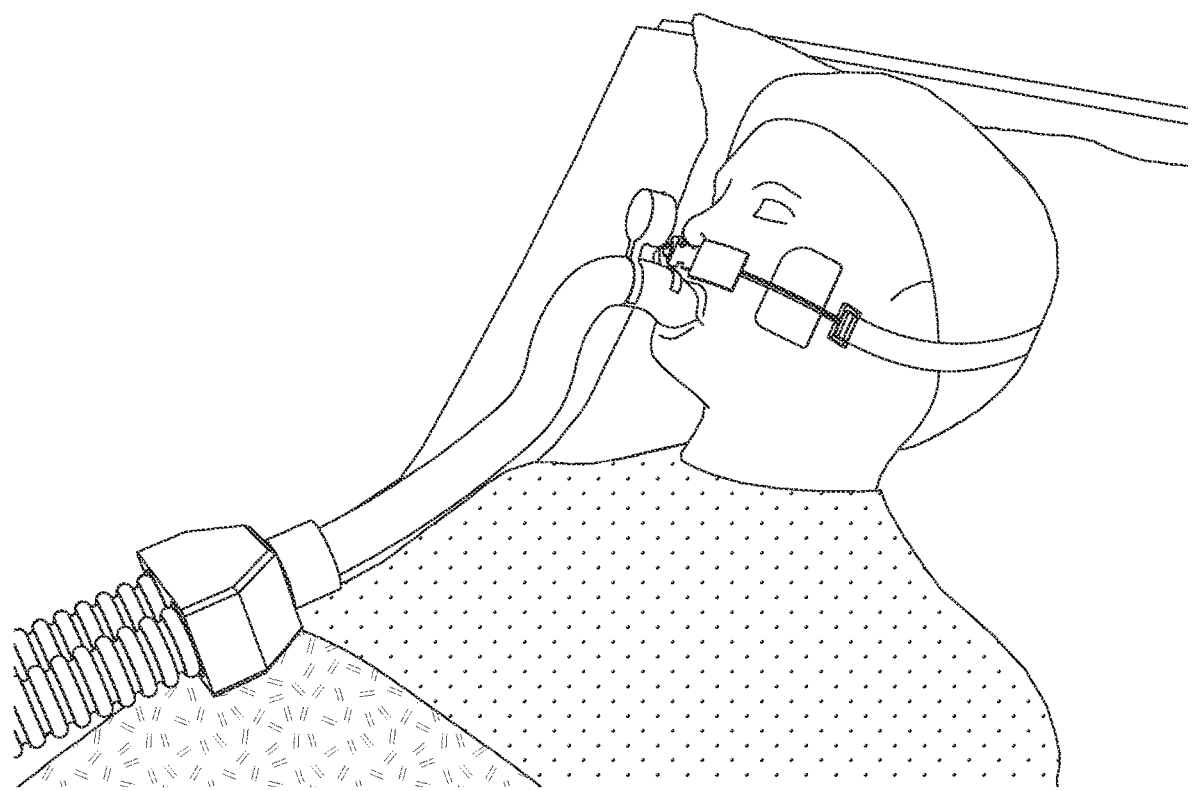

Referring now to FIGS. 68-83C, there is shown therapeutic light assembly 60 that is integrated into a ventilator mouthpiece/head strap 202. Light assembly 60 includes a plate 204 and a second plate 218 with a PCB 222 containing a plurality of therapeutic light sources 212. The therapeutic light sources 212 are packaged between the plate 204 and the second plate 218 by a plurality of strips. Each of the strips are held in place by ribs 226 extending from the edges of the second plate 218. The therapeutic light sources 212 shine through ports 232. Intubated patients often wear a mouthpiece or head strap to anchor ventilator tubing so it does not pull down or drag on the mouth or jaw of the patient and cause discomfort or injury. The head strap 202 here includes a plurality of spaced apart pads 208 and here therapeutic lights are shown mounted or integral to the mouthpiece/head strap in order to shine down on the nose and mouth of a patient where the most infectious virus would be localized and aerosolized. The head strap 202 is coupled to the light assembly 60 by a pair of spacing ribs 216. The head strap 202 further includes two loops 203 (e.g., as shown in FIG. 70) configured to accept a strap that wraps around the back of a patient's neck to secure the head strap 202 (e.g., as shown in in FIGS. 83A-83C).

Activating this therapeutic light could also reduce virus count when the ventilator tubing is inserted which is a process that requires the HCP be in close contact to the mouth of a sick patient. Ventilator Tubing 70 can be attached to assembly 60 by tubing attachment anchor 214 which is placed off to the side of one of the ribs 216. The tubing attachment anchor 214 can swivel as necessary in order to attach to the tubing 70. The attachment swivels within the same plane as the light assembly 60. The Ventilator mouthpiece/head strap designs can vary but typically include a strap to tighten around the head, a portion that contacts the front of the patient's head typically between the nose and mouth, and a portion for attaching the ventilator tube via an adhesive or a clip or some other mechanism. It may include at least one adhesive patch to anchor the mouthpiece/head strap to the patient's head. Ventilator tubing may be single or bifurcated, flexible, extendable, etc. Device may include an optical lens. Full device showing mouthpiece/head strap and ventilator tubing denoted as item 80. The embodiment shown connects via a wire 206 and lead 224 to an external power source but it could utilize integral battery power. With respect to FIGS. 81, there is shown a valve 304 that is between intermediate tubing 302 and corrugated ventilator tubing 306.

Referring to FIGS. 84-96B, there is shown therapeutic light assembly 314 integrated into a ventilator tube between corrugated ventilator tubing 316 and intubation tubing 312 into an assembly 100. The light assembly 314 includes therapeutic light source 328. The light assembly 314 is activated by push button 318. Intubated patients have a tube that goes down their throat into their lungs to assist in breathing when the lungs are compromised. With infectious respiratory diseases, the insertion, cleaning, removal, and other actions associated with a ventilator tube puts HCPs at risk of contracting airborne viruses and other contagions from an infectious patient. By integrating therapeutic lights into the tube, the light will shine down onto the mouth of the patient to reduce viral count on the patient, within the tube, traveling to the ventilator, and escaping into the air around the patient. Ventilator tubing may be single or bifurcated, flexible, extendable, etc.

Therapeutic lights are integrated directly into the tubing or may be assembled into a tubing assembly. Device may include an optical lens or the tubing may be manufactured from a material that transmits the therapeutic light. The ventilator tubing may be connected or attached to a mouthpiece/head strap as shown in assembly 110. The head strap can be attached to the tubing by attachment structure 404. Although an embodiment showing an endotracheal intubation device is included, this could easily be adapted for a naso-gastric or fiber-optic intubation device.

Referring to FIGS. 97-106B, there is shown attachable therapeutic light assembly 120 meant to attach a ventilator tube. The assembly 120 includes an attachable light body 332 which is attached to and co-planar with tube attachment clamp which does not turn. The printed circuit board (PCB) assembly 338 fits inside PCB assembly cavity 336 and covered up by lens cover 342 and lens 348. The lights are activated by push button 344. Here therapeutic light assembly 120 is a separate component (not built integral to the ventilator tubing) and attached to the ventilator tubing to shine down onto the mouth/nose of the patient to reduce viral count. A clip mechanism is shown, but it could be attached via an adhesive, a strap, a clamp, or some other mechanism. This allows the assembly 120 be attached independently to any tubing regardless whether there is a head strap and may allow for more universal application to varied ventilator tubing geometries from different manufacturers. Although an embodiment showing an endotracheal intubation device is included, this could easily be adapted for a naso-gastric or fiber-optic intubation device. The mouthpiece is shown as item 300 and the fully assembled embodiment denoted as item 130.

Referring now to FIGS. 107-115B, there is shown therapeutic light assembly 414 that is integrated into a tracheotomy tube between intermediate tubing 412 and corrugated ventilator tubing 416. The lights 428 are arranged circumferentially around PCB 422 and are powered by battery 426, which is activated by a push button 418. A tracheotomy or tracheostomy tube is a ventilator tube inserted via an incision in the neck directly into the trachea down into the lungs. A tracheotomy tubing typically includes a port that can be connected and disconnected on the surface of the neck and seals the incision in the neck and trachea. Nevertheless, having therapeutic light shining in and around the tube can work to reduce the viral count both within the tube and from anywhere around the tubing site. There could also be a wired or external power source instead of an integral battery power source.

Referring to FIGS. 116-134, there is shown a therapeutic lighting bag mask ventilation device which is a bag mask style ventilation device 502. These devices typically include some kind of facial mask 528 that seals over the nose and mouth and a bag 516 that attached via bag mask manifold 532, where the bag 516 that can be manually squeezed to force air into the lungs of a patient with respiratory difficulty. The lights 548 can be inserted into structures to house light component 506. Some ventilated patients that cannot be intubated may also have a modified ventilation via a mask connected to a ventilator. One embodiment shows therapeutic light located within the mask to shine directly over the nose and mouth of the infectious patient. This embodiment is shown as item 150.

An alternate embodiment places the therapeutic light within the airpath of the mask to reduce the viral load towards to bag to help protect HCPs especially those who are treating the patient by compressing the bag. This embodiment is shown as item 160. The mask may contain filter material through which air is expelled to capture any particulate exhaled by the patient. An alternate embodiment shows mask ventilation attached to tubing connected to a ventilator rather than to a bag. This embodiment is shown as item 170.

Referring now to FIGS. 135-140B, there is shown a therapeutic light personal protective mask. This concept 602 is not to reduce viral load at the site of viral shedding (infectious patient and their mouth, nose, or surgical site) but rather to treat infectious agents as they would be entering the body of an HCP. Applying therapeutic lights to a surgical mask, faceshield, goggles, or other devices would reduce viral load that made it past other PPE and to the HCP.

One embodiment is shown as item 180 and includes a surgical mask, shield, or face shield to protect the eyes, and a head strap to secure the device on 602. This embodiment includes therapeutic lights 638 within the mask to treat infectious agents before they are breathed in and therapeutic lights on attached to the shield to reduce viral load that may contact the eyes. A second embodiment is shown as item 190 which just includes therapeutic lights within the surgical mask. Both embodiments show battery powered lights but external power sources could be used as well. Both embodiments show LEDs but other types of therapeutic lights sources such as laser diodes could also be used.

While the subject disclosure has been shown and described with reference to preferred embodiments, those skilled in the art will readily appreciate that changes and/or modifications may be made thereto without departing from the spirit or scope of the subject disclosure.

What is claimed is:

1. A therapeutic light assembly for reducing an intubated patient's viral load comprising:
   a planar housing containing a plurality of spaced apart therapeutic light sources each configured to emit light toward the intubated patient's airway, wherein the planar housing includes an upper first plate and a lower second plate defining an interior area therebetween for accommodating a printed circuit board (PCB) containing the plurality of therapeutic light sources within the housing;
   a head strap coupled to the housing and configured to be positioned on the intubated patient's head below their nose; and a tubing attachment anchor coupled to the head strap and configured to secure the head strap to a ventilator tube of the intubated patient, wherein the head strap is coupled to the lower second plate of the housing by a pair of parallel spacing ribs.

2. The therapeutic light assembly of claim 1, wherein the head strap includes an arched base having a plurality of pads coupled thereto in an arcuately spaced apart manner.

3. The therapeutic light assembly of claim 1, wherein the lower second plate of the housing includes a plurality of ports to allow therapeutic light from the plurality of therapeutic light sources to shine there through directed towards the tubing attachment anchor.

4. The therapeutic light assembly of claim 1, wherein the tubing attachment anchor is rotatable about an axis extending perpendicular to the housing.

5. The therapeutic light assembly of claim 1, wherein the tubing attachment anchor is rotatable within a plane that extends parallel to a plane defined by the housing.

6. The therapeutic light assembly of claim 1, wherein a battery is housed within the housing to power the therapeutic light sources or the therapeutic light sources are connected to an external power source.

7. The therapeutic light assembly of claim 1, wherein the therapeutic light sources are UV LEDs.

* * * * *